United States Patent
Gilbert

(10) Patent No.: US 11,633,426 B2
(45) Date of Patent: *Apr. 25, 2023

(54) METHODS AND COMPOSITIONS FOR DOSING IN ADOPTIVE CELL THERAPY

(71) Applicant: Juno Therapeutics, Inc., Seattle, WA (US)

(72) Inventor: Mark J. Gilbert, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 537 days.

This patent is subject to a terminal disclaimer.

(21) Appl. No.: 16/667,564

(22) Filed: Oct. 29, 2019

(65) Prior Publication Data
US 2020/0054680 A1   Feb. 20, 2020

Related U.S. Application Data

(63) Continuation of application No. 14/918,451, filed on Oct. 20, 2015, now Pat. No. 10,507,219.

(60) Provisional application No. 62/215,732, filed on Sep. 8, 2015, provisional application No. 62/168,710, filed on May 29, 2015, provisional application No. 62/162,647, filed on May 15, 2015, provisional application No. 62/066,279, filed on Oct. 20, 2014.

(51) Int. Cl.
| | |
|---|---|
| A61K 35/17 | (2015.01) |
| C07K 16/28 | (2006.01) |
| A61K 45/06 | (2006.01) |
| B65D 25/20 | (2006.01) |
| A61K 39/00 | (2006.01) |

(52) U.S. Cl.
CPC ............ *A61K 35/17* (2013.01); *A61K 45/06* (2013.01); *B65D 25/205* (2013.01); *C07K 16/2803* (2013.01); *A61K 2039/515* (2013.01); *A61K 2039/545* (2013.01); *C07K 2317/622* (2013.01)

(58) Field of Classification Search
CPC ...... C07K 2317/622; A61K 39/001112; A61K 2039/545; A61K 2039/5156
See application file for complete search history.

(56) References Cited

U.S. PATENT DOCUMENTS

| | | | |
|---|---|---|---|
| 4,452,773 | A | 6/1984 | Molday |
| 4,690,915 | A | 9/1987 | Rosenberg |
| 4,795,698 | A | 1/1989 | Owen |
| 5,087,616 | A | 2/1992 | Myers |
| 5,200,084 | A | 4/1993 | Liberti |
| 5,219,740 | A | 6/1993 | Miller |
| 6,040,177 | A | 3/2000 | Riddell |
| 6,207,453 | B1 | 3/2001 | Maass |
| 6,410,319 | B1 | 6/2002 | Raubitschek |
| 6,451,995 | B1 | 9/2002 | Cheung |
| 7,070,995 | B2 | 7/2006 | Jensen |
| 7,265,209 | B2 | 9/2007 | Jensen |
| 7,354,762 | B2 | 4/2008 | Jensen |
| 7,446,179 | B2 | 11/2008 | Jensen |
| 7,446,190 | B2 | 11/2008 | Sadelain |
| 7,446,191 | B2 | 11/2008 | Jensen |
| 7,514,537 | B2 | 4/2009 | Jensen |
| 8,324,353 | B2 | 12/2012 | Jensen |
| 8,389,282 | B2 | 3/2013 | Sadelain |
| 8,399,645 | B2 | 3/2013 | Campana |
| 8,497,118 | B2 | 7/2013 | Jensen |
| 8,822,647 | B2 | 9/2014 | Jensen |
| 8,911,993 | B2 | 12/2014 | June |
| 9,169,328 | B2 | 10/2015 | Spriggs |
| 2002/0131960 | A1 | 9/2002 | Sadelain |
| 2003/0170238 | A1 | 9/2003 | Gruenberg |
| 2003/0215427 | A1 | 11/2003 | Jensen |
| 2004/0043401 | A1 | 3/2004 | Sadelain |
| 2011/0003380 | A1 | 1/2011 | Miltenyi |
| 2012/0148552 | A1* | 6/2012 | Jensen ............... C07K 14/5437 536/23.4 |

(Continued)

FOREIGN PATENT DOCUMENTS

| | | |
|---|---|---|
| CN | 103 145 849 | 6/2013 |
| CN | 103 547 676 | 1/2014 |

(Continued)

OTHER PUBLICATIONS

Kandalaft et al. (Journal of Translational Medicine, 2012, vol. 10, 10 pages) (Year: 2012).*
Kochenderfer et al (Journal of Clinical Oncology, published on-line Aug. 25, 2014, vol. 33, pp. 540-549) (Year: 2014).*
Xu et al, "Closely related T-memory stem cells correlate with in vivo expansion of of CAR.CD19-T cells and are preserved by IL-7 and IL-15," Blood (2014) 123(24):3750-59.
US 8,252,592, 1/1970, Sadelain (withdrawn)
U.S. Appl. No. 16/616,938, filed Jun. 1, 2018, by Albertson et al.

(Continued)

*Primary Examiner* — Karen A. Canella
(74) *Attorney, Agent, or Firm* — Morrison & Foerster LLP

(57) ABSTRACT

Provided are methods for administering multiple doses of cells, such as T cells, to subjects for cell therapy. Also provided are compositions and articles of manufacture for use in the methods. The cells generally express recombinant receptors such as chimeric receptors, e.g., chimeric antigen receptors (CARs) or other transgenic receptors such as T cell receptors (TCRs). The methods generally involve administering a first and at least one consecutive dose of the cells. Timing of the doses relative to one another, and/or size of the doses, in some embodiments provide various advantages such as lower or reduced toxicity and improved efficacy, for example, due to increased exposure of the subject to the administered cells. In some embodiments, the first dose is a relatively low dose, such as one that reduces tumor or disease burden, thereby improving the efficacy of consecutive or subsequent doses, and the consecutive dose is a consolidating dose.

43 Claims, 26 Drawing Sheets
Specification includes a Sequence Listing.

(56) References Cited

U.S. PATENT DOCUMENTS

| | | | |
|---|---|---|---|
| 2013/0149337 | A1 | 6/2013 | Cooper |
| 2013/0287748 | A1 | 10/2013 | June |
| 2014/0271635 | A1 | 9/2014 | Brogdon |
| 2014/0314795 | A1 | 10/2014 | Riddell |
| 2015/0283178 | A1 | 10/2015 | June |
| 2015/0306141 | A1 | 10/2015 | Jensen |
| 2016/0009813 | A1 | 1/2016 | Themeli |
| 2016/0045551 | A1 | 2/2016 | Brentjens |
| 2016/0122782 | A1 | 5/2016 | Crisman et al. |
| 2016/0158359 | A1 | 6/2016 | Gilbert |
| 2016/0206656 | A1 | 7/2016 | Gilbert |
| 2016/0362472 | A1 | 12/2016 | Bitter |
| 2019/0112379 | A1 | 4/2019 | Jensen |
| 2019/0277858 | A1 | 9/2019 | Li |
| 2019/0287013 | A1 | 9/2019 | Li |
| 2019/0355459 | A1 | 11/2019 | Li |

FOREIGN PATENT DOCUMENTS

| | | |
|---|---|---|
| EP | 0452342 B1 | 11/1994 |
| EP | 2537416 B1 | 11/2014 |
| RU | 2623038 | 6/2017 |
| WO | WO0014257 A1 | 3/2000 |
| WO | WO02077029 A3 | 5/2003 |
| WO | WO2006060878 A1 | 6/2006 |
| WO | WO2009072003 A2 | 6/2009 |
| WO | WO2010033140 A2 | 3/2010 |
| WO | WO 2012/062904 | 5/2012 |
| WO | WO2012079000 A4 | 8/2012 |
| WO | WO 2012/128628 | 9/2012 |
| WO | WO2012129514 A1 | 9/2012 |
| WO | WO2013071154 A1 | 5/2013 |
| WO | WO2013123061 A1 | 8/2013 |
| WO | WO2013126726 A1 | 8/2013 |
| WO | WO2013166321 A1 | 11/2013 |
| WO | WO2014031687 A1 | 2/2014 |
| WO | WO2014055668 A1 | 4/2014 |
| WO | WO2014055442 A9 | 7/2014 |
| WO | WO2014153270 A1 | 9/2014 |
| WO | WO2015157391 A1 | 10/2015 |
| WO | WO 2016/019300 | 2/2016 |
| WO | WO 2016/033570 | 3/2016 |
| WO | WO2016090190 A1 | 6/2016 |
| WO | WO2016172606 A1 | 10/2016 |
| WO | WO 2016/191756 | 12/2016 |
| WO | WO2016191756 A1 | 12/2016 |
| WO | WO2017096331 A1 | 6/2017 |
| WO | WO2017161208 A1 | 9/2017 |
| WO | WO2017161212 A1 | 9/2017 |
| WO | WO2017165571 A1 | 9/2017 |
| WO | WO2018102787 A9 | 10/2018 |
| WO | WO2017214207 A8 | 11/2018 |
| WO | WO2018157171 A3 | 11/2018 |
| WO | WO2018223101 A1 | 12/2018 |

OTHER PUBLICATIONS

Abramson Cancer Center of the University of Pennsylvania: "Autologous Redirected RNA Meso-CIR T Cells," ClinicalTrials.gov Identifier: NCT01355965. Retrieved from the Internet: URL:https://clinicaltrials.gov/show/NCT01355965 [retrieved on Sep. 30, 2014].

Abramson Cancer Center of the University of Pennsylvania: "Genetically Engineered Lymphocyte Therapy in Treating Patients With B-Cell Leukemia or Lymphoma That isResistant to Chemotherapy", ClinicalTrials.gov Identifier: NCT01029366, Retrieved from the Internet: URL:http://clinicaltrials.gov/show/NCT01029366 [retrieved on Sep. 24, 2014].

Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2:e93.

Baylor College of Medicine: "Activated T-Cells Expressing 2nd or 3rd Generation CD-19-Specific CAR, Advanced B-Cell NHL, ALL, and CLL (SAGAN)", ClinicalTrials.gov Identifier: NCT01853631, Retrieved from the Internet: URL: https://clinicaltrials.gov/ct2/show/NCT01853631?term=NCT01853631&rank=1 [retrieved on Jan. 29, 2016].

Baylor College of Medicine: "CD19 Chimeric Receptor Expressing T Lymphocytes in B-Cell Non Hodgkin's Lymphoma, ALL & CLL (CRETI_NH)", ClinicalTrials.gov Identifier: NCT00586391, Retrieved from the Internet: URL:https://clinicaltrials.gov/show/NCT00608270[retrieved on Sep. 24, 2014].

Baylor College of Medicine: "Kappa-CD28 T Lymphocytes, Chronic Lymphotic Leukemia, Bcell Lymphoma or Multiple Myeloma, CHARKALL", ClinicalTrials.gov Identifier: NCT00881920, Retrieved from the Internet: URL:https://clinicaltrials.gov/ct2/show/NCT00881920?term=NCT00881920&rank=1 [retrieved on Jan. 29, 2016].

Baylor College of Medicine: "T-Cells or EBV Specific CTLs, Advanced B-Cell NHL and CLL (Atecrab)", ClinicalTrials.gov Identifier: NCT00709033, Retrieved from the Internet: URL:https://clinicaltrials.gov/show/NCT00709033 [retrieved on Sep. 24, 2014].

Berger et al., "Safety of targeting ROR1 in primates with chimeric antigen receptor-modified T cells" Cancer Immunol Res (2015) 3(2): 206-16.

Bonifant et al., "Toxicity and management in CAR T-cell therapy," Molecular Therapy-Oncolytics (2016) 3:16011.

Boris-Lawrie et al., "Recent advances in retrovirus vector technology," Cur. Opin. Genet. Develop. (1993) 3:102-109.

Brash et al., "Strontium phosphate transfection of human cells in primary culture: stable expression of the simian virus 40 large-T-antigen gene in primary human bronchial epithelial cells," Mol Cell Biol. (1987) 7: 2031-2034.

Brentjens et al., "CD19-targeted T cells rapidly induce molecular remissions in adults with chemotherapy-refractory acute lymphoblastic leukemia," Sci Transl Med. (2013) 5(177).

Brentjens et al., "Safety and persistence of adoptively transferred autologous CD19-targeted T cells in patients with relapsed or chemotherapy refractory B-cell leukemias," Blood (2011) 118(18):4817-4828.

Brentjens et al., "Treatment of chronic lymphocytic leukemia with genetically targeted autologous T cells: case report of an unforeseen adverse event in a phase I clinical trial," MolTher. Apr. 2010;18(4):666-8.

Brentjens, "Adoptive Therapy of Cancer with T cells Genetically Targeted to TumorAssociated Antigens through the Introduction of Chimeric Antigen Receptors (CARs): Trafficking, Persistence, and Perseverance," (2011) Slide Deck of Oral Presentation made at American Society of Gene & Cell Therapy 14th Annual Meeting.

Brentjens, "Dosing Strategies: Goals and Options," Slide Deck of Oral Presentation made at NIH T cell Immunotherapy—Optimizing Trial Design Symposium, Bethesda, MD (2013) 14 pages, Retrieved from the Internet: URL: http://osp.od.nih.gov/sites/default/files/3_Brentjens_s3.pdf [retrieved on Dec. 28, 2016].

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.

Carlens et al., "Ex vivo T lymphocyte expansion for retroviral transduction: influence of serum-free media on variations in cell expansion rates and lymphocyte subset distribution," Exp Hematol (2000) 28(10): 1137-1146.

Cavaletti et al., "Chemotherapy-induced peripheral neurotoxicity," Nature Reviews Neurology (2010) 6, 657-666.

Cavalieri et al., "Human T lymphocytes transduced by lentiviral vectors in the absence of TCR activation maintain an intact immune competence," Blood (2003) 102(2): 497-505.

Chicaybam et al., "An efficient low cost method for gene transfer to T lymphocytes," PLoS ONE (2013) 8(3): e60298.

Cho et al., "Human mammalian cell sorting using a highly integrated micro-fabricated fluorescence-activated cell sorter (microFACS)," Lab Chip (2010) 10: 1567-1573.

Clinical Trial Study Record No. NCT01822652. Updated Dec. 24, 2015. Accessed Feb. 8, 2016.

Clinical Trial Study Record No. NCT02315612. Updated Nov. 10, 2015. Accessed Feb. 8, 2016.

(56) References Cited

OTHER PUBLICATIONS

Cooper et al., "T-cell clones can be rendered specific for CD19: toward the selective augmentation of the graft-versus-B-lineage leukemia effect," Blood. (2003) 101:1637 1644.
Davila et al., "CD19 CAR-targeted T cells induce long-term remission and B Cell Aplasia in an immunocompetent mouse model of B cell acute lymphoblastic leukemia," PLoS ONE (2013) 8(4):e61338.
Davila et al., "Chimeric antigen receptor therapy for chronic lymphocytic leukemia: what are the challenges?," Hematol Oncol Clin North Am. (2013) 27(2):341-53.
Davila et al., "Efficacy and toxicity management of 19-28z Car T cell therapy in B cell acute lymphoblastic leukemia," Sci Transl Med (2014) 6:224ra25.
Davila et al., "How do CARs work?: Early insights from recent clinical studies targeting CD19," Oncoimmunology (2012) 1(9):1577-1583.
Dudley et al., "Cancer regression and autoimmunity in patients after clonal repopulation with antitumor lymphocytes," Science (2002) 298:850-54.
Fedorov et al., "PD-1- and CTLA-4-based inhibitory chimeric antigen receptors (iCARs) divert off-target immunotherapy responses," Sci Transl Med. (2013) 5(215):215ra172.
Fred Hutchinson Cancer Research Center: "Laboratory Treated T Cells in Treating Patients With Relapsed or Refratory Chronic Lymphocytic Leukemia, Non-Hodgkin Lymphoma, or Acute Lymphoblastic Leukemia", ClinicalTrials.gov Identifier: NCT01865617, Retrieved from the Internet: URL:http://clinicaltrials.gov/show/NCT01865617 [retrieved on Aug. 26, 2014].
Gilham et al., "CAR-T cells and solid tumors: tuning T cells to challenge an inveterate foe," Trends Mol. Med. (2012) 18(7):377-384.
Godin et al., "Microfluidics and photonics for Bio-System-on-a-Chip: a review of advancements in technology towards a microfluidic flow cytometry chip," J Biophoton. (2008) 1(5):355-376.
Grupp et al., "Chimeric antigen receptor-modified T cells for acute lymphoid leukemia," N. Engl. J. Med. (2013) 368:1509-1518.
Han et al., "Chimeric antigen receptor-engineered T cells for cancer immunotherapy: progress and challenges," Journal of Hematology & Oncology (2013) 6:47.
Hermans et al., "The VITAL assay: a versatile fluorometric technique for assessing CTL- and NKT-mediated cytotoxicity against multiple targets in vitro and in vivo," J. Immunological Methods (2004) 285(1): 25-40.
Heslop, "Safer CARS," Mol Ther. Apr. 2010;18(4):661-2.
Huang et al., "DNA transposons for modification of human primary T lymphocytes," Methods Mol Biol (2009) 506: 115-126.
Hudecek et al., "Receptor affinity and extracellular domain modifications affect tumor recognition by ROR1-specific chimeric antigen receptor T cells," Clin Cancer Res Jun. 15, 2013;19(12):3153-1364.
Jensen et al., "Antitransgene rejection responses contribute to attenuated persistence o fadoptively transferred CD20/CD19-specific chimeric antigen receptor redirected T cells in humans," Biol Blood Marrow Transplant. Sep. 2010; 16(9):1245-1256.
Johnston, et al., "Biolistic transformation: microbes to mice," Nature (1990) 346: 776-777.
Kalos et al., "T cells with chimeric antigen receptors have potent antitumor effects and can establish memory in patients with advanced leukemia," Sci Transl Med (2011) 3(95):95ra73.
Kershaw et al., "Clinical application of gentically modified T cells in cancer therapy," Clin. Transl.l Immunol. (2014) 3(5):e16.
Klebanoff et al., "Sorting through subsets: which T-cell populations mediate highly effective adoptive immunotherapy?," J Immunother. (2012) 35(9): 651-660.
Kochenderfer et al, "A phase I clinical trial of treatment of B-cell malignancies with autologous anti-CD19-CAR-Transduced T Cells," Blood (2010) 116(21):1179-1180 Abstract 2865.

Kochenderfer et al., "B cell depletion and remissions of malignancy a long with cytokine associated toxicity in a clinical trial of anti-CD 19 chimeric-antigen receptor-transduced T cells," Blood (2012) 119(12):2709-2720.
Kochenderfer et al., "Construction and preclinical evaluation of an anti-CD19 chimeric antigen receptor," J. Immunotherapy (2009) 32(7): 689-702.
Kochenderfer et al., "Treating B-cell cancer with T cells expressing anti-CD19 chimeric antigen receptors," Nature Reviews Clinical Oncology (2013) 10, 267-276.
Koste et al., "T-cell receptor transfer into human T cells with ecotropic retroviral vectors," Gene Therapy (2014) 21: 533-538.
Lamers et al., "Immune responses to transgene and retroviral vector in patients treated with ex vivo-engineered T cells," Blood (2011) 117:72-82.
Lanier, "Viral immunoreceptor tyrosine-based activation motif (ITAM)-mediated signaling in cell transformation and cancer," Trends Cell Bio. (2006) 16(8):388-390.
Lee et al., "Current concepts in the diagnosis and management of cytokine release syndrome," Blood. (2014) 124 (2):188-95.
Lupton et al., "Dominant positive and negative selection using a hygromycin phosphotransferase-thymidine kinase fusion gene," Mol. and Cell Biol. (1991) 11(6):3374-3378.
M.D. Anderson Cancer Center: "Autologous CD-10-specific T Cells Infusion", ClinicalTrials.gov Identifier: NCT00968760, Retrieved from the Internet: URL:https://clinicaltrials.gov/show/NCT00968760 [retrieved on Sep. 24, 2014].
M.D. Anderson Cancer Center: "CD19-specific T-cell for Chronic Lymphocytic Leukemia (CLL)", ClinicalTrials.gov Identifier: NCT01653717, Retrieved from the Internet: URL:https://clinicaltrials.gov/show/NCT01653717 [retrieved on Sep. 24, 2014].
Manuri et al., "piggyBac transposon/transposase system to generate CD19-specific T cells for the treatment of B-lineage malignancies," Hum Gene Ther (2010) 21(4): 427-437.
Maus et al., "T cells expressing chimeric antigen receptors can cause anaphylaxis in humans," Cancer Immunol Res. Jul. 2013;1(1):26-31.
Memorial Sloan-Kettering Cancer Center: "Consolidation Therapy With Autologous T Cells Genetically Targeted to the B Cell Specific Antigen CD19 . . . ", ClinicalTrials.gov Identifier: NCT01416974, Retrieved from the Internet: URL:http://clinicaltrials.gov/show/record/NCT01416974 [retrieved on Sep. 24, 2014].
Memorial Sloan-Kettering Cancer Center: "Precursor B Cell Acute Lymphoblastic Leukemia (B-ALL) Treated With Autologous T Cells Genetically Targeted to the B Cell Specific Antigen CD19", ClinicalTrials.gov Identifier: NCT01044069, Retrieved from the Internet: URL:http://clinicaltrials.gov/ct2/show/NCT01044069 [retrieved on Aug. 26, 2014].
Memorial Sloan-Kettering Cancer Center: "T-Lymphocytes Genetically Targeted to the B-Cell Specific Antigen CD19 in Pediatric and Young Adult Patients With Relapsed B-Cell AcuteLymphoblastic Leukemia", ClinicalTrials.gov Identifier: NCT01860937, Retrieved from the Internet: URL:http://clinicaltrials.gov/ct2/show/NCT01860937?term=nct01860937&rank=1[retrieved on Jan. 29, 2016].
Memorial Sloan-Kettering Cancer Center: "Treatment of Relapsed or Chemotherapy Refractory Chronic Lymphocytic Leukemia or Indolent B Cell Lymphoma Using Autologous T Cells Genetically Targeted to the B Cell Specific Antigen CD19", ClinicalTrials.gov Identifier: NCT00466531, Retrieved from the Internet: URL:https://clinicaltrials.gov/show/NCT00466531[retrieved on Sep. 24, 2014].
Methods in Molecular Medicine, vol. 58: Metastasis Research Protocols, vol. 2: Cell Behavior In Vitro and In Vivo, p. 17-25 Edited by: S. A. Brooks and U. Schumacher © Humana Press Inc., Totowa, NJ.
Miller et al., "Improved retroviral vectors for gene transfer and expression," BioTechniques (1989) 7:980-990.
Miller et al., "Retrovirus packaging cells," Human Gene Therapy (1990) 1:5-14.
Mullen et al., "Transfer of the bacterial gene for cytosine deaminase to mammalian cells confers lethal sensitivity to 5-fluorocytosine: a negative selection system," Proc. Natl. Acad. Sci. USA (1992)89(1):33-37.

(56) References Cited

OTHER PUBLICATIONS

Muranski et al., "Increased intensity lymphodepletion and adoptive immunotherapy—how far can we go?," Nat Clin Pract Oncol. (2006) 3(12):668-681.
National Cancer Institute (NCI): "A Phase I Trial of T Cells Expressing an Anti-GD2 Chimeric Antigen Receptor in Children and Young Adults With Non-neuroblastoma, GC2+ Solid Tumors", ClinicalTrials.gov Identifier: NCT02107963, Retrieved from the Internet: URL:https://clinicaltrials.gov/show/NCT02107963 [retrieved on Sep. 26, 2014].
National Cancer Institute—Common Toxicity Criteria version 4.03 (NCI-CTCAE v4.03). Jun. 14, 2010.
National Cancer Institute: "Phase 1 Study of B Cell Malignancies Using T Cells Expressing and Anti-CD19 Chimeric Receptor: Assessment of the Impact of Lymphocyte Depletion Prior to TCell Transfer", ClinicalTrials.gov Identifier: NCT00924326, Retrieved from the Internet: URL:https://clinicaltrials gov/show/NCT00924326 [retrieved on Sep. 24, 2014].
Newick et al., "Chimeric antigen receptor T-cell threapy for solid tumors," Mol. Ther. Oncolytics (2016) 3:16006.
Park et al,, "Adoptive transfer of chimeric antigen receptor re-directed cytolytic T lymphocyte clones in patients with neuroblastoma," Molecular Therapy (2007) 15(4):825-833.
Park et al., "Phase I Clinical Trial of Autologous CD19-Targeted 19-28z CAR T Cells in Adult Patients With Relapsed or Refractory B-ALL," Mol. Ther. (2015) 23(Supp. 1):S188-89.
Park et al., "Treating cancer with genetically engineered T cells," Trends Biotechnol. (2011) 29(11): 550-557.
Porter et al., "Chimeric antigen receptor-modified T cells in chronic lymphoid leukemia," N Engl J Med. Aug. 25, 2011;365(8):725-33.
Porter et al., "Randomized, Phase II Dose Optimization Study of Chimeric Antigen Receptor Modified T Cells Directed Against CD19 (CTL019) in Patients With Relapsed, Refractory CLL," Blood. Nov. 2013;122(21):873, 3 pages, Retrieved from the Internet:URL:http://www.bloodjournal.org/content/122/21/873?sso-checked=true; [retrieved on Sep. 24, 2014].
Riddell et al., "T-cell mediated rejection of gene-modified HIV-specific cytotoxic T lymphocytes in HIV-infected patients," Nature Medicine (1996) 2:216-223.
Rosenberg et al., "Durable complete responses in heavily pretreated patients with metastatic melanoma using T-cell transfer immunotherapy," Clin Cancer Res (2011) 17(13):4550-4557.
Rosenberg, et al., "Cell transfer immunotherapy for metastatic solid cancer—what clinicians need to know," Nat Rev Clin Oncol. (2011) 8(10):577-585.
Sadelain et al., "The basic principles of chimeric antigen receptor design," Cancer Discov. (2013) 3(4): 388-398.
Savoldo et al., "CD28 costimulation improves expansion and persistence of chimeric antigen receptor-modified T cells in lymphoma patients," JCI (2011) 121(5):1822-1826.
Scarpa et al., "Characterization of recombinant helper retroviruses from Moloneybased vectors in ecotropic and amphotropic packaging cell lines," Virology (1991) 180:849-852.
Sharma et al., "Efficient sleeping beauty DNA transposition from DNA minicircles," Molec Ther Nucl Acids (2013) 2:e74.
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10): 928-933.
Tsukahara et al., "CD19 target-engineered T-cells accumulate at tumor lesions in human B-cell lymphoma xenograft mouse models," Biochem Biophys Res Commun (2013) 438(1): 84-89.

Turtle et al., "Anti-CD19 Chimeric Antigen Receptor-Modified T Cell Therapy for B Cell Non-Hodgkin Lyphoma and Chronic Lyphocytic Leukemia: Fludarabine and Cyclophosphamide Lyphodepletion Imprives In Vivo Expansion and Persistence of CAR-T Cells and Clinical Outcomes," Blood (2015) 126:184.
Turtle et al., "CD19 Car-T cells of defined CD4+:CD8+ composition in adult B cell ALL patients," J Clin Invest. (2016) 126(6):2123-2138.
Turtle et al., "Engineered T cells for anti-cancer therapy," Curr. Opin. Immunol. (2012) 24(5): 633-639.
Turtle et al., "Immunotherapy of non-Hodgkin's lymphoma with adefined ratio of CD8+ and CD4+ CD19-specific chimeric antigen receptor-modified T cells," Sci Trasl Med (2016) 8(355):355ra116.
Turtle et al., "Immunotherapy with CD19-specific chimeric antigen receptor (CAR)-modified T cells of defined subset composition," J. Clin. Oncol. (2015) 33:Suppl. Abstr 3006.
University of Pennsylvania, "Phase I/IIA Study of CART19 Cells for Patients With Chemotherapy Resistant or Refractory CD19+ Leukemia and Lymphoma (Pedi CART19)," ClinicalTrials.gov Identifier:NCT01626495, Retrieved from the Internet:URL:https://clinicaltrials.gov/ct2/show/NCT01626495 [retrieved on Dec. 28, 2016].
Van Tendeloo et al., "High-level transgene expression in primary human T lymphocytes and adult bone marrow CD34+ cells via electroporation-mediated gene delivery," Gene Therapy (2000) 7(16): 1431-1437.
Verhoeyen et al., "Lentiviral vector gene transfer into human T cells," Methods Mol Biol. (2009) 506: 97-114.
Wadhwa et al., "Receptor mediated glycotargeting," J. Drug Targeting (1995) 3(2):111-127.
Wang et al., "Phenotypic and functional attributes of lentivirus-modified CD19-specific human CD8+ central memory T cells manufactured at clinical scale," J Immunother (2012) 35(9):689-701.
Wigler et al., "Transfer of purified herpes virus thymidine kinase gene to cultured mouse cells," Cell (1977) 11: 223-232.
Wu et al., "Adoptive T-cell therapy using autologous tumor-infiltrating lymphocytes for metastatic melanoma: current status and future outlook," Cancer (2012) 18(2): 160-175.
Xu et al., "Cytokine release syndrome in cancer immunotherapy with chimeric antigen receptor engineered T cells," Cancer Letters (2014) 343:172-78.
Yee et al., "Adoptive T cell therapy using antigen-specific CD8+ T cell clones for the treatment of patients with metastatic melanoma: in vivo persistence, migration, and antitumor effect of transferred T cells," Proc Natl Acad Sci U S A. Dec. 10, 2002;99(25):16168-73.
Yee, "Adoptive T cell therapy: Addressing challenges in cancer immunotherapy," J Transl Med. Apr. 28, 2005;3(1):17.
Avdic et al., "Human Cytomegalovirus-Encoded Human Interleukin-10 (IL-10) Homolog Amplifies Its Immunomodulatory Potential by Upregulating Human IL-10 in Monocytes," J Virol. (2016) 90(8): 3819-3827.
Chen et al., Hematology (2014) Fourth Military Medical University Press, p. 64.
Chen et al., Questions and Answers for Pediatricians (2013) Military Medical Science Press, p. 146.
Law et al., "What does it take to bind CAR?," Mol Ther. (2005) 12(4):599-609.
Franke et al., "Antibodies against CD20 or B-cell receptor induce similar transcription patterns in human lymphoma cell lines," PLoS One.(2011) 6(2): e16596.
Davila et al., "Chimeric antigen receptors for the adoptive T cell therapy of hematologic malignancies," Int J Hematol. (2014) 99(4):361-71.

\* cited by examiner

CD8+/CAR-

METHODS AND COMPOSITIONS FOR DOSING IN ADOPTIVE CELL THERAPY

CROSS-REFERENCE TO RELATED APPLICATIONS

This application is a continuation of U.S. patent application Ser. No. 14/918,451, filed Oct. 20, 2015, entitled "Methods and Compositions for Dosing in Adoptive Cell Therapy," which claims priority to U.S. provisional application No. 62/066,279 filed Oct. 20, 2014, entitled "Methods and Compositions for Dosing in Adoptive Cell Therapy," U.S. provisional application No. 62/162,647, filed May 15, 2015, entitled "Methods and Compositions for Dosing in Adoptive Cell Therapy," U.S. provisional application No. 62/168,710, filed May 29, 2015, entitled "Methods and Compositions for Dosing in Adoptive Cell Therapy," and U.S. provisional application No. 62/215,732, filed Sep. 8, 2015, entitled "Methods and Compositions for Dosing in Adoptive Cell Therapy," the contents of which are incorporated by reference in their entirety.

INCORPORATION BY REFERENCE OF SEQUENCE LISTING

The present application is being filed with a Sequence Listing in electronic format. The Sequence Listing is provided as a file entitled 735042001001seqlist.txt, created Oct. 25, 2019, which is 15,410 bytes in size. The information in electronic format of the Sequence Listing is incorporated by reference in its entirety.

FIELD

The present disclosure relates to adoptive cell therapy involving the administration of multiple doses of cells, and methods, compositions, and articles of manufacture for use in the same. The cells generally express recombinant receptors such as chimeric receptors, e.g., chimeric antigen receptors (CARs) or other transgenic receptors such as T cell receptors (TCRs). Features of the methods, including the timing of the doses and numbers of cells administered, provide various advantages, such as lower toxicity and/or improved efficacy, for example, due to increased exposure of the subject to the administered cells. In some embodiments, the first dose involves a relatively lower number of cells compared with dosage amounts administered in other methods. In some embodiments, the first dose reduces tumor or disease burden, thereby improving the efficacy of consecutive or subsequent doses. In some embodiments, the timing of a consecutive dose is designed to minimize risk of toxicity and/or host immune response to the cells by the subject, thereby improving persistence and efficacy.

BACKGROUND

Various methods are available for adoptive cell therapy using engineered cells expressing recombinant receptors, such as chimeric antigen receptor (CARs). Improved methods are needed, for example, to reduce the risk of toxicity and/or to increase efficacy, for example, by increasing exposure of the subject to the administered cells, for example, by improving expansion and/or persistence of the administered cells. Provided are methods, compositions, and articles of manufacture that meet such needs.

SUMMARY

Provided are methods of for administering to subjects cells expressing genetically engineered (recombinant) cell surface receptors in adoptive cell therapy, for example, to treat diseases and/or conditions in the subjects. The methods generally involve administering multiple doses of such cells, and/or administering a consecutive dose to a subject having been previously treated with a prior (e.g., first) dose of such cells. In some embodiments, the doses are a first dose and one or more consecutive doses. In some embodiments, the first dose is a relatively low dose and/or is a conditioning or debulking dose and/or the consecutive dose(s) is a consolidating dose(s). Also provided are cells, compositions, and articles of manufacture for use in such methods. In some embodiments, the recombinant receptors are genetically engineered antigen receptors, such as functional non-TCR antigen receptors, e.g., chimeric antigen receptors (CARs) and other recombinant antigen receptors such as transgenic T cell receptors (TCRs). Also among the receptors are other recombinant chimeric receptors, such as those containing an extracellular portion that specifically binds to a ligand or receptor or other binding partner and an intracellular signaling portion, such as the intracellular signaling portion of a CAR. The doses in some embodiments include a relatively low first dose.

In some embodiments, the methods involve (a) administering to a subject with a disease or condition a first dose of cells expressing a recombinant receptor (e.g., chimeric antigen receptor (CAR)), the first dose containing the cells; and (b) administering to the subject a consecutive dose of recombinant receptor-expressing (e.g., CAR-expressing) cells. In other embodiments, e.g., for providing consolidating treatment, the methods are carried out by administering to the subject the consecutive dose or doses as in (b), to a subject that has been previously administered the first dose as in (a).

In some embodiments, the methods involve (a) administering to a subject having a disease or condition a first dose of cells expressing a recombinant receptor (e.g., chimeric antigen receptor (CAR)). In some embodiments, the first dose contains no more than about $1 \times 10^6$ of the cells per kilogram body weight of the subject, no more than about $1 \times 10^8$ of the cells, and/or no more than about $1 \times 10^8$ of the cells/m$^2$ of the subject. In some embodiments, the methods further involve (b) administering to the subject a consecutive dose of cells expressing a recombinant receptor (e.g., CAR) at a time point that is at least or more than about 14 days after and less than about 28 days after initiation of the administration in (a).

In some embodiments, at the time of the administration in (b) the serum level in the subject of a factor indicative of cytokine release syndrome (CRS) is less than about 10 times, less than about 25 times, and/or less than about 50 times that in the subject immediately prior to said administration in (a). In some embodiments, the subject does not exhibit grade 3 or higher neurotoxicity. In some embodiments, a CRS-related outcome or symptom of neurotoxicity in the subject following the administration of the first dose has reached a peak level and begun to decline following the administration in (a). In some embodiments, the subject does not exhibit a detectable humoral or cell-mediated immune response against the receptor (e.g., CAR) expressed by the cells of said first dose.

In some embodiments, the methods further involve the administration of additional consecutive or subsequent doses, such that a first and multiple consecutive doses are administered, e.g., in accordance with the dosing amounts and timing schedules as specified for the first and consecutive doses. In some embodiments, the first of one or more subsequent doses is administered at a time that is at least or greater than 14 days after the initiation of the administration of the consecutive dose. In some embodiments, the administration of the first, consecutive, and subsequent doses includes administering at least three of the doses within at or about 28 days. In some embodiments, the consecutive dose is administered at about day 14 following the initiation of administration of the first dose, and an additional consecutive or subsequent dose is administered at day 28 following the initiation of administration of the first dose. In some embodiments, additional subsequent doses are administered at day 42 and/or day 56 following the initiation of administration of the first dose.

In some embodiments, the first dose is administered in an amount sufficient to reduce burden of the disease or condition in the subject. In some embodiments, the first dose is a low dose, such as a debulking dose, such as a dose that is lower than that required to eradicate the disease or condition but that may effect a reduction in burden or bulk of such disease or condition. In some embodiments, the administration of the first dose does not induce severe cytokine release syndrome (CRS) in the subject. In some embodiments, administration of the first dose does not induce CRS in the subject. In some embodiments, based on clinical data, administration of the first dose does not induce severe CRS in a majority of subjects. In some embodiments, the administration of the first dose does not induce CRS encompassing a combination of (1) persistent fever (fever of at least 38 degrees Celsius for at least three days) and (2) a serum level of C reactive protein (CRP) of at least at or about 20 mg/dL, and/or does not induce CRS encompassing hypotension requiring the use of two or more vasopressors or respiratory failure requiring mechanical ventilation.

In some embodiments, administration of the first dose does not induce grade 3 or higher neurotoxicity in the subject. In some embodiments, based on clinical data, administration of the first dose does not induce grade 3 or higher neurotoxicity in a majority of subjects. In some embodiments, symptoms associated with a clinical risk of neurotoxicity and/or grade 3 or higher neurotoxicity include confusion, delirium, expressive aphasia, obtundation, myoclonus, lethargy, altered mental status, convulsions, seizure-like activity, seizures (optionally as confirmed by electroencephalogram [EEG]), elevated levels of beta amyloid (Aβ), elevated levels of glutamate, and elevated levels of oxygen radicals.

In some embodiments, the first dose is lower than a dose that would cause CRS or severe CRS in the subject. In some embodiments, the first dose comprises no more than about $1 \times 10^6$ of the cells per kilogram body weight of the subject, no more than $5 \times 10^5$ of the cells per kilogram body weight of the subject, no more than about $1 \times 10^8$ of the cells, or no more than about $1 \times 10^8$ of the cells/m$^2$ of the subject.

In some embodiments, the consecutive dose(s) is administered at a time at which a clinical risk for neurotoxicity, cytokine-release syndrome (CRS), macrophage activation syndrome, or tumor lysis syndrome, is not present or has passed or has subsided following the administration of the first (or prior) dose. In some embodiments, the consecutive dose is administered at a time at which a biochemical readout evidencing CRS, neurotoxicity, macrophage activation syndrome, or tumor lysis syndrome, is not present or has passed or has subsided following said administration of the first (or prior) dose. In some embodiments, the consecutive dose(s) is administered at a time at which a serum level of a factor indicative of cytokine-release syndrome (CRS) or neurotoxicity in the subject is less than about 10 times, less than about 25 times, and/or less than about 50 times the serum level of the indicator in the subject immediately prior to said administration of the first dose. In some embodiments, the consecutive dose(s) is administered at a time after a neurotoxicity and/or CRS-related outcome or serum factor indicating CRS in the subject has reached a peak level and begun to decline following said administration, such as where at the time of the administration of the consecutive dose, the level of a CRS-related outcome or serum factor indicative of CRS is no more than 50% of the peak level, is no more than 20% of the peak level, or is no more than 5% of the peak level, or is at or about the level immediately prior to the administration of the first dose.

In some embodiments, the subject does not exhibit cytokine release syndrome (CRS), does not exhibit severe CRS, does not exhibit neurotoxicity, does not exhibit severe neurotoxicity, or does not exhibit neurotoxicity above grade 3 following administration of the first dose and/or following the administration of the consecutive dose.

Among the CRS-related outcomes are fever, hypotension, hypoxia, neurologic disturbances, or a serum level of an inflammatory cytokines, such as interferon gamma (IFNγ), granulocyte-macrophage colony-stimulating factor (GM-CSF), tumor necrosis factor alpha (TNFα), IL-6, IL-10, IL-10, IL-8, IL-2, MIP-1, Flt-3L, fracktalkine, and IL-5, and C reactive protein (CRP). Among the factors, e.g., serum factors, indicative of CRS are inflammatory cytokines such as IFNγ, GM-CSF, TNFα, IL-6, IL-10, IL-10, IL-8, IL-2, MIP-1, Flt-3L, fracktalkine, and IL-5, and CRP.

In some aspects, the time of administering the consecutive dose(s) is further one at which the subject does not exhibit an immune response, e.g., does not exhibit a detectable adaptive host immune response specific for the receptor (e.g., CAR) expressed by the cells of said first (or prior) dose.

In some embodiments, the time between the administration of the first dose, e.g., the initiation of the administration of the first or prior dose, and the initiation of the administration of the consecutive dose (e.g., the initiation of the administration of the consecutive dose) is greater than about 4 days, e.g., greater than about 5, 6, 7, 8, or 9 days, e.g., greater than about 20 days, e.g., between about 9 and about 35 days, between about 14 and about 28 days, between 15 and 27 days, or between 17 days and about 21 days; and/or at or about 15, 16, 17, 18, 19, 20, 21, 22, 23, 24, 25, 26, or 27 days. In some embodiments, administration of the consecutive dose (e.g., initiation thereof) is more than about 14 days after and less than about 28 days after administration of the first or prior dose (e.g., initiation thereof). In some embodiments, the administration of the consecutive dose is initiated 21 days following the initiation of the first dose. In some embodiments, the time between administration of the first and the consecutive dose (e.g., initiation thereof) or prior and next consecutive dose is greater than about 14 days and less than about 28 days, such as between 15 and 27 days, such as about 21 days. In some embodiments, the time between administration of the first and the consecutive dose (e.g., initiation thereof) is about 17 days.

In some embodiments, at the time of the administration of the consecutive dose, the serum level in the subject of a factor indicative of CRS is less than about 10 times, less than about 25 times, and/or less than about 50 times that in the subject immediately prior to said administration of the first dose; and/or a CRS-related outcome in the subject following said administration of said first dose has reached a peak level and begun to decline following the administration in (a); and/or the subject does not exhibit a detectable humoral or cell-mediated immune response against the receptor (e.g., CAR) expressed by the cells of said first dose. In some embodiments, at the time of the administration in (b) or of the consecutive dose, the serum level of said factor indicative of CRS is no more than ten times the level immediately prior to the administration in (a) or of the first dose.

In some embodiments, the subject has not received a dose of cells expressing the receptor (e.g., CAR) that is expressed by the cells in the first dose prior to the administration in (a). In some embodiments, the receptor (e.g., the CAR) expressed by the cells in the consecutive dose contains at least one immunoreactive epitope present in the receptor (e.g., CAR) expressed by the cells in the first dose. In some embodiments, the receptor in the cells of the consecutive dose is identical or substantially identical to the receptor (e.g. the CAR) expressed by the cells in the first dose. In some embodiments, the receptor expressed by the cells of the first dose specifically binds to an antigen expressed by a cell or tissue of the disease or condition or associated with the disease or condition. In some embodiments, the receptor expressed by the cells of the consecutive dose binds to the same antigen, e.g., to the same epitope, and/or contains the same antigen-binding domain as that in the first dose.

In some embodiments, the disease or condition is a tumor. In some embodiments, it is a cancer, malignancy, neoplasm, or other proliferative disease or disorder, such as leukemia, lymphoma, e.g., chronic lymphocytic leukemia (CLL), ALL, non-Hodgkin's lymphoma, acute myeloid leukemia, multiple myeloma, refractory follicular lymphoma, mantle cell lymphoma, indolent B cell lymphoma, B cell malignancies, cancers of the colon, lung, liver, breast, prostate, ovarian, skin, melanoma, bone, and brain cancer, ovarian cancer, epithelial cancers, renal cell carcinoma, pancreatic adenocarcinoma, Hodgkin lymphoma, cervical carcinoma, colorectal cancer, glioblastoma, neuroblastoma, Ewing sarcoma, medulloblastoma, osteosarcoma, synovial sarcoma, and/or mesothelioma. In some embodiments, the disease or condition is a leukemia or lymphoma. In some embodiments, the disease or condition is acute lymphoblastic leukemia. In some embodiments, the disease or condition is non-Hodgkin lymphoma (NHL).

In some embodiments, the disease is a cancer and the subject does not exhibit morphologic disease at the time of initiation of the administration of the consecutive dose. In some embodiments, the disease is a leukemia or lymphoma and the subject does not exhibit greater than 5% blast cells in the bone marrow at the time of the administration of the consecutive dose. In some embodiments, the subject exhibits detectable molecular disease and/or minimum residual disease at the time of the administration of the consecutive dose.

In some embodiments, administration of the first dose leads to a reduction in burden of the disease or condition in the subject, for example, as indicated by a reduction in one or more factors indicative of disease burden following said administration of the first dose, e.g., following the administration in (a). In some embodiments, at the time of the administration in (b) or of the consecutive dose, the subject has not relapsed and/or the one or more factors indicative of disease burden have not increased following the initial reduction experienced after the first dose. In some embodiments, the consecutive dose of cells contains cells in an amount sufficient for reduction in burden of a disease or condition in the subject. In some embodiments, the administration of the consecutive dose leads to a further reduction in burden of the disease or condition in the subject. In some embodiments, administration of the consecutive dose leads to a reduction in burden of the disease or condition in the subject as compared with immediately prior to initiation of the administration of the consecutive dose. In some embodiments, the method reduces burden of the disease or condition to a greater degree and/or for a greater period of time as compared to a method with an alternative dosing regimen wherein the subject is administered the cells in the first dose and the cells in the consecutive dose in a single dose. The reduction in burden and/or further reduction in burden may comprise a reduction in total number of cells, e.g., tumor cells, of the disease in the subject, in an organ of the subject, in a tissue of the subject, or in a bodily fluid of the subject. The reduction may comprise a reduction in molecular detection by flow cytometry or quantitative PCR, mass or volume of a tumor, and/or a reduction in number and/or extent of metastases. In some embodiments, the reduction comprises improvement in survival of the subject, e.g., increased time of survival or incident-free, progression-free, or relapse-free survival.

In some embodiments, the disease or condition persists following the administration of the first dose and/or the administration of the first dose is not sufficient to eradicate the disease or condition in the subject. In some embodiments, the administration of said consecutive dose leads to a reduction in burden of the disease or condition in the subject as compared with immediately prior to initiation of the administration of the consecutive dose.

In some embodiments, the methods reduce burden of the disease or condition to a greater degree and/or for a greater period of time as compared to a method comprising an alternative dosing regimen wherein the subject is administered the cells in (a) (or of the first dose) and the cells in (b) (or of the consecutive dose) in a single dose. In some embodiments, the area under the curve (AUC) of recombinant receptor-expressing (e.g., CAR-expressing) cells over time, and/or the duration of detectable receptor-expressing cells in the subject following the administration of the consecutive dose (or the administration in (b)) is greater as compared to that achieved via a method comprising an alternative dosing regimen wherein the subject is administered the cells in (a) (or the first dose) and the cells in (b) (or the consecutive dose) as a single dose. In some embodiments, the method results in a maximum concentration or number of receptor-expressing (e.g., CAR-expressing) cells in the blood of the subject of at least at or about 10 receptor-expressing cells per microliter, at least at or about 100 receptor-expressing cells per microliter, at least 50% of the total number of peripheral blood mononuclear cells (PBMCs), at least at least about $1 \times 10^5$ receptor-expressing cells, or at least 5,000 copies of recombinant receptor-encoding (e.g., CAR-encoding) DNA per micrograms DNA, or at least 10,000 copies of recombinant receptor-encoding DNA per micrograms of DNA. In some embodiments, at day 90 following the initiation of the administration in (a) or of the first dose, recombinant receptor-expressing (e.g., CAR-expressing) cells are detectable in the blood or serum of the subject, e.g., the blood of the subject contains at least 10%, at least 20%, at least 40%, or at least 50%, receptor (e.g., CAR)-expressing cells, at least 10 receptor (e.g., CAR)-expressing cells per microliter or at least $1 \times 10^4$ receptor (e.g., CAR)-expressing cells.

In some embodiments, the AUC for blood concentration of receptor-expressing (e.g., CAR-expressing) cells over time following the administration in (a) or of the first dose is greater as compared to that achieved via a method comprising an alternative dosing regimen wherein the subject is administered the cells in (a) or of the first dose and the cells in (b) or of the second dose as a single dose.

In some embodiments, a CRS-related outcome in the subject at day 2, 3, 4, 5, 6, 7, 8, 9, 10, 11, 12, 13, or 14 following the administration in (b) or of the consecutive dose is not detectable or is reduced as compared to a method comprising an alternative dosing regimen wherein the subject is administered the cells in (b) or the consecutive dose without having been administered the first dose.

In some embodiments, the AUC for a serum level of a factor indicative of CRS over time in the subject following the administration in (b) or the consecutive dose is lower as compared to that of a method comprising an alternative dosing regimen wherein the subject is administered the cells in (b) or the consecutive dose without having been administered the first dose.

In some embodiments, the subject has been treated with a therapeutic agent targeting the tumor prior to the administration of the first dose. In some aspects, the subject is refractory or non-responsive to said therapeutic agent at the time of the administration of the first dose and/or the consecutive dose. In some embodiments, subsequent to administration in (a) or the first dose and before said administration in (b) or the consecutive dose, or prior to administration in (a) or the first dose, the methods further include assessing a serum level of a factor indicative of CRS, a factor indicative of disease burden, and/or an indicator of a host anti-recombinant receptor (e.g., anti-CAR) immune response in the subject, such as a humoral or cell-mediated immune response. In some such embodiments, the factor indicative of disease burden detected is or comprises a total number of cells of the disease in the subject, in an organ of the subject, in a tissue of the subject, or in a bodily fluid of the subject, molecular detection by flow cytometry or quantitative PCR, mass or volume of a solid tumor, or number or extent of metastases.

In some embodiments, the methods include assessing a factor indicative of disease burden prior to administration of the consecutive dose, and based on the result of the assessment, determining the consecutive dose of cells to be administered to the subject. In some embodiments, if the assessment determines that the subject has morphologic disease, the subject is administered a consecutive dose containing less than or about the same number of recombinant receptor- (e.g., CAR-)expressing cells as the number of recombinant receptor- (e.g., CAR-)expressing cells in the first dose. In some embodiments, if the assessment determines that the subject has minimal residual disease, the subject is administered a consecutive dose containing an increased number of receptor- (e.g., CAR-)expressing cells as compared to the first dose. In some embodiments, the consecutive dose comprises about the same number of recombinant receptor-expressing (e.g., CAR-expressing) cells as the number in the first dose. In some embodiments, the number of receptor- (e.g., CAR-) expressing cells per kilogram administered in the consecutive dose is less than or about less than or is the same or about the same as the number of receptor- (e.g., CAR-)expressing cells per kilogram administered in the first dose. In other embodiments, the number of receptor-expressing (e.g., CAR-expressing) cells per kilogram administered in the consecutive dose is greater than the number of receptor-expressing (e.g., CAR-expressing) cells per kilogram administered in the first dose. In some embodiments, the consecutive dose comprises an increased number of such cells as compared to the first dose, such as at least 2-fold, 5-fold, or 10-fold greater than the number in the first dose. In some embodiments, the number of receptor-expressing (e.g., CAR-expressing) cells per kilogram administered in the consecutive dose is at least at or about 2 times or at or about 3 times greater than the number of receptor-expressing (e.g., CAR-expressing) cells per kilogram administered in the first dose.

In some embodiments, the receptor-expressing (e.g., CAR-expressing) cells in the first dose expand in the subject following administration of the first dose and/or following the administration of the consecutive dose. In some embodiments, the expansion is evidenced by an increase in serum CRP level following the administration of the first dose and/or consecutive dose as compared to just prior to the administration. In some embodiments, the expansion is evidenced by an increase in a level of receptor- (e.g., CAR-) encoding nucleic acid in the serum, as measured by qPCR, following the administration of the first dose and/or consecutive dose as compared to just prior to the administration. In some embodiments, the increase is at least 1, 2, or 3-fold.

In some embodiments, the first and/or consecutive dose is not a split does. For example, in some embodiments, the cells of the first dose are administered in a single pharmaceutical composition comprising the cells of the first dose and/or the cells of the consecutive dose are administered in a single pharmaceutical composition comprising the cells of the consecutive dose. In other embodiments, the first and/or consecutive dose is a split dose, for example, where the cells of the first dose are administered in a plurality of compositions, collectively comprising the cells of the first dose, over a period of no more than three days; and/or the consecutive dose is a split dose, where the cells of the consecutive dose are administered in a plurality of compositions, collectively comprising the cells of the consecutive dose, over a period of no more than three days.

In some embodiments, the methods include administering a consecutive dose of cells expressing a recombinant receptor (e.g., a chimeric antigen receptor (CAR)) to a subject previously administered a first dose of cells expressing a CAR. In some embodiments, the consecutive dose of cells is administered at a time point that is at least or more than about 14 days after and less than about 28 days after initiation of the first dose. In some embodiments, the number of receptor- (e.g., CAR-)expressing cells administered in the consecutive dose is increased as compared to the first dose.

In some embodiments, the number of cells administered in the first dose is between about $0.5 \times 10^6$ cells/kg body weight of the subject and $3 \times 10^6$ cells/kg, between about $0.75 \times 10^6$ cells/kg and $2.5 \times 10^6$ cells/kg or between about $1 \times 10^6$ cells/kg and $2 \times 10^6$ cells/kg, each inclusive.

In some embodiments, the number of cells administered in the consecutive dose of receptor- (e.g., CAR-)expressing cells is between about $2 \times 10^6$ cells per kilogram (cells/kg) body weight and about $6 \times 10^6$ cells/kg, between about $2.5 \times 10^6$ cells/kg and about $5.0 \times 10^6$ cells/kg, or between about $3.0 \times 10^6$ cells/kg and about $4.0 \times 10^6$ cells/kg, each inclusive.

In some embodiments, the number of receptor- (e.g., CAR-)expressing cells administered in the first dose is at or about or no more than at or about $1 \times 10^6$ per kilogram of the subject and/or the number of receptor- (e.g., CAR-)expressing cells administered in the consecutive dose is at or about $3 \times 10^6$ per kilogram of the subject.

In some embodiments, the methods further include administering a chemotherapeutic agent prior to the administration in (a) or prior to the first dose and/or prior to the administration in (b) or prior to the consecutive dose. In some embodiments, the subject has been previously treated with a chemotherapeutic agent prior to the administration in (a). In some embodiments, the chemotherapeutic agent is or comprises a conditioning chemotherapy, which reduces burden of the disease or condition in the subject prior to the first dose and/or consecutive dose. In some embodiments, the chemotherapeutic agent is cyclophosphamide, fludarabine, and/or a combination thereof. In some embodiments, the administration of the chemotherapeutic agent includes administration of a chemotherapeutic agent prior to the administration of the first dose and optionally not prior to the administration of the consecutive dose. In some embodiments, the chemotherapeutic agent is administered between 2 and 5 days prior to the administration of the first dose. In some embodiments, the chemotherapeutic agent is administered between 2 and 5 days prior to the administration of the second dose. In some embodiments, the chemotherapeutic agent is administered between 2 and 5 days prior to the administration first dose and between 2 and 5 days prior to the administration of the second dose. In some embodiments, the chemotherapeutic agent is administered at a dose of between at or about 1 g/m$^2$ of the subject and at or about 3 g/m$^2$ of the subject.

In some embodiments, the subject has received cryoreductive chemotherapy prior to the administration or the first dose. In some embodiments, the method further includes the administration of cryoreductive chemotherapy prior to the administration of the first dose.

Also provided are cells and compositions for use and uses of cells and compositions for treating a disease or condition in a subject, such as a tumor or cancer, where said cells contain recombinant receptor- (e.g., chimeric antigen receptor (CAR)-)expressing cells for treatment of a disease or condition in a subject or for the manufacture of a medicament for treatment of a disease or condition in a subject previously treated with recombinant receptor-expressing (e.g., CAR-expressing) cells. In some embodiments, the compositions or cells for use or medical uses are for use 14 to 28 days after the previous treatment. In some embodiments, the compositions or cells for use are formulated for administration of a consecutive dose in an amount sufficient for reduction in burden of a disease or condition in the subject having been previously treated with the recombinant receptor-expressing (e.g., CAR-expressing) cells.

In some embodiments of such medical uses, the compositions or cells are for use that includes administering to a subject having the disease or condition a first dose of cells expressing the receptor (e.g., CAR). In some embodiments, the first dose contains no more than about 1×10$^6$ of the cells per kilogram body weight of the subject, no more than about 1×10$^8$ of the cells, and/or no more than about 1×10$^8$ of the cells/m$^2$ of the subject. In some embodiments, the compositions or cells are for use that includes administering to the subject a consecutive dose of cells expressing a receptor (e.g., CAR) at a time point that is at least or more than about 14 days after and less than about 28 days after initiation of the administration of the first dose.

In some embodiments, the cells for use are cells expressing a recombinant receptor (e.g., chimeric antigen receptor (CAR)) are for use in methods of treating a disease in a subject previously treated with receptor- (e.g., CAR-)expressing cells. In some embodiments, the cells are for use between about 14 and 28 days after the previous treatment. In some embodiments, the cells for use are formulated for administration of a consecutive dose in an amount sufficient for reduction in burden of a disease or condition in the subject having been previously treated with the receptor- (e.g., CAR-)expressing cells.

In some embodiments of any such compositions or cells for use or medical uses, the subject does not exhibit morphologic disease and/or the subject does not exhibit greater than 5% blast cells in the bone marrow.

In some embodiments, the compositions or cells are for use in a method including administering to a subject having the disease or condition a first dose of cells expressing the receptor (e.g., CAR). In some embodiments, the first dose contains no more than about 1×10$^6$ of the cells per kilogram body weight of the subject, no more than about 1×10$^8$ of the cells, and/or no more than about 1×10$^8$ of the cells/m$^2$ of the subject. In some embodiments, the cells are for use in a method that includes administering to the subject a consecutive dose of cells expressing a receptor (e.g., CAR) at a time point that is at least or more than about 14 days after and less than about 28 days after initiation of said administration of the first dose.

In some embodiments, the compositions or cells for use are formulated for administration in an amount that does not induce severe CRS in the subject or does not induce CRS in the subject. In some embodiments, the cells for use are formulated for administration in an amount that does not induce grade 3 or higher neurotoxicity in the subject. In some embodiments, the cells for use are formulated for administration in an amount that, based on clinical data, does not induce severe CRS in a majority of subjects so-treated. In some embodiments, the cells for use are formulated for administration in an amount that, based on clinical data, does not induce grade 3 or higher neurotoxicity in a majority of subjects so-treated.

In some embodiments, the use of cells expressing a receptor (e.g., chimeric antigen receptor (CAR)) are for manufacture of a medicament for the treatment of a disease or condition in a subject includes cells that are formulated and/or packaged for administration to the subject in a first and a consecutive dose. In some embodiments, the treatment includes administering the cells to the subject in a first and a consecutive dose, where the first dose includes no more than about 1×10$^6$ of the cells per kilogram body weight of the subject, no more than about 1×10$^8$ of the cells, and/or no more than about 1×10$^8$ of the cells/m$^2$ of the subject.

In some embodiments of any such compositions or cells for use or medical uses, the consecutive dose is for administration at a time point that is at least or more than about 14 days after and less than about 28 days after initiation of the first administration. In some embodiments, the consecutive dose is for administration at a time point at which the serum level in the subject of a factor indicative of cytokine release syndrome (CRS) is less than about 10 times, less than about 25 times, and/or less than about 50 times that in the subject immediately prior to said first administration. In some embodiments, the consecutive dose is for administration at a time point at which the subject does not exhibit grade 3 or higher neurotoxicity. In some embodiments, the consecutive dose is for administration at a time point at which a CRS-related outcome or symptom of neurotoxicity in the subject following said administration of said first dose has reached a peak level and begun to decline following the first administration. In some embodiments, the consecutive dose is for administration at a time point at which the subject does not exhibit a detectable humoral or cell-mediated immune response against the receptor (e.g., CAR) expressed by the cells of said first dose.

In some embodiments, the cells for use are formulated and/or packaged for administration to the subject in a first and a consecutive dose and/or the treatment includes administering the cells to the subject in a first and a consecutive dose. In some embodiments, the first dose contains no more than about 1×10$^6$ of the cells per kilogram body weight of the subject, no more than about 1×10$^8$ of the cells, and/or no more than about 1×10$^8$ of the cells/m$^2$ of the subject.

In some embodiments, the use includes where the first and consecutive administrations include administering the cells in one or more unit dose, each unit dose comprising about between $5\times10^7$ of the cells and about $5\times10^8$ cells, about between $5\times10^7$ of the cells and about $2.5\times10^8$ cells or about between $2.5\times10^8$ cells and $4\times10^8$ cells. In some embodiments, the cells are formulated in a unit dose comprising no more than about $5\times10^7$ cell, no more than about $1\times10^8$ cells, no more than about $2\times10^8$ of the cells, no more than about $2.5\times10^8$ of the cells, no more than about $3.0\times10^8$ of the cells or no more than about $4\times10^8$ of the cells.

In some embodiments, the cells or use includes where the first administration comprises administering a single unit dose. In some embodiments, the cells or use includes where the consecutive administration comprises administration of two or more unit doses. In some embodiments, the cells or use includes where the consecutive administration comprises administration a single unit dose.

In some embodiments, the cells composition for use or use includes where the disease or condition is a tumor or a cancer. In some embodiments, the cells or composition for use or use includes where the tumor or cancer is leukemia or lymphoma. In some embodiments, the composition or cells are for use in treating acute lymphoblastic leukemia. In some embodiments, the composition or cells are for use in treating non-Hodgkin lymphoma (NHL).

In some embodiments, the cells, composition, or use includes where the consecutive dose is formulated for administration of less than or about the same number of recombinant receptor-expressing (e.g., CAR-expressing) cells as the number of recombinant receptor-expressing (e.g., CAR-expressing) cells in the previous dose. In some embodiments, the composition containing the cells of the consecutive dose is formulated for administration of an increased number of recombinant receptor-expressing (e.g., CAR-expressing) cells as compared to the first dose or previous dose.

Also provided are articles of manufacture for carrying out the methods. In some embodiments, the article of manufacture includes a plurality of containers, e.g., sealable containers, each individually comprising a unit dose of cells expressing the recombinant receptor, e.g., chimeric antigen receptor (CAR), for administration to the subject, packaging material, and/or a label or package insert.

In some embodiments, the unit dose comprises the amount of cells to be given in the lowest dose in the methods, such as the size of the first dose. In some embodiments, the unit dose includes no more than about $1\times10^8$ of the cells, no more than about $5\times10^7$ of the cells, no more than about $1\times10^6$ of the cells per kg of the subject, or no more than about $5\times10^5$ of the cells per kg of the subject.

In some embodiments, the label or package insert includes instructions for administering a plurality of the unit doses to the subject, for example, by administering a certain number of such unit doses, e.g., one unit dose, in administration of a first dose, and then administering a consecutive dose including one or a plurality of the unit doses. In some embodiments, the instructions specify carrying out a first administration, said first administration comprising delivering one of said unit doses to the subject, and carrying out a consecutive administration, said consecutive administration comprising administering one or a plurality of said unit doses to the subject. In some embodiments, they specify that the consecutive administration is to be carried out at a time between about 15 and about 27 days following said first administration. In some embodiments, the instructions specify that the consecutive administration is to be carried out at a time after which it has been determined that a serum level of a factor indicative of cytokine-release syndrome (CRS) in the subject is less than about 10 times, less than about 25 times, and/or less than about 50 times the serum level of said indicator in the subject immediately prior to said previous dose, or at a time after which it has been determined that an indicator of CRS has peaked and is declining, such as is at less than at or about 40%, 30%, 20%, or 10% of the peak value, and/or that the subject does not exhibit a detectable adaptive host immune response specific for the receptor (e.g., CAR) expressed by the cells of the previous dose. In some embodiments, the containers are or comprise flexible cell infusion bags. In some embodiments, the cells to be administered and/or in the containers or unit doses are for autologous transfer. Thus, in some embodiments, the cells have been derived from the subject to which they are to be administered. In some embodiments, the methods are for allogeneic administration. In some embodiments, the label and/or packaging material further includes an identifier specific to the subject, indicating that the cells were derived from the subject and/or should be administered to the subject specifically.

In some embodiments, the cells are primary cells, such as primary human immune cells, e.g., PBMCs, T cells, and/or NK cells. In some embodiments, the cells comprise CD8+ and/or CD4+ T cells. In some embodiments, the T cells are autologous to the subject.

DETAILED DESCRIPTION

Figure 1A:
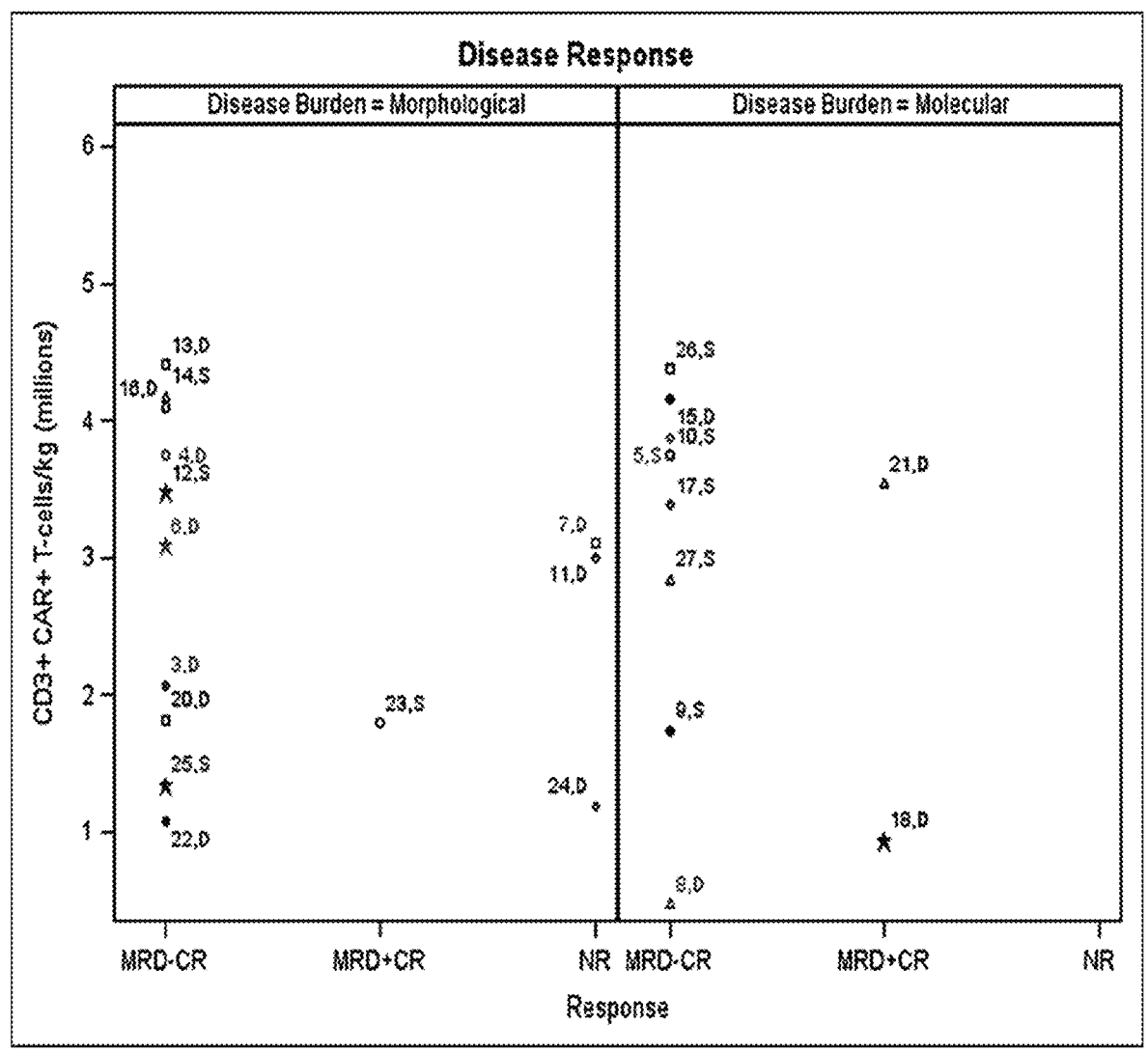
FIG. 1A shows disease responses of subjects with morphological or molecular disease (disease burden at time of treatment initiation) treated with a single infusion of varying doses of CAR-expressing T cells. MRD–CR=no minimal residual disease, complete remission; MRD+CR=minimal residual disease, complete remission; NR=not responsive

I. Methods of Treatment with Cells Expressing Recombinant Receptors

Provided are methods, compositions, and articles of manufacture for use in cell therapy, for the treatment of diseases or conditions including various tumors. The methods involve administering engineered cells expressing recombinant receptors designed to recognize and/or specifically bind to molecules associated with the disease or condition and result in a response, such as an immune response against such molecules upon binding to such molecules. The receptors may include chimeric receptors, e.g., chimeric antigen receptors (CARs), and other transgenic antigen receptors including transgenic T cell receptors (TCRs).

In particular, the methods involve administering one or more consecutive doses of cells to subjects having received a first dose, and/or administering the first and one or more consecutive doses. The doses generally are administered in particular amounts and according to particular timing parameters. In some embodiments, the methods generally involve administering a first dose of cells, thereby reducing disease burden, followed by a consecutive dose of cells, administered during a particular time window with respect to the first dose, or the administration of the consecutive dose to a subject having received such a first dose. The first dose is often a relatively low dose. In some embodiments, additional consecutive doses then are administered, for example, within the same or a similar window of time with respect to the consecutive dose. In some embodiments, the number of cells administered and timing of the multiple doses are designed to improve one or more outcomes, such as to reduce the likelihood or degree of toxicity to the subject, improve exposure of the subject to and/or persistence of the administered cells, and/or improve therapeutic efficacy. Also provided are articles of manufacture containing the cells and designed for administration following such dosing regimens.

In some embodiments, the provided methods are based on observations herein that increased exposure of the subject to the administered cells (e.g., increased number of cells or duration over time) can improve efficacy and therapeutic outcomes in adoptive cell therapy. Preliminary analysis conducted following the administration of different CD19-targeting CAR-expressing T cells to subjects with various CD19-expressing cancers in multiple clinical trials revealed a correlation between greater and/or longer degree of exposure to the CAR-expressing cells and treatment outcomes. Such outcomes included patient survival and remission, even in individuals with severe tumor burden.

Yet delivering high initial doses of the recombinant immunostimulatory cells does not necessarily increase exposure. Particularly in the context of high disease burden (and thus higher amounts of antigen), administering large doses does not necessarily enhance efficacy and can lead to increased or rapid expansion of the cells and result in toxicity. Certain reports have indicated a lack of correlation between dose and toxicity. See Park et al, Molecular Therapy 15(4):825-833 (2007). On the other hand, higher initial doses can promote toxic outcomes such as cytokine release syndrome (CRS), particularly in the context of high disease burden. Moreover, high doses do not necessarily translate to increased persistence of the administered cells, and thus do not necessarily increase exposure over time. See Park et al, Molecular Therapy 15(4):825-833 (2007). Likewise, administering cells in the context of high disease burden, often present at the outset of treatment, can lead to exhaustion of the transferred cells, thereby reducing clinical efficacy. See Davila & Brentjens, Hematol Oncol Clin North Am. 27(2):341-53 (2013).

Administering subsequent doses may not be effective, particularly following relapse and/or where the subject has mounted an immune response specific for the cells or the recombinant receptors the express. Improved methods are needed to increase cell exposure over time while avoiding toxic outcomes.

The provided methods offer advantages over other approaches aimed at addressing the risk of toxic outcomes and/or improving efficacy. Many such approaches have focused, for example, on targeting downstream effects of toxicity, such as by cytokine blockade, and/or delivering agents such as high-dose steroids which can also eliminate or impair the function of administered cells. Many of these other approaches also do not prevent other forms of toxicity such as neurotoxicity, which can be associated with adoptive cell therapy. On the other hand, administering relatively low doses of cells (e.g. CAR-expressing cells) may decrease the risk but may not be completely effective. Delivery of subsequent doses of cells, for example, after relapse following an initial administration, also has not been entirely satisfactory. Such dosing approaches can lead to limited or ineffective responses of the subsequent dose, due to host immune responses mounted against the initial dose.

Provided are methods involving the administration of consecutive doses of cell therapy in a way that minimizes risk of toxicity and maximizes efficacy. As observed herein, following administration of different types of CD19-targeting CAR T cells to human subjects with B cell cancers, initial doses equal to or below $1\times10^6$ cells per kilogram body weight were effective in reducing tumor burden. These low doses also were associated with less frequent severe CRS, neurotoxicity, and other adverse events compared with higher doses. In some embodiments, the provided methods involve the safe initial administration of such low doses, followed by consecutive dose(s) for increased exposure, with dose amounts and timing designed to avoid impairment of efficacy by host immune responses while minimizing risk of toxicity In some cases, if desired or need in a particular disease or context, the provided methods involve a consecutive dose of cells administered at an increased number, and hence at a higher dose, than the first dose of cells. As shown herein, in some aspects, administration of higher doses of cells is advantageous compared to lower doses. In some embodiments, administration of higher doses of cells, such as doses greater than or equal to $2.5\times10^6$ cells/kg or higher, are associated with an increased overall survival in subjects, particularly in subjects that exhibit morphological disease prior to treatment. In some embodiments, however, these higher doses can be associated with toxic outcomes, and in particular with neurotoxicity, such as severe neurotoxicity, for example grade 3 neurotoxicity or higher, particularly in subjects with morphological disease prior to treatment. In some cases, the toxic outcome following administration of high doses of recombinant receptor-expressing (e.g., CAR-expressing) cells is not observed, or is not observed to as great of an extent, when subjects with a reduced disease burden are treated, such as subjects with minimal residual disease having molecularly detectable disease. In some embodiments, methods of first administering a low dose of recombinant receptor-expressing (e.g., CAR-expressing) cells can reduce the disease burden in subjects, such as from morphological disease status to minimal residual disease, so that subsequent administration of a higher dose of recombinant receptor-expressing (e.g., CAR-expressing) cells in subjects is less likely to cause toxic outcomes in a majority of subjects treated. In some embodiments, the provided methods avoid the problems of toxicity associated with administration with higher doses, while maximizing the efficacy of treatment that can occur upon administration with higher numbers of recombinant receptor-expressing (e.g., CAR-expressing) cells.

In some embodiments, the methods include administering an initial dose of recombinant receptor-expressing (e.g., CAR-expressing) cells that can expand in the presence of disease-associated antigens and reduce disease burden but without the same degree of toxic outcomes that may be associated with a higher dose. In some aspects, the first dose is a low dose, such as a dose of less than at or about or no more than at or about $1\times10^6$ cells per kilogram body weight of the subject (cells/kg), $0.5\times10^6$ cells/kg or $1\times10^5$ cells/kg. In some aspects, the first dose is in an amount or number of cells that has been observed not to cause toxic outcomes in the disease or condition or subject, such as, in some embodiments, CRS or neurotoxicity. In some embodiments, the first dose is an amount or number of cells that has been associated with such outcomes, such as based on clinical data, in only a relatively small percentage of patients, such as no more than 50, 40, 25, 20, 15, 10, 5, or fewer percent of subjects.

In some embodiments, the first dose is generally also large enough to be effective in reducing disease burden. In some cases, the first dose is large enough to reduce disease burden if the cell dose is sufficient to expand in vivo and debulk disease. In some embodiments, the cells of the first dose thereby debulk or reduce disease burden, e.g., tumor size, without effecting severe unwanted outcomes. In some cases, the first dose is an amount of cells that is effective to reduce tumor burden, such as by reducing disease from a morphological setting to minimum residual disease and/or clinical or complete remission. In some aspects, the initial dose is a low dose. In some aspects, for example, in the context of relatively low disease burden, the first dose may be higher.

In some aspects, a risk-adapted dosing regime is used for determining the appropriate number or amount or relative number or amount of cells or recombinant receptor-expressing (e.g., CAR-expressing) cells in the dose. For example, in some aspects, prior to infusion of recombinant receptor-expressing (e.g., CAR-expressing) cells, the disease burden of the subject is determined and, based on the disease burden, a first dose of recombinant receptor-expressing (e.g., CAR-expressing) cells (e.g. low or high dose) is selected that can minimize toxicity and maximize efficacy, for example, based on observations described above and elsewhere herein in which higher doses of recombinant receptor-expressing cells (e.g., CAR-expressing, such as CAR-expressing T cells) can be associated with toxic outcomes, such as severe neurotoxicity, in subjects having morphological disease burden, which are not necessarily observed, or are not observed to as great of an extent, in subjects with relatively lower disease burden. For example, subjects with a high marrow tumor burden prior to treatment, which, in some cases, can be associated with a greater CAR T-cell expansion following treatment, were observed to have a higher risk of developing severe neurotoxicity that may require ICU care.

In some embodiments, in order to maximize efficacy in subjects that are not, or are less, susceptible to a toxic outcome following in infusion of recombinant receptor-expressing (e.g., CAR-expressing) cells, e.g. CAR-T cell infusion, (such as to subjects that do not exhibit morphologic disease (i.e. have non-morphologic disease) or do not exhibit substantial morphologic disease), a relatively higher dose of cells, such as greater than $1\times10^6$ cells/kg, $2\times10^6$ cells/kg, $5\times10^6$ cells/kg or $1\times10^7$ cells/kg, can be administered. Conversely, in some aspects, subjects that are determined to have a relatively higher disease burden, such as by the presence of morphologic disease or substantial morphologic disease, can be administered a relatively lower dose of cells than administered to subjects that do not exhibit morphologic disease or do not exhibit substantial morphologic disease, such as a dose of less than or equal to or about $1\times10^6$ cell/kg or less than or equal to or about $0.5\times10^6$ cells/kg. In some embodiments, one or more further consecutive doses can be administered, which, optionally, can be administered based on the extent or degree of disease burden as described above or alternatively be at a fixed dose regardless of disease burden. In some embodiments, a subject exhibits morphologic disease or substantial morphological disease burden if there are greater than or equal to or about 5% blasts present in the bone marrow. In some embodiments, a subject with higher relative disease burden, such has high marrow tumor burden, has greater than, equal to or greater than about 10% blasts in the bone marrow or greater than, equal to or greater than about 20% blasts in the bone marrow.

In some embodiments, a subject is assessed for disease burden prior to treatment, and, if the subject exhibits less than 5% bone marrow blast cells, the subject can be administered a dose of recombinant receptor-expressing (e.g., CAR-expressing, such as CAR-expressing T cells) of greater than $1\times10^6$ cells/kg, $2\times10^6$ cells/kg, $5\times10^6$ cells/kg or $1\times10^7$ cells/kg, or if the subject exhibits greater than or equal to 5% bone marrow blast cells, the subject can be administered a dose of recombinant receptor-expressing (e.g., CAR-expressing, such as CAR-expressing T cells) of less than or equal to or about $1\times106$ cell/kg or $0.5\times106$ cells/kg. In some embodiments, a subject is assessed for disease burden prior to treatment, and, if the subject exhibits less than 10% bone marrow blast cells, the subject can be administered a dose of recombinant receptor-expressing (e.g., CAR-expressing, such as CAR-expressing T cells) of greater than $1\times10^6$ cells/kg, $2\times10^6$ cells/kg, $5\times10^6$ cells/kg or $1\times10^7$ cells/kg, or if the subject exhibits greater than or equal to 10% bone marrow blast cells, the subject can be administered a dose of recombinant receptor-expressing (e.g., CAR-expressing, such as CAR-expressing T cells) of less than or equal to or about $1\times10^6$ cell/kg or $0.5\times10^6$ cells/kg. In some embodiments, a subject is assessed for disease burden prior to treatment, and, if the subject exhibits less than 20% bone marrow blast cells, the subject can be administered a dose of recombinant receptor-expressing (e.g., CAR-expressing, such as CAR-expressing T cells) of greater than $1\times10^6$ cells/kg, $2\times10^6$ cells/kg, $5\times10^6$ cells/kg or $1\times10^7$ cells/kg, or if the subject exhibits greater than or equal to 20% bone marrow blast cells, the subject can be administered a dose of recombinant receptor-expressing (e.g., CAR-expressing, such as CAR-expressing T cells) of less than or equal to or about $1\times10^6$ cell/kg or $0.5\times10^6$ cells/kg. In some embodiments, the disease burden is assessed and a risk-adapted dose is selected prior to the first dose of recombinant receptor-expressing (e.g., CAR-expressing, such as CAR-expressing T cells). In some embodiments, the disease burden is assessed and a risk-adapted dose is selected prior to one or more consecutive doses of recombinant receptor-expressing (e.g., CAR-expressing, such as CAR-expressing T cells).

In some embodiments, a consecutive dose of recombinant receptor-expressing (e.g., CAR-expressing) cells is administered to the subject at a time after administration of the first or initial dose of cells in which it is likely that tumor burden of the subject has been reduced by the first dose. In some embodiments, it is not necessary that the tumor burden actually be reduced in all subjects prior to administration of the consecutive dose, but that tumor burden is reduced on average in subjects treated, such as based on clinical data, in which a majority of subjects treated with such a first dose exhibit a reduced tumor burden, such as at least 50%, 60%, 70%, 80%, 90%, 95% or more of subjects treated with the first or initial dose exhibit a reduced tumor burden. Generally at a point in time after disease burden has been reduced by the first dose or is likely to have been reduced by the first dose, a consecutive dose is administered to the subject, thereby further reducing and/or eliminating disease or a symptom or outcome thereof or preventing expansion or progression thereof. The context of reduced disease burden at the time of the consecutive administration in some aspects reduces the likelihood of exhaustion of the transferred cells, thereby improving efficacy. The consecutive dose may be the same, lower, or a higher dose as compared with the first dose. In some embodiments, multiple consecutive doses are administered after a first dose.

In some embodiments, the consecutive dose of recombinant receptor-expressing (e.g., CAR-expressing) cells is administered at a dose that is higher than the first dose so that an increased number of recombinant receptor-expressing (e.g., CAR-expressing) cells is administered to the subject by the consecutive dose. In some embodiments, a higher dose of recombinant receptor-expressing (e.g., CAR-expressing) cells is one that can promote an increased response or efficacy, such as improved or greater reduction in tumor burden and/or an improved or greater overall survival time of the subject compared to that achieved by administration of a lower dose or number of cells. In some embodiments, because administration of the first dose of cells can reduce tumor burden in the subject, administration of the consecutive dose at a higher number of cells can avoid or minimize CRS and/or neurotoxicity in the subject after administration of the consecutive dose that can otherwise occur in subjects with morphological disease.

In some embodiments, prior to administration of the consecutive dose, the subject is one that exhibits non-morphological disease, such as molecularly detectable disease and/or minimal residual disease. In some embodiments, a subject can be assessed for tumor burden after administration of the first dose and prior to administration of the consecutive dose to confirm that tumor burden has been reduced compared to tumor burden present prior to treatment with the first dose. In some embodiments, if assessment of the subject indicates tumor burden is reduced and/or that the subject exhibits non-morphological disease, for example molecularly detectable disease and/or minimal residual disease, the provided methods include administering a consecutive dose of recombinant receptor-expressing (e.g., CAR-expressing) cells that is higher than the first or initial dose. In some embodiments, if assessment of the subject indicates tumor burden is not reduced and/or the subject exhibits morphological disease, the provided methods include administering a consecutive dose of recombinant receptor-expressing (e.g., CAR-expressing) cells that is the same as or less than the first or initial dose.

In some embodiments, the timing of the consecutive dose(s) in relation to the first and/or one another is designed to reduce the risk of unwanted toxic outcomes and promote maximum efficacy. In some embodiments, the consecutive dose, such as the same, lower or higher consecutive dose, is administered at a time at which disease burden remains reduced in the subject or reduced in subjects on average, such as based on clinical data, but at which the risk of CRS and/or neurotoxicity remain low. In some embodiments, methods are provided in which CRS and/or neurotoxicity in a subject can be prevented, minimized or reduced by first administering a low dose of CAR+ T cells to reduce disease or tumor burden to non-morphological disease, for example to achieve minimal residual disease or molecular detectable disease status, followed by administration of the consecutive dose of recombinant receptor-expressing (e.g., CAR-expressing) cells.

In some embodiments, a consecutive dose is generally given at a point in time relative to the first or previous dose at which the risk of a toxic outcome or symptom or biochemical indicator thereof—such as CRS or neurotoxicity, macrophage activation syndrome, or tumor lysis syndrome—is at or below an acceptable level. For example, the consecutive dose may be administered after a toxic outcome has peaked and is declining or has declined below an acceptable level following the initial dose. Thus, in some embodiments, the consecutive dose is administered at least 4, 5, 6, 7, 8, 9, 10, 11, 12, 13, 14, 15, 16, 17, 18, 19, 20, 21, 22, 23, 24, 25, 26, or 27 days following the initiation of the first or prior dose, or greater than about 14 or 15 days or 21 days following the initiation of the first or prior dose. In some embodiments, the appropriate timing is determined by monitoring and/or assessing the presence of one or more symptoms or outcomes associated with the toxic event and delivering the consecutive dose after determining that the symptom or outcome is at or below an acceptable level.

In some embodiments, the timing of the consecutive dose is such that it avoids a reduction in efficacy that may otherwise be induced upon administration of a subsequent dose by a host immune response that has been mounted following administration of a first dose. In some aspects, the consecutive dose is administered prior to the development of a host immune response, e.g., adaptive or specific, e.g., humoral or cell-mediated, immune response against the administered cells and/or recombinant receptor they express, and/or before such a response is detectable, e.g., by one or more specified detection methods. The consecutive dose or doses generally are administered at a time at which a host adaptive immune response against the cells is not detected, has not become established, and/or has not reached a certain level or degree or stage. In this regard, the methods are advantageous compared to providing subsequent doses at the time of relapse, which generally is after an anti-transgene response has developed. In some embodiments, the consecutive dose is administered before or within about 28 days or 35 days following the first or prior dose, or before about 24, 25, 26, or 27 days following the initiation of the first or prior dose.

Thus, the provided methods in some embodiments involve administering one or more consecutive doses after debulking or reducing disease burden with a first dose, after a window of risk for toxicity, but before the mounting of an immune response. In this environment and with the appropriate timing, the consecutive dose can safely and effectively provide immune surveillance, clearing or preventing expansion or metastasis of residual disease cells, whether measurable or not by standard or research grade analytical methods. Thus, in some embodiments, the consecutive dose is a disease-consolidating dose.

In particular embodiments, the first dose includes the cells in an amount sufficient to reduce burden of the disease or condition in the subject and the consecutive dose is administered a time at which a serum level of a factor indicative of cytokine-release syndrome (CRS) in the subject is no more than 10 or no more than 25 times the serum level of the indicator in the subject immediately prior to the administration of the first dose, and/or at a time after a CRS-related outcome in the subject has reached a peak level and begun to decline following administration of the first dose, and at which the subject does not exhibit a detectable adaptive host immune response specific for the recombinant receptor expressed by the cells of the first dose.

In particular embodiments, the first dose contains fewer than at or about $1 \times 10^6$ of the cells per kilogram body weight of the subject, fewer than at or about $1 \times 10^8$ of the cells, and/or fewer than at or about $1 \times 10^8$ of the cells/m$^2$ of the subject, and the consecutive dose is administered at a time point that is more than about 14 days after and less than about 28 days after initiation of the administration of the first dose. In some embodiments, the consecutive dose is administered at or about 14 days, 15 days, 16, days, 17 days, 18 days, 19 days, 20 days, 21 days, 22 days, 23 days, 24 days, 25 days, 26 days, 27 days, or 28 days following the first or prior dose. In particular embodiments, the consecutive dose is administered at about 17 days or at about 21 days following the first or prior dose.

Thus, the provided methods offer advantages over single-dose administrations, which can lead to severe toxicity, unwanted outcomes, and/or lower efficacy, particularly in the context of high disease burden. They also can be advantageous over methods administering subsequent dose (s) too soon following an initial dose—increasing the risk of unwanted side effects—or too late, e.g., after establishment of an immune response to a previous dose. The provided methods extend exposure to therapeutic cells, improving durability and extent of clinical response and/or patient survival, while reducing toxic outcomes. Also provided are compositions and articles of manufacture providing doses for use in such methods.

II. Administration of Cells in Adoptive Cell Therapy

The provided methods generally involve administering multiple doses of cells expressing recombinant receptors, such as CARs, or other antigen receptors, such as transgenic TCRs, to subjects having a disease or condition specifically recognized by the receptors. The administrations generally effect an improvement in one or more symptoms of the disease or condition and/or treat or prevent the disease or condition or symptom thereof.

As used herein, a "subject" is a mammal, such as a human or other animal, and typically is human. In some embodiments, the subject has been treated with a therapeutic agent targeting the disease or condition, e.g. the tumor, prior to administration of the first dose and/or prior to the administration of the consecutive dose. In some aspects, the subject is refractory or non-responsive to the other therapeutic agent.

In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

In some embodiments, the subject is responsive to the other therapeutic agent, and treatment with the therapeutic agent reduces disease burden. In some aspects, the subject is initially responsive to the therapeutic agent, but exhibits a relapse of the disease or condition over time. In some embodiments, the subject has not relapsed. In some such embodiments, the subject is determined to be at risk for relapse, such as at a high risk of relapse, and thus the cells are administered prophylactically, e.g., to reduce the likelihood of or prevent relapse.

In some aspects, the subject has not received prior treatment with another therapeutic agent. In some embodiments, the subject has not received a dose of cells expressing a CAR prior to the administration of the first dose and/or has not received a dose of cells expressing the CAR or other receptor expressed by such cells or expressing any recombinant receptor targeting the same molecule or antigen. In some aspects, the subject has not received a dose of cells expressing the CAR of the first dose prior to the administration of the first dose.

Among the diseases, conditions, and disorders are tumors, including solid tumors, hematologic malignancies, and melanomas, and including localized and metastatic tumors, infectious diseases, such as infection with a virus or other pathogen, e.g., HIV, HCV, HBV, CMV, and parasitic disease, and autoimmune and inflammatory diseases. In some embodiments, the disease or condition is a tumor, cancer, malignancy, neoplasm, or other proliferative disease or disorder. Such diseases include but are not limited to leukemia, lymphoma, e.g., chronic lymphocytic leukemia (CLL), acute-lymphoblastic leukemia (ALL), non-Hodgkin's lymphoma, acute myeloid leukemia, multiple myeloma, refractory follicular lymphoma, mantle cell lymphoma, indolent B cell lymphoma, B cell malignancies, cancers of the colon, lung, liver, breast, prostate, ovarian, skin, melanoma, bone, and brain cancer, ovarian cancer, epithelial cancers, renal cell carcinoma, pancreatic adenocarcinoma, Hodgkin lymphoma, cervical carcinoma, colorectal cancer, glioblastoma, neuroblastoma, Ewing sarcoma, medulloblastoma, osteosarcoma, synovial sarcoma, and/or mesothelioma. In some embodiments, the subject has acute-lymphoblastic leukemia (ALL). In some embodiments, the subject has non-Hodgkin's lymphoma.

In some embodiments, the size or timing of the doses is determined as a function of the particular disease or condition in the subject. It is within the level of a skilled artisan to empirically determine the size or timing of the doses for a particular disease in view of the provided description. In some cases, for example, subjects with non-Hodgkin's lymphoma (NHL) can be less responsive or only partially responsive to treatment with recombinant receptor-expressing cells (e.g., CAR-expressing cells, such as CAR-expressing T cells) than subjects with acute-lymphoblastic leukemia (ALL). In some cases, a lower dose of cells administered to a subject with NHL may not reduce tumor burden in a subject, thereby increasing the risk of toxic outcomes, such as CRS and/or neurotoxicity, in a subject when administered a consecutive dose. In some embodiments, methods are provided in which subjects with NHL are administered a consecutive dose that is the same or less than the dose of recombinant receptor-expressing (e.g., CAR-expressing) cells administered in the first dose, thereby minimizing or reducing risk of toxic side effects that can occur upon administration of the consecutive dose.

In some embodiments, the disease or condition is a tumor or a cancer and the subject has a large tumor burden prior to the administration of the first dose, such as a large solid tumor or a large number or bulk of disease-associated, e.g., tumor or cancer cells. In some aspects, the subject has a high number of metastases and/or widespread localization of metastases. In some aspects, the initial tumor burden in the subject is low and the subject has few metastases.

In some embodiments, the size or timing of the doses is determined by the initial disease burden, such as tumor burden, in the subject. For example, in some cases, whereas the subject generally is administered a relatively low number of cells in the first dose, in context of lower disease burden, such as molecular detectable disease and/or minimal residual disease, the initial dose may be higher. In other cases, in subjects exhibiting a higher disease burden after administration of the first dose, the consecutive dose may be the same as or lower than the first dose. In some embodiments, subjects are assessed for disease burden using methods as described herein, such as methods that assess blasts in bone marrow or molecular disease by flow cytometry or qPCR methods.

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the antigen associated with the disease or disorder is selected from the group consisting of orphan tyrosine kinase receptor ROR1, tEGFR, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, 0EPHa2, ErbB2, 3, or 4, FBP, fetal acethycholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, CS-1, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the populations of cells administered. In some embodiments, the provided methods involve administering the cells and/or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount. In the context of lower tumor burden, the prophylactically effective amount in some aspects will be higher than the therapeutically effective amount.

Methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

In some embodiments, the cell therapy, e.g., adoptive cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, and following isolation and processing are administered to the same subject.

In some embodiments, the cell therapy, e.g., adoptive cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

The cells can be administered by any suitable means, for example, by bolus infusion, by injection, e.g., intravenous or subcutaneous injections, intraocular injection, periocular injection, subretinal injection, intravitreal injection, transseptal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells. In some embodiments, it is administered by multiple bolus administrations of the cells, for example, over a period of no more than 3 days, or by continuous infusion administration of the cells.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agent includes a cytokine, such as IL-2, for example, to enhance persistence.

In some embodiments, the methods comprise administration of a chemotherapeutic agent, e.g., a conditioning chemotherapeutic agent, for example, to reduce tumor burden prior to the first or consecutive dose administrations.

Preconditioning subjects with immunodepleting (e.g., lymphodepleting) therapies can improve the effects of adoptive cell therapy (ACT). Preconditioning with lymphodepleting agents, including combinations of cyclosporine and fludarabine, have been effective in improving the efficacy of transferred tumor infiltrating lymphocyte (TIL) cells in cell therapy, including to improve response and/or persistence of the transferred cells. See, e.g., Dudley et al., 2002 *Science*, 298, 850-54; Rosenberg et al., *Clin Cancer Res* 2011, 17(13):4550-4557. Likewise, in the context of CAR+ T cells, several studies have incorporated lymphodepleting agents, most commonly cyclophosphamide, fludarabine, bendamustine, or combinations thereof, sometimes accompanied by low-dose irradiation. See Han et al. Journal of Hematology & Oncology 2013, 6:47; Kochenderfer et al., *Blood* 2012; 119: 2709-2720; Kalos et al., *Sci Transl Med* 2011, 3(95):95ra73; Clinical Trial Study Record Nos.: NCT02315612; NCT01822652. Such preconditioning can be carried out with the goal of reducing the risk of one or more of various outcomes that could dampen efficacy of the therapy. These include the phenomenon known as "cytokine sink," by which T cells, B cells, NK cells compete with TILs for homeostatic and activating cytokines, such as IL-2, IL-7, and/or IL-15; suppression of TILs by regulatory T cells, NK cells, or other cells of the immune system; impact of negative regulators in the tumor microenvironment. Muranski et al., *Nat Clin Pract Oncol.* 2006 December; 3(12): 668-681.

Thus, in some embodiments, the methods include administering a preconditioning agent, such as a lymphodepleting or chemotherapeutic agent, such as cyclophosphamide, fludarabine, or combinations thereof, to a subject prior to the first or subsequent dose. For example, the subject may be administered a preconditioning agent at least 2 days prior, such as at least 3, 4, 5, 6, or 7 days prior, to the first or subsequent dose. In some embodiments, the subject is administered a preconditioning agent no more than 7 days prior, such as no more than 6, 5, 4, 3, or 2 days prior, to the first or subsequent dose In some embodiments, where the lymphodepleting agent comprises cyclophosphamide, the subject is administered between or between about 0.5 g/m$^2$ and 5 g/m$^2$, such as between or between about 1 g/m$^2$ and 4 g/m$^2$, 1 g/m$^2$ and 3 g/m$^2$, or 2 g/m$^2$ and 4 g/m$^2$ of cyclophosphamide. In some aspects, the subject is administered 2 g/m$^2$ cyclophosphamide or about 2 g/m$^2$ cyclophosphamide. In some embodiments, the subject is preconditioned with cyclophosphamide at a dose between or between about 20 mg/kg and 100 mg/kg, such as between or between about 40 mg/kg and 80 mg/kg. In some aspects, the subject is preconditioned with or with about 60 mg/kg of cyclophosphamide.

In some embodiments, where the lymphodepleting agent comprises fludarabine, the subject is administered fludarabine at a dose between or between about 1 g/m$^2$ and 100 g/m$^2$, such as between or between about 10 g/m$^2$ and 75 g/m$^2$, 15 g/m$^2$ and 50 g/m$^2$, 20 g/m$^2$ and 30 g/m$^2$, or 24 g/m$^2$ and 26 g/m$^2$. In some instances, the subject is administered 25 g/m$^2$ of fludarabine. In some embodiments, the fludarabine can be administered in a single dose or can be administered in a plurality of doses, such as given daily, every other day or every three days. For example, in some instances, the agent, e.g., fludarabine, is administered between or between about 1 and 5 times, such as between or between about 3 and 5 times. In some embodiments, such plurality of doses is administered in the same day, such as 1 to 5 times or 3 to 5 times daily.

In some embodiments, the lymphodepleting agent comprises a combination of agents, such as a combination of cyclophosphamide and fludarabine. Thus, the combination of agents may include cyclophosphamide at any dose or administration schedule, such as those described above, and fludarabine at any dose or administration schedule, such as those described above. For example, in some aspects, the subject is administered 60 mg/kg (~2 g/m$^2$) of cyclophosphamide and 3 to 5 doses of 25 mg/m$^2$ fludarabine prior to the first or subsequent dose.

In some embodiments, the administration of the preconditioning agent prior to infusion of the first or subsequent dose improves an outcome of the treatment. For example, in some aspects, preconditioning improves the efficacy of treatment with the first or subsequent dose or increases the persistence of the recombinant receptor-expressing cells (e.g., CAR-expressing cells, such as CAR-expressing T cells) in the subject. In some embodiments, preconditioning treatment increases disease-free survival, such as the percent of subjects that are alive and exhibit no minimal residual or molecularly detectable disease after a given period of time following the first or subsequent dose. In some embodiments, the time to median disease-free survival is increased.

Once the cells are administered to the subject (e.g., human), the biological activity of the engineered cell populations in some aspects is measured by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells also can be measured by assaying expression and/or secretion of certain cytokines, such as CD 107a, IFNγ, IL-2, and TNF. In some aspects the biological activity is measured by assessing clinical outcome, such as reduction in tumor burden or load. In some aspects, toxic outcomes, persistence and/or expansion of the cells, and/or presence or absence of a host immune response, are assessed.

In certain embodiments, engineered cells are modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known in the art. See, for instance, Wadwa et al., J. Drug Targeting 3: 1 1 1 (1995), and U.S. Pat. No. 5,087,616.

III. Dosing

The timing and size of the multiple doses of cells generally are designed to reduce risk of or minimize toxic outcomes and/or to improve efficacy, such as by providing increased exposure of the subject to the cells, e.g., over time. The methods involve administering a first dose, generally followed by one or more consecutive doses, with particular time frames between the different doses.

In the context of adoptive cell therapy, administration of a given "dose" encompasses administration of the given amount or number of cells as a single composition and/or single uninterrupted administration, e.g., as a single injection or continuous infusion, and also encompasses administration of the given amount or number of cells as a split dose, provided in multiple individual compositions or infusions, over a specified period of time, which is no more than 3 days. Thus, in some contexts, the first or consecutive dose is a single or continuous administration of the specified number of cells, given or initiated at a single point in time. In some contexts, however, the first or consecutive dose is administered in multiple injections or infusions over a period of no more than three days, such as once a day for three days or for two days or by multiple infusions over a single day period.

Thus, in some aspects, the cells of the first dose are administered in a single pharmaceutical composition. In some embodiments, the cells of the consecutive dose are administered in a single pharmaceutical composition.

In some embodiments, the cells of the first dose are administered in a plurality of compositions, collectively containing the cells of the first dose. In some embodiments, the cells of the consecutive dose are administered in a plurality of compositions, collectively containing the cells of the consecutive dose. In some aspects, additional consecutive doses may be administered in a plurality of compositions over a period of no more than 3 days.

The term "split dose" refers to a dose that is split so that it is administered over more than one day. This type of dosing is encompassed by the present methods and is considered to be a single dose.

Thus, the first dose and/or consecutive dose(s) in some aspects may be administered as a split dose. For example, in some embodiments, the dose may be administered to the subject over 2 days or over 3 days. Exemplary methods for split dosing include administering 25% of the dose on the first day and administering the remaining 75% of the dose on the second day. In other embodiments, 33% of the first dose may be administered on the first day and the remaining 67% administered on the second day. In some aspects, 10% of the dose is administered on the first day, 30% of the dose is administered on the second day, and 60% of the dose is administered on the third day. In some embodiments, the split dose is not spread over more than 3 days.

With reference to a prior dose, such as a first dose, the term "consecutive dose" refers to a dose that is administered to the same subject after the prior, e.g., first, dose without any intervening doses having been administered to the subject in the interim. Nonetheless, the term does not encompass the second, third, and/or so forth, injection or infusion in a series of infusions or injections comprised within a single split dose. Thus, unless otherwise specified, a second infusion within a one, two or three-day period is not considered to be a "consecutive" dose as used herein. Likewise, a second, third, and so-forth in the series of multiple doses within a split dose also is not considered to be an "intervening" dose in the context of the meaning of "consecutive" dose. Thus, unless otherwise specified, a dose administered a certain period of time, greater than three days, after the initiation of a first or prior dose, is considered to be a "consecutive" dose even if the subject received a second or subsequent injection or infusion of the cells following the initiation of the first dose, so long as the second or subsequent injection or infusion occurred within the three-day period following the initiation of the first or prior dose.

Thus, unless otherwise specified, multiple administrations of the same cells over a period of up to 3 days is considered to be a single dose, and administration of cells within 3 days of an initial administration is not considered a consecutive dose and is not considered to be an intervening dose for purposes of determining whether a second dose is "consecutive" to the first.

In some embodiments, multiple consecutive doses are given, in some aspects using the same timing guidelines as those with respect to the timing between the first dose and first consecutive dose, e.g., by administering a first and multiple consecutive doses, with each consecutive dose given within a period of time that is greater than about 14 and less than about 28 days, e.g., about 21 days, after the administration of the first or immediately prior dose. The additional multiple additional consecutive dose or doses also are referred to as subsequent dose or subsequent consecutive dose.

As used herein, "first dose" is used to describe the timing of a given dose being prior to the administration of a consecutive or subsequent dose. The term does not necessarily imply that the subject has never before received a dose of cell therapy or even that the subject has not before received a dose of the same cells or cells expressing the same recombinant receptor or targeting the same antigen.

Dosage Amount or Size

The size of the first and/or one or more consecutive doses of cells are generally designed to provide improved efficacy and/or reduced risk of toxicity. In some embodiments, the number of cells in the first dose is between about $0.5 \times 10^6$ cells/kg body weight of the subject and $3 \times 10^6$ cells/kg, between about $0.75 \times 10^6$ cells/kg and $2.5 \times 10^6$ cells/kg or between about $1 \times 10^6$ cells/kg and $2 \times 10^6$ cells/kg, each inclusive.

In some embodiments, the first dose is a low dose. In particular embodiments, the first dose contains a number of cells, number of recombinant receptor (e.g., CAR)-expressing cells, number of T cells, or number of peripheral blood mononuclear cells (PBMCs) in the range from about $10^5$ to about $10^6$ of such cells per kilogram body weight of the subject, inclusive, and/or a number of such cells that is no more than about $10^5$ or about $10^6$ such cells per kilogram body weight of the subject, inclusive. For example, in some embodiments, the first dose includes less than or no more than at or about $1 \times 10^5$, at or about $2 \times 10^5$, at or about $5 \times 10^5$, or at or about $1 \times 10^6$ of such cells per kilogram body weight of the subject. In some embodiments, the first dose includes at or about $1 \times 10^5$, at or about $2 \times 10^5$, at or about $5 \times 10^5$, or at or about $1 \times 10^6$ of such cells per kilogram body weight of the subject, or a value within the range between any two of the foregoing values. In particular embodiments, the numbers and/or concentrations of cells refer to the number of recombinant receptor (e.g., CAR)-expressing cells. In other embodiments, the numbers and/or concentrations of cells refer to the number or concentration of all cells, T cells, or peripheral blood mononuclear cells (PBMCs) administered.

In some embodiments, for example, where the subject is a human, the first dose includes fewer than or equal to about $1 \times 10^8$ total recombinant receptor (e.g., CAR)-expressing cells, T cells, or peripheral blood mononuclear cells (PBMCs), e.g., in the range of about $1 \times 10^6$ to $1 \times 10^8$ such cells, inclusive, such as no more than $2 \times 10^6$, $5 \times 10^6$, $1 \times 10^7$, $5 \times 10^7$, or $1 \times 10^8$ or total such cells, or the range between any two of the foregoing values.

In some embodiments, the first dose contains fewer than or equal to about $1\times10^8$ total recombinant receptor (e.g., CAR)-expressing cells, T cells, or peripheral blood mononuclear cells (PBMCs) cells per $m^2$ of the subject, e.g., in the range of about $1\times10^6$ to $1\times10^8$ such cells per $m^2$ of the subject, inclusive, such as no more than $2\times10^6$, $5\times10^6$, $1\times10^7$, $5\times10^7$, or $1\times10^8$ such cells per $m^2$ of the subject, or the range between any two of the foregoing values.

In certain embodiments, for example, where risk of toxicity and/or disease burden in the subject is determined to be low, the first dose can be a relatively high dose, such as a dose that is greater than $1\times10^6$ cells/kg or that includes greater than $1\times10^8$ cells, such as T cells or PBMCs, or greater than $1\times10^8$ such cells per $m^2$ of the subject. In some embodiments, disease burden is low if the subject does not exhibit substantial morphologic disease or does not exhibit morphologic disease, or that exhibits less than 20% of blast cells in bone marrow, less than 15% of blast cells in bone marrow, less than 10% blast cells in bone marrow or less than 5% blast cells in bone marrow. In some embodiments, disease burden is low if the subject exhibits non-morphologic disease, such as exhibits minimal residual disease or molecularly detectable disease but does not exhibit the features associated with morphological disease as known in the art of described elsewhere, such as does not exhibit greater than 5% of blast cells in bone marrow. In some embodiments, the number of cells, recombinant receptor (e.g., CAR)-expressing cells, T cells, or peripheral blood mononuclear cells (PBMCs) in the first dose is greater than about $1\times10^6$ such cells per kilogram body weight of the subject, e.g., $2\times10^6$, $3\times10^6$, $5\times10^6$, $1\times10^7$, $5\times10^7$, $1\times10^8$, $1\times10^9$, or $1\times10^{10}$ such cells per kilogram of body weight and/or $1\times10^8$, $1\times10^9$, $1\times10^{10}$ such cells per $m^2$ of the subject or total, or the range between any two of the foregoing values.

In some embodiments, the number of cells administered in the consecutive dose is the same as or similar to the number of cells administered in the first dose in any of the embodiments herein, such as less than or no more than at or about $1\times10^5$, at or about $2\times10^5$, at or about $5\times10^5$, or at or about $1\times10^6$ of such cells per kilogram body weight of the subject. In some embodiments, the consecutive dose(s) contains at or about $1\times10^5$, at or about $2\times10^5$, at or about $5\times10^5$, or at or about $1\times10^6$ of such cells per kilogram body weight of the subject, or a value within the range between any two of the foregoing values.

In reference to cell numbers, in some embodiments, such values refer to numbers of recombinant receptor-expressing (e.g. CAR-expressing) cells; in other embodiments, they refer to number of T cells or PBMCs or total cells administered.

In some aspects, the consecutive dose is larger than the first dose. For example, in some embodiments, the consecutive dose contains more than about $1\times10^6$ cells, recombinant receptor (e.g. CAR)-expressing cells, T cells, and/or PBMCs per kilogram body weight of the subject, such as about or at least about $2\times10^6$, $3\times10^6$, $5\times10^6$, $1\times10^7$, $1\times10^8$, or $1\times10^9$ such cells per kilogram body weight of the subject. In some embodiments, the number of cells in the consecutive dose is between about $2\times10^6$ cells/kg body weight of the subject and $6\times10^6$ cells/kg, between about $2.5\times10^6$ cells/kg and $5.0\times10^6$ cells/kg, or between about $3.0\times10^6$ cells/kg and about $4.0\times10^6$ cells/kg, each inclusive. In some embodiments, the amount or size of the consecutive dose is sufficient to reduce disease burden or an indicator thereof, and/or one or more symptoms of the disease or condition. In some embodiments, the dose is of a size effective to improve survival of the subject, for example, to induce survival, relapse-free survival, or event-free survival of the subject for at least 6 months, or at least 1, 2, 3, 4, or 5 years. In some embodiments, the number of cells, recombinant receptor (e.g. CAR)-expressing cells, T cells, and/or PBMCs administered and/or number of such cells administered per body weight of the subject in the consecutive dose is at least 2-fold, 5-fold, 10-fold, 50-fold, or 100-fold or more greater than the number administered in the first dose. In some embodiments, disease burden, tumor size, tumor volume, tumor mass, and/or tumor load or bulk is reduced following the consecutive dose by at least at or about 50, 60, 70, 80, 90% or more compared to that immediately prior to the administration of the first dose or of the consecutive dose.

In other embodiments, the number of cells administered in the consecutive dose is lower than the number of cells administered in the first dose.

In some embodiments, multiple consecutive doses are administered following the first dose, such that an additional dose or doses are administered following administration of the consecutive dose. In some aspects, the number of cells administered to the subject in the additional dose or doses (i.e., the third, fourth, fifth, and so forth) is the same as or similar to the first dose and/or consecutive dose. In some embodiments, the additional dose or doses are larger than prior doses.

In some aspects, the size of the first and/or consecutive dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some aspects, the size of the first and/or consecutive dose is determined by the burden of the disease or condition in the subject. For example, in some aspects, the number of cells administered in the first dose is determined based on the tumor burden that is present in the subject immediately prior to administration of the first dose. In some embodiments, the size of the first and/or consecutive dose is inversely correlated with disease burden. In some aspects, as in the context of a large disease burden, the subject is administered a low number of cells, for example less than about $1\times10^6$ cells per kilogram of body weight of the subject. In other embodiments, as in the context of a lower disease burden, the subject is administered a larger number of cells, such as more than about $1\times10^6$ cells per kilogram body weight of the subject, for example more than about $2\times10^6$, $2.5\times10^6$ or $3\times10^6$ cells/kg.

In some aspects, the number of cells administered in the consecutive dose is determined based on the tumor burden that is present in the subject following administration of the first dose. In some embodiments, e.g. where the first dose results in reduced or decreased disease burden or has done so below a particular threshold amount or level, e.g., one above which there is an increased risk of toxic outcome, the consecutive dose is high or large, e.g. more than $1\times10^6$ cells (e.g., total cells, receptor-expressing cells, T cells, or PBMCs) per kilogram body weight, such as more than $2.0\times10^6$, $2.5\times10^6$ or $3.0\times10^6$ cells/kg, and/or is larger than the first dose. In some embodiments, a subject exhibits reduced or decreased disease burden if they exhibited morphological disease prior to treatment and exhibit complete remission (e.g., fewer than 5% blasts in bone marrow) with or without molecular disease (e.g., minimum residual disease (MRD) that is molecularly detectable, e.g., as detected by flow cytometry or quantitative PCR) after treatment. In some embodiments, a subject exhibits reduced or decreased disease burden if they exhibited molecular disease prior to treatment and do not exhibit molecular disease after treatment.

In other aspects, the number of cells administered in the consecutive dose is low, e.g. less than about $1\times10^6$, e.g. the same as or lower than the first dose, where the first dose has reduced tumor burden to a small extent or where the first dose has not led to a detectable reduction in tumor burden. In some cases, even if tumor burden is not reduced in a subject after receiving a first dose, a consecutive dose can be high or large, e.g. more than $1\times10^6$ cells (e.g., total cells, receptor-expressing cells, T cells, or PBMCs) per kilogram body weight, such as more than $2.0\times10^6$, $2.5\times10^6$ or $3.0\times10^6$ cells/kg, and/or is larger than the first dose.

In some embodiments, the first dose includes the cells in an amount that does not cause or reduces the likelihood of toxicity or toxic outcomes, such as cytokine release syndrome (CRS), severe CRS (sCRS), macrophage activation syndrome, tumor lysis syndrome, fever of at least at or about 38 degrees Celsius for three or more days and a plasma level of CRP of at least at or about 20 mg/dL, neurotoxicity and/or neurotoxicity. In some aspects, the number of cells administered in the first dose is determined based on the likelihood that the subject will exhibit toxicity or toxic outcomes, such as CRS, sCRS, and/or CRS-related outcomes following administration of the cells. For example, in some embodiments, the likelihood for the development of toxic outcomes in a subject is predicted based on tumor burden. In some embodiments, the methods include detecting or assessing the toxic outcome and/or disease burden prior to the administration of the dose.

In some aspects, the number of cells administered in the consecutive dose is determined based on the level of toxicity or toxic outcomes, e.g. CRS-related outcomes, following administration of the first dose. For example, in some embodiments, the number of cells administered in the consecutive dose is low, e.g. less than $1\times10^6$ cells per kilogram body weight, e.g. the same as or lower than the first dose, if the subject exhibits a detectable level of toxicity or toxic outcomes, e.g. CRS-related outcomes, following administration of the first dose.

In some embodiments, the subject is not administered the consecutive dose at a time following the first dose at which they exhibit toxicity or toxic outcomes, such as CRS-related outcomes, e.g. if a serum level of an indicator of CRS or other biochemical indicator of the toxicity is more than at or about 10 times, more than at or about 15 times, more than at or about 20 times, more than at or about 25 times, more than at or about 50 times, more than at or about 75 times, more than at or about 100 times, more than at or about 125 times, more than at or about 150 times, more than at or about 200 times, or more than at or about 250 times the baseline or pre-treatment level, such as the serum level of the indicator immediately prior to administration of the first dose.

In some embodiments, the subject is administered the consecutive dose, if and when, following the first dose, a biochemical indicator of or other indicator of a toxic outcome, e.g. a serum level of an indicator of CRS has not increased to above a given level, e.g., an acceptable level, such as more than at or about 10, 15, 20, 25, 50, 75, or 100 times the serum level of the indicator immediately prior to administration of the first dose, or has increased above an acceptable level but has declined to at or below the acceptable level. In some aspects, the consecutive dose is administered if and when the indicator declines below the acceptable level within 10, 11, 12, 13, 14, 15, 16, 17, 18, 19, 20, 21, 22, 23, 24, 25, 26, 27, 28, 29, 30, 31, 32, 33, 34, or 35 days, e.g., does so within 21 days, and/or within 15-27 days, within 21 days, within 28 days, or within 35 days, of the administration of the first dose, but is not administered if the level of the indicator does not decline below the acceptable level within that time period.

In some embodiments, the consecutive dose is administered if and when a clinical risk for developing cytokine-release syndrome (CRS), macrophage activation syndrome, or tumor lysis syndrome, or neurotoxicity is not present or has passed or has subsided following the first administration, such as after a critical window after which such events generally have subsided and/or are less likely to occur, e.g., in 60, 70, 80, 90, or 95% of subjects with a particular disease or condition.

In some embodiments, whether a consecutive dose is administered, when the consecutive dose is administered, and/or the number of the cells administered in the consecutive dose is or are determined based on the presence, absence, or degree of an immune response or detectable immune response in the subject to the cells of the first dose or recombinant receptor expressed thereby. In some aspects, a consecutive dose containing cells expressing the receptor of the cells of the first dose will not be administered to a subject with a detectable host adaptive immune response, or an immune response that has become established or reached a certain level, stage, or degree.

Timing of Doses

In some aspects, the timing of the consecutive dose is measured from the initiation of the first dose to the initiation of the consecutive dose. In other embodiments, the timing of the consecutive dose is measured from the completion of the first dose, or from the median day of administration of the first dose, e.g. in the context of split dosing, described herein, where a dose is administered over more than one day, e.g. over 2 days or over 3 days.

In some embodiments, the consecutive dose is administered at a time at which a serum level of a factor indicative of CRS in the subject is no more than 10 times, 25 times, 50 times, or 100 times the serum level of said indicator in the subject immediately prior to the administration of the first dose.

In some embodiments, the consecutive dose is administered at a time after a CRS-related outcome, such as a serum factor associated with or indicative of CRS, or a clinical sign or symptom thereof such as fever, hypoxia, hypotension, or neurological disturbance, in the subject has reached a peak level and begun to decline following administration of the first dose. In some embodiments, the consecutive dose is administered at a time after which the outcome is observed to be on the decline compared with the highest level of such outcome measured following the administration, or at a time at which or after which the level is on the decline following the maximum value or level of the outcome reached after the administration.

In some embodiments, the consecutive dose is administered when the level of an indicator of a toxic outcome, such as a serum indicator of CRS, declines below 25 times the level of the indicator immediately prior to the first dose. In some aspects, the consecutive dose is administered at a time at which the subject does not exhibit CRS or does not exhibit severe CRS.

In some aspects, the consecutive dose is administered at a point in time at which the disease burden in the patient has decreased as compared to the disease burden immediately prior to administration of the first dose. In some embodiments, a subject exhibits reduced or decreased disease burden if they exhibited morphological disease prior to treatment and exhibit complete remission (e.g., fewer than 5% blasts in bone marrow) with or without molecular disease (e.g., minimum residual disease (MRD) that is molecularly detectable, e.g., as detected by flow cytometry or quantitative PCR) after treatment. In some embodiments, a subject exhibits reduced or decreased disease burden if they exhibited molecular disease prior to treatment and do not exhibit molecular disease after treatment. In some embodiments, the consecutive dose is administered at a time at which the disease burden or indicator thereof such as bulk or number or percentage of disease (e.g., tumor) cells in the blood, other fluid, organ or tissue of the subject, or size of the tumor, has decreased by 10, 20, 30, 40, 50, 60, 70, 80, or 90% or more following administration of the first dose.

In some embodiments, the consecutive dose is administered at a point in time at which the disease or condition in the subject has not relapsed following the reduction in response to the first or prior dose. In some embodiments, the disease burden reduction is indicated by a reduction in one or more factors, such as load or number of disease cells in the subject or fluid or organ or tissue thereof, the mass or volume of a tumor, or the degree or extent of metastases. Such a factor is deemed to have relapsed if after reduction in the factor in response to an initial treatment or administration, the factor subsequently increases. In some embodiments, the relapse is in one or one or more factors, or in the disease burden generally. In some aspects, the consecutive dose is administered at a point in time at which the subject, disease burden, or factor thereof has relapsed as compared to the lowest point measured or reached following the first or prior administration, but still is lower compared to the time immediately prior to the first dose. In some embodiments, the subject is administered the consecutive dose at a point in time at which disease burden or factor indicative thereof has not changed, e.g. at a time when an increase in disease burden has been prevented.

In some embodiments, the consecutive dose is administered at a time when a host adaptive immune response is not detected, has not become established, or has not reached a certain level, degree, or stage. In some aspects, the consecutive dose is administered prior to the development of a memory immune response in the subject.

In some aspects, the time between the administration of the first dose and the administration of the consecutive dose is about 9 to about 35 days, about 14 to about 28 days, or 15 to 27 days. In some embodiments, the administration of the consecutive dose is at a time point more than about 14 days after and less than about 28 days after the administration of the first dose. In some embodiments, the administration of the consecutive dose is no more than about 14 days, 15 days, 16 days, 17 days, 18 days, 19 days, 20 days, 21 days, 22 days, 23 days, 24 days, 25 days, 26 days, 27 days or 28 days after the administration of the first dose. In some aspects, the time between the first and consecutive dose is about 14 days about 17 days or about 21 days.

In some embodiments, an additional or subsequent dose or doses, e.g. further consecutive doses, are administered following administration of the consecutive dose. In some aspects, the additional consecutive dose or doses are administered at least about 14 and less than about 28 days following administration of a prior dose, such as a prior consecutive dose. In some embodiments, an exemplary dosage regime includes a schedule of administration of recombinant receptor-expressing cells (e.g., CAR-expressing cells, such as CAR-expressing T cells) at or about In some embodiments, the additional dose is administered less than about 14 days following the prior dose, for example, less than 4, 5, 6, 7, 8, 9, 10, 11, 12, or 13 days after the prior dose. In some embodiments, no dose is administered less than about 14 days following the prior dose and/or no dose is administered more than about 28 days after the prior dose.

In any of the embodiments, the methods in some cases include the administration of the first or prior dose and the consecutive dose(s), and in other cases include the administration of the consecutive dose(s) to a subject who has previously received the first or prior dose but do not include the administration of the first or prior dose itself. Thus, the methods in some cases involve the administration of consolidating treatment, such as by administering a consolidating consecutive dose to a subject that has previously received a dose, e.g., a debulking dose, of recombinant receptor-expressing, e.g., CAR-expressing, cells. In some aspects, the previous dose of receptor-expressing, e.g., CAR-expressing, cells has been sufficient to reduce the burden of the disease or condition in the subject such that the efficacy and/or safety of the administration of the cells in the consecutive dose is improved relative to administering the dose without the subject having received the first dose.

In some embodiments, disease burden, tumor size, tumor volume, tumor mass, and/or tumor load or bulk is reduced following the consecutive dose by at least at or about 50, 60, 70, 80, 90% or more compared to that immediately prior to the administration of the first dose or of the consecutive dose.

IV. Toxicity and Toxic Outcomes

In some embodiments, the timing or amount of the doses reduces or prevents toxicity or an outcome or symptom thereof, for example, compared to administration of the same or similar total number of cells as a single-dose, administration of the consecutive dose without the subject having previously received the first dose, administration of the consecutive dose at a different time relative to the first dose, and/or administration of different amount(s) in one or more of the doses.

Administration of adoptive T cell therapy, such as treatment with T cells expressing chimeric antigen receptors, can induce toxic effects or outcomes such as cytokine release syndrome and neurotoxicity. In some examples, such effects or outcomes parallel high levels of circulating cytokines, which may underlie the observed toxicity.

In some embodiments, the provided methods are designed to or include features that result in a lower degree of toxicity, toxic outcome or symptom, toxicity-promoting profile, factor, or property, such as a symptom or outcome associated with or indicative of cytokine release syndrome (CRS), for example, compared to administration of the same or similar total number of cells as a single-dose, administration of the consecutive dose without the subject having previously received the first dose, administration of the consecutive dose at a different time relative to the first dose, and/or administration of different amount(s) in one or more of the doses.

In some aspects, the toxic outcome is or is associated with or indicative of cytokine release syndrome (CRS) or severe CRS (sCRS). CRS, e.g., sCRS, can occur in some cases following adoptive T cell therapy and administration to subjects of other biological products. See Davila et al., Sci Transl Med 6, 224ra25 (2014); Brentjens et al., Sci. Transl. Med. 5, 177ra38 (2013); Grupp et al., N. Engl. J. Med. 368, 1509-1518 (2013); and Kochenderfer et al., Blood 119, 2709-2720 (2012); Xu et al., Cancer Letters 343 (2014) 172-78.

Typically, CRS is caused by an exaggerated systemic immune response mediated by, for example, T cells, B cells, NK cells, monocytes, and/or macrophages. Such cells may release a large amount of inflammatory mediators such as cytokines and chemokines. Cytokines may trigger an acute inflammatory response and/or induce endothelial organ damage, which may result in microvascular leakage, heart failure, or death. Severe, life-threatening CRS can lead to pulmonary infiltration and lung injury, renal failure, or disseminated intravascular coagulation. Other severe, life-threatening toxicities can include cardiac toxicity, respiratory distress, neurologic toxicity and/or hepatic failure.

CRS may be treated using anti-inflammatory therapy such as an anti-IL-6 therapy, e.g., anti-IL-6 antibody, e.g., tocilizumab, or antibiotics. In some embodiments, the subject is treated with such a therapy following the first administration and the consecutive dose is administered only if and when the CRS-associated symptom(s) are reduced or declining or declined below an acceptable level following such treatment.

Outcomes, signs and symptoms of CRS are known and include those described herein. In some embodiments, where a particular dosage regimen or administration effects or does not effect a given CRS-associated outcome, sign, or symptom, particular outcomes, signs, and symptoms and/or quantities or degrees thereof may be specified.

In the context of administering CAR-expressing cells, CRS typically occurs 6-20 days after infusion of cells that express a CAR. See Xu et al., Cancer Letters 343 (2014) 172-78. In some cases, CRS occurs less than 6 days or more than 20 days after CAR T cell infusion. The incidence and timing of CRS may be related to baseline cytokine levels or tumor burden at the time of infusion. Commonly, CRS involves elevated serum levels of interferon (IFN)-γ, tumor necrosis factor (TNF)-α, and/or interleukin (IL)-2. Other cytokines that may be rapidly induced in CRS are IL-1β, IL-6, IL-8, and IL-10.

In some aspects, a lower degree of toxicity, outcome, symptom, profile, factor, or property is observed in the subjects to which the cells are administered by the dosing regimen of the present methods, for example, as compared to administration of the same or similar total number of cells as a single-dose, administration of the consecutive dose without the subject having previously received the first dose, administration of the consecutive dose at a different time relative to the first dose, and/or administration of different amount(s) in one or more of the doses. For example, in some embodiments, following administration of the first dose to the subject, the subject exhibits a lower degree of a CRS-related outcome, and/or exhibits a lower serum level of an inflammatory cytokine or factor indicative of CRS, as compared to administration of a larger number of cells to the subject. In some embodiments, following administration to the subject of the consecutive dose, the subject exhibits a lower degree of a CRS-related outcome, and/or exhibits a lower serum level of an inflammatory cytokine or outcome indicative of CRS, as compared to administration of the consecutive dose to the subject without the subject having received the first dose, or as compared to administering the first and consecutive dose(s) as a single dose, or as compared to administering the consecutive dose at a time that is earlier than or after the specified time period. In some embodiments, the subject does not exhibit CRS or severe CRS following administration of the first dose and/or following administration of the consecutive dose.

Exemplary outcomes associated with CRS include fever, rigors, chills, hypotension, dyspnea, acute respiratory distress syndrome (ARDS), encephalopathy, ALT/AST elevation, renal failure, cardiac disorders, hypoxia, neurologic disturbances, and death. Neurological complications include delirium, seizure-like activity, confusion, word-finding difficulty, aphasia, and/or becoming obtunded. Other CRS-related outcomes include fatigue, nausea, headache, seizure, tachycardia, myalgias, rash, acute vascular leak syndrome, liver function impairment, and renal failure. In some aspects, CRS is associated with an increase in one or more factors such as serum-ferritin, d-dimer, aminotransferases, lactate dehydrogenase and triglycerides, or with hypofibrinogenemia or hepatosplenomegaly.

In some embodiments, outcomes associated with CRS include one or more of: persistent fever, e.g., fever of a specified temperature, e.g., greater than at or about 38 degrees Celsius, for two or more, e.g., three or more, e.g., four or more days or for at least three consecutive days; fever greater than at or about 38 degrees Celsius; elevation of cytokines, such as a max fold change, e.g., of at least at or about 75, compared to pre-treatment levels of at least two cytokines (e.g., at least two of the group consisting of interferon gamma (IFNγ), GM-CSF, IL-6, IL-10, Flt-3L, fracktalkine, and IL-5, and/or tumor necrosis factor alpha (TNFα)), or a max fold change, e.g., of at least at or about 250 of at least one of such cytokines; and/or at least one clinical sign of toxicity, such as hypotension (e.g., as measured by at least one intravenous vasoactive pressor); hypoxia (e.g., plasma oxygen ($PO_2$) levels of less than at or about 90%); and/or one or more neurologic disorders (including mental status changes, obtundation, and seizures).

Exemplary CRS-related outcomes include increased or high serum levels of one or more factors, including cytokines and chemokines and other factors associated with CRS. Exemplary outcomes further include increases in synthesis or secretion of one or more of such factors. Such synthesis or secretion can be by the T cell or a cell that interacts with the T cell, such as an innate immune cell or B cell.

In some embodiments, the CRS-associated serum factors or CRS-related outcomes include inflammatory cytokines and/or chemokines, including interferon gamma (IFN-γ), TNF-a, IL-1β, IL-2, IL-6, IL-7, IL-8, IL-10, IL-12, sIL-2Ra, granulocyte macrophage colony stimulating factor (GM-CSF), macrophage inflammatory protein (MIP)-1, tumor necrosis factor alpha (TNFα), IL-6, and IL-10, IL-1β, IL-8, IL-2, MIP-1, Flt-3L, fracktalkine, and/or IL-5. In some embodiments, the factor or outcome includes C reactive protein (CRP). In addition to being an early and easily measurable risk factor for CRS, CRP also is a marker for cell expansion. In some embodiments, subjects that are measured to have high levels of CRP, such as ≥15 mg/dL, have CRS. In some embodiments, subjects that are measured to have high levels of CRP do not have CRS. In some embodiments, a measure of CRS includes a measure of CRP and another factor indicative of CRS.

In some embodiments, one or more inflammatory cytokines or chemokines are monitored before, during, or after CAR treatment. In some aspects, the one or more cytokines or chemokines include IFN-γ, TNF-α, IL-2, IL-1β, IL-6, IL-7, IL-8, IL-10, IL-12, sIL-2Rα, granulocyte macrophage colony stimulating factor (GM-CSF), or macrophage inflammatory protein (MIP). In some embodiments, IFN-γ, TNF-α, and IL-6 are monitored.

CRS criteria that appear to correlate with the onset of CRS to predict which patients are more likely to be at risk for developing sCRS have been developed (see Davilla et al. Science translational medicine. 2014; 6(224):224ra25). Factors include fevers, hypoxia, hypotension, neurologic changes, elevated serum levels of inflammatory cytokines, such as a set of seven cytokines (IFNγ, IL-5, IL-6, IL-10, Flt-3L, fractalkine, and GM-CSF) whose treatment-induced elevation can correlate well with both pretreatment tumor burden and sCRS symptoms. Other guidelines on the diagnosis and management of CRS are known (see e.g., Lee et al, Blood. 2014; 124(2):188-95). In some embodiments, the criteria reflective of CRS grade are those detailed in Table 1 below.

TABLE 1

Exemplary Grading Criteria for CRS

| Grade | Description of Symptoms |
| --- | --- |
| 1<br>Mild | Not life-threatening, require only symptomatic treatment such as antipyretics and anti-emetics (e.g., fever, nausea, fatigue, headache, myalgias, malaise) |
| 2<br>Moderate | Require and respond to moderate intervention:<br>    Oxygen requirement < 40%, or<br>    Hypotension responsive to fluids or low dose of a single vasopressor, or<br>    Grade 2 organ toxicity (by CTCAE v4.0) |
| 3<br>Severe | Require and respond to aggressive intervention:<br>    Oxygen requirement ≥ 40%, or<br>    Hypotension requiring high dose of a single vasopressor (e.g., norepinephrine ≥ 20 μg/kg/min, dopamine ≥ 10 μg/kg/min, phenylephrine ≥ 200 μg/kg/min, or epinephrine ≥ 10 μg/kg/min), or<br>    Hypotension requiring multiple vasopressors (e.g., vasopressin + one of the above agents, or combination vasopressors equivalent to ≥20 μg/kg/min norepinephrine), or<br>    Grade 3 organ toxicity or Grade 4 transaminitis (by CTCAE v4.0) |
| 4<br>Life-threatening | Life-threatening:<br>    Requirement for ventilator support, or<br>    Grade 4 organ toxicity (excluding transaminitis) |
| 5<br>Fatal | Death |

As used herein, a subject is deemed to develop "severe CRS" ("sCRS") in response to or secondary to administration of a cell therapy or dose of cells thereof, if, following administration, the subject displays: (1) fever of at least 38 degrees Celsius for at least three days; (2) cytokine elevation that includes either (a) a max fold change of at least 75 for at least two of the following group of seven cytokines compared to the level immediately following the administration: interferon gamma (IFNγ), GM-CSF, IL-6, IL-10, Flt-3L, fracktalkine, and IL-5 and/or (b) a max fold change of at least 250 for at least one of the following group of seven cytokines compared to the level immediately following the administration: interferon gamma (IFNγ), GM-CSF, IL-6, IL-10, Flt-3L, fracktalkine, and IL-5; and (c) at least one clinical sign of toxicity such as hypotension (requiring at least one intravenous vasoactive pressor) or hypoxia ($PO_2$<90%) or one or more neurologic disorder(s) (including mental status changes, obtundation, and/or seizures). In some embodiments, severe CRS includes CRS with a grade of 3 or greater, such as set forth in Table 1.

In some embodiments, the CRS encompasses a combination of (1) persistent fever (fever of at least 38 degrees Celsius for at least three days) and (2) a serum level of CRP of at least at or about 20 mg/dL.

In some embodiments, the CRS encompasses hypotension requiring the use of two or more vasopressors or respiratory failure requiring mechanical ventilation.

The method of measuring or detecting the various outcomes may be specified.

In some aspects, prior to the administration of the first dose, subsequent to the administration of the first dose and before administration of the consecutive dose, or subsequent to the administration of the consecutive dose, a CRS-associated outcome is assessed in the subject. In some embodiments, the level of the toxic outcome, e.g. the CRS-related outcome, e.g. the serum level of an indicator of CRS, is measured by ELISA. In some embodiments, fever and/or levels of CRP can be measured. In some embodiments, subjects with a fever and a CRP≥15 mg/dL may be considered high-risk for developing severe CRS.

In some embodiments, the toxic outcome, toxicity, or symptom is measured at a specified time point following administration. In some embodiments, the toxic outcome, e.g. CRS, severe CRS, and/or the CRS-associated outcome or serum level, or the lower degree of the outcome or serum level, is measured at 24 hours, at day 1, 2, 3, 4, 5, 6, 7, 8, 9, 10, 11, 12, 13, 14, 15, 16, 17, 18, 19, 20, or 21 following the administration, or over a period of 1, 2, 3, 4, 5, 6, 7, 8, 9, 10, 11, 12, 13, 14, 15, 16, 17, 18, 19, 20, or 21 days. In some embodiments, CRP is measured at day 3, 4, 5, 6, 7, 8, or 9. In some embodiments, the fold change in a factor or multiple factors, such as a cytokine(s), is measured as fold change between the level prior to treatment and at day 2, 3, 4, 5, 6, 7, 14, or 20 or 21, following treatment.

In some embodiments, at the time of the administration of the consecutive dose, the level of the CRS-related outcome is no more than 50% of the peak level, is no more than 40% of the peak level, is no more than 30% of the peak level, is no more than 20% of the peak level, is no more than 15% of the peak level, is no more than 10% of the peak level, is no more than 5% of the peak level, or is at or about or below the level immediately prior to the administration of the first dose and/or is at or about or below baseline.

In some aspects, at the time of the administration of the consecutive dose, the level of the CRS-related outcome is no more than ten times the level immediately prior to the administration of the first dose.

In some embodiments, the CRS-related outcome in the subject at day 2, 3, 4, 5, 6, 7, 8, 9, 10, 11, 12, 13, or 14 following the administration of the consecutive dose is not detectable or is reduced as compared to a method where the subject is administered the consecutive dose without having been administered the first dose and/or a method in which the cells of the first and second doses are administered in a single dose, and/or a method in which the consecutive dose is given at a time which is earlier than the time between the first and consecutive doses specified by the method.

In some embodiments, the CRS-related outcome in the subject at day 2, 3, 4, 5, 6, 7, 8, 9, 10, 11, 12, 13, or 14 following the administration of the first dose is not detectable or is reduced as compared to that following administration to the subject a dose of 2-fold, 5-fold, 10-fold, or 100-fold the number of cells, T cells, cells expressing the recombinant receptor, or PBMCs.

In some embodiments, the area under the curve (AUC) for a CRS-related outcome or serum level of a factor indicative of CRS over time in the subject following administration of the consecutive dose is lower as compared to that of a method where the subject is administered the consecutive dose without having been administered the first dose, and/or a method in which the cells of the first and consecutive doses are administered in a single dose, and/or a method in which the consecutive dose is given at a time which is earlier than the time between the first and consecutive doses specified by the method.

In some embodiments, the area under the curve (AUC) for a CRS-related outcome or serum level of a factor indicative of CRS over time in the subject following administration of the first dose is lower as compared to that following administration to the subject dose of 2-fold, 5-fold, 10-fold, or 100-fold the number of cells, T cells, cells expressing the recombinant receptor, or PBMCs.

In some aspects, the toxic outcome is or is associated with neurotoxicity. In some embodiments, symptoms associated with a clinical risk of neurotoxicity include confusion, delirium, expressive aphasia, obtundation, myoclonus, lethargy, altered mental status, convulsions, seizure-like activity, seizures (optionally as confirmed by electroencephalogram [EEG]), elevated levels of beta amyloid (Aβ), elevated levels of glutamate, and elevated levels of oxygen radicals. In some embodiments, neurotoxicity is graded based on severity (e.g., using a Grade 1-5 scale (see, e.g., Guido Cavaletti & Paola Marmiroli Nature Reviews Neurology 6, 657-666 (December 2010); National Cancer Institute—Common Toxicity Criteria version 4.03 (NCI-CTCAE v4.03).

In some instances, neurologic symptoms may be the earliest symptoms of sCRS. In some embodiments, neurologic symptoms are seen to begin 5 to 7 days after cell therapy infusion. In some embodiments, duration of neurologic changes may range from 3 to 19 days. In some cases, recovery of neurologic changes occurs after other symptoms of sCRS have resolved. In some embodiments, time or degree of resolution of neurologic changes is not hastened by treatment with anti-IL-6 and/or steroid(s).

As used herein, a subject is deemed to develop "severe neurotoxicity" in response to or secondary to administration of a cell therapy or dose of cells thereof, if, following administration, the subject displays symptoms that limit self-care (e.g. bathing, dressing and undressing, feeding, using the toilet, taking medications) from among: 1) symptoms of peripheral motor neuropathy, including inflammation or degeneration of the peripheral motor nerves; 2) symptoms of peripheral sensory neuropathy, including inflammation or degeneration of the peripheral sensory nerves, dysesthesia, such as distortion of sensory perception, resulting in an abnormal and unpleasant sensation, neuralgia, such as intense painful sensation along a nerve or a group of nerves, and/or paresthesia, such as functional disturbances of sensory neurons resulting in abnormal cutaneous sensations of tingling, numbness, pressure, cold and warmth in the absence of stimulus. In some embodiments, severe neurotoxicity includes neurotoxicity with a grade of 3 or greater, such as set forth in Table 2.

TABLE 2

Exemplary Grading Criteria for neurotoxicity

| Grade | Description of Symptoms |
| --- | --- |
| 1 Asymptomatic or Mild | Mild or asymptomatic symptoms |
| 2 Moderate | Presence of symptoms that limit instrumental activities of daily living (ADL), such as preparing meals, shopping for groceries or clothes, using the telephone, managing money |

TABLE 2-continued

Exemplary Grading Criteria for neurotoxicity

| Grade | Description of Symptoms |
| --- | --- |
| 3 Severe | Presence of symptoms that limit self-care ADL, such as bathing, dressing and undressing, feeding self, using the toilet, taking medications |
| 4 Life-threatening | Symptoms that are life-threatening, requiring urgent intervention |
| 5 Fatal | Death |

In some embodiments, the methods reduce symptoms associated with neurotoxicity compared to other methods. For example, subjects treated according to the present methods may have reduced symptoms of neurotoxicity, such as limb weakness or numbness, loss of memory, vision, and/or intellect, uncontrollable obsessive and/or compulsive behaviors, delusions, headache, cognitive and behavioral problems including loss of motor control, cognitive deterioration, and autonomic nervous system dysfunction, and sexual dysfunction, compared to subjects treated by other methods. In some embodiments, subjects treated according to the present methods may have reduced symptoms associated with peripheral motor neuropathy, peripheral sensory neuropathy, dysesthesia, neuralgia or paresthesia.

In some embodiments, the methods reduce outcomes associated with neurotoxicity including damages to the nervous system and/or brain, such as the death of neurons. In some aspects, the methods reduce the level of factors associated with neurotoxicity such as beta amyloid (Aβ), glutamate, and oxygen radicals.

In some embodiments, subjects administered the consecutive dose following the first dose have reduced symptoms, outcomes, or factors associated with neurotoxicity compared to administration of the consecutive dose in the absence of the first dose, administration of the cells of the first and second doses in a single dose, and/or administration of the consecutive dose at a time which is earlier than the time between the first and consecutive doses specified by the method.

V. Host Immune Responses to Transferred Cells

In some embodiments, one or more of the doses, e.g., the consecutive dose(s), is administered at a time at which an immune response, e.g., an adaptive or specific immune response to the transgenic receptor or cells, in the subject is not present, not detectable, or not detectable above a certain level. The presence or degree of a specific immune response to the transgene generally is related to the immunogenicity of the receptor, e.g., the CAR or transgenic TCR, expressed by the cells, and/or the time during which the subject has been exposed to the cells. For example, in some embodiments, an immune response, e.g., a specific humoral and/or cell-mediated immune response against the receptor, is not detected before 28 days, 35 days, or 42 days following the first exposure of the subject to the cells expressing the receptor. Thus, in some embodiments, the consecutive dose is administered before an immune response, an adaptive or specific immune response, a detectable immune response, and/or a memory response against the recombinant receptor or cells has developed in the subject. In this regard, the ability of cells of the consecutive dose to expand and/or persist in the subject is improved in comparison to other methods in which a consecutive dose is given at a later time point in comparison with the prior or first dose.

The methods may involve the detection of the presence or absence or level of such an immune response or indicator thereof, for example, following the administration of a first or consecutive dose and before the administration of the consecutive or next consecutive dose.

In some embodiments, the decision of when and/or whether to administer the consecutive dose depends on whether the subject exhibits such an immune response or detectable readout thereof, e.g., a detectable specific or adaptive host immune response specific for the cells or recombinant receptor, e.g., CAR, expressed by the cells of the first dose, and/or whether such a response is detected above a certain level. In some embodiments, where such a response is detected, the subject is not administered the consecutive dose.

In general, the consecutive dose is administered at a time at which the subject does not exhibit a specific or adaptive, e.g., humoral or cell-mediated, immune response against the receptor, e.g., CAR, expressed by the cells of the first dose, or does not exhibit such a response or indicator thereof at a detectable level or above an acceptable level. In some aspects, at the time of administration of the consecutive dose, the subject exhibits a reduced humoral or cell-mediated immune response against the CAR expressed by the cells of the first dose as compared to when an initial dose is larger.

In some embodiments, the host immune response is or comprises a humoral immune response. The humoral immune response may be indicated by the presence of antibodies specific for the cells or receptors expressed thereby in the serum, other bodily fluid, and/or organ or tissue of the subject. In some embodiments, such antibodies of a particular isotype are present, such as IgM or IgG, e.g., IgG1, IgG2, IgG3, and/or IgG4; in some embodiments they include IgE.

In some embodiments, the immune response is or comprises a cell-mediated component. A cell-mediated response may be indicated by the presence of cells, e.g., T cells, e.g., helper or cytotoxic T cells, that specifically recognize one or more epitopes of the recombinant receptor or cells via a T cell receptor.

In some embodiments the immune response is a primary immune response; in some aspects, the immune response is a memory response.

In some of any of the above embodiments, a detectable immune response refers to an amount detectable by any of a number of known methods for assessing specific immune responses to particular antigens and cells. For example, in some embodiments, the immune response of the specified type is detectable by performing ELISpot, ELISAs, or cell-based antibody detection methods, for example, by flow cytometry, on serum from the subject to detect the presence of antibodies that specifically bind to and/or neutralize antigens present on the cells, e.g., binding to epitopes of the recombinant receptor, e.g., CAR. In some such assays, isotype of the detected antibody is determined and may indicate the type of response and/or whether the response is a memory response.

In some embodiments, the specified immune response is detectable by cytotoxic T-lymphocyte (CTL) assays for detection of CD8$^+$ T cells that specifically bind to and induce cytotoxicity in response to epitopes in the recombinant receptor, and/or a mixed lymphocyte reaction, using cells, e.g., irradiated cells, expressing the recombinant receptor, as stimulator cells.

In some aspects, the detectable immune response is one that is detected by such a method above or significantly above the level of a control sample, such as a non-coated well or well coated with a control peptide or cells not expressing the recombinant receptor and/or levels detected based on pre-treatment serum or blood sample from the subject prior to treatment with the cells expressing the recombinant receptors.

In some aspects, the presence or absence of such a host immune response and/or quantity, degree, or extent thereof, is detected or measured, for example, following the administration of the first dose or consecutive dose.

Humoral immune responses may be detected by any of a number of well-known assays for detection of antibodies specific for particular antigens or cells, including binding assays, immunoassays, and cell-based assays. The assays may include those designed to assess the presence or absence of particular functions of the antibodies, such as their ability to carry out a particular effector function upon binding to the antigen, such as neutralizing antibody assays. In some embodiments, outcomes of humoral immune responses, such as antigen-specific antibodies, e.g., neutralizing antibodies, are detected using cell-based assays, e.g., by incubating pre- and post-treatment cells from the subject with cells expressing the recombinant receptor (and control cells) and detecting antigen-specific binding and/or other outcomes, such as neutralizing outcomes, e.g., by flow cytometry or enzymatic assays. In some embodiments, ELISA, and/or ELISpot assays are used to detect and quantify antibodies specific for the recombinant receptors, such as CARs, and epitopes mapped using known techniques, such as those using individual peptides representing portions of the receptor. See, e.g., Jensen et al. *Biol Blood Marrow Transplant.* 2010 September; 16(9): 1245-1256. In some embodiments, isotype of the detected antibodies are assessed, for example by using detection antibodies specific for particular isotypes, e.g., human isotypes.

Cellular or cell-based immune response to the cells and/or receptors may be detected and/or measured using any of a number of well-known techniques. Such techniques may include cytotoxic T-lymphocyte (CTL) assays for detection of CD8$^+$ T cells that specifically bind to and induce cytotoxicity in response to epitopes in the recombinant receptor, e.g., CAR, and/or cells administered. In some embodiments, the assay is a mixed lymphocyte reaction, such as those using PBMCs or other host-derived cells from blood or other organ or tissue as responder cells, and cells induced to express the recombinant receptor, e.g., irradiated T cells expressing the CAR, as stimulator cells. The stimulator cells generally are autologous and may be the same cells administered to the subject, and may be irradiated. Non-transduced cells or cells not expressing the transgene of interest may be used as negative controls in place of the stimulator cells in control samples. Likewise, responder cell samples from pre-treatment time points or other subjects may be used in control samples. In some aspects, such assays assess the ability of host cells to carry out one or more effector functions, e.g., antigen-specific cell lysis, e.g., using a chromium release assay to detect cytotoxic T cells present in the subject which specifically recognize antigens present on or in the administered cells and induce a cytotoxic response. In some embodiments, peripheral blood cells, e.g., PBMCs, are obtained from a subject before and after administration of the cells, and each used in an assay, such as a cell lysis assay, using autologous T cells modified to express the recombinant receptor, which generally are irradiated. Specific lysis indicates the presence of receptor-specific cell-mediated immune response. Epitope mapping may be carried out using panels of peptides representing portions of the recombinant receptor. See, e.g., Riddell et al., Nature Medicine 2, 216-223 (1996); Lamers, *Blood* 2011 117: 72-82. HLA tetramer binding assays may be used for the enumeration of antigen-specific T cells. In some aspects, lymphoproliferative assays (LPAs) and/or assays to assess for secreted cytokines, such as ELISAs and/or intracellular staining and assessment by flow cytometry, are used for detection of transgene-specific CD4+ T cells.

In some embodiments, the method prevents the induction of or reduces the level of antibodies against the receptor, e.g. anti-CAR antibodies. For example, antibody titers of anti-receptor, e.g. anti-CAR, antibodies, for example, as measured in the serum of the subject by ELISA, are decreased following administration of the consecutive dose, as compared to methods in which a consecutive dose is administered at a different time relative to the administration of the first dose, such as at a later time, e.g., following relapse. Thus, in some embodiments, the methods improve efficacy by increasing exposure of the subject to the administered cells by preventing or reducing host immune responses that would otherwise clear or prevent expansion of the administered cells.

VI. Disease Burden

The administration, e.g., of one or more of the doses, generally reduces or prevents the expansion or burden of the disease or condition in the subject. For example, where the disease or condition is a tumor, the methods generally reduce tumor size, bulk, metastasis, percentage of blasts in the bone marrow or molecularly detectable cancer and/or improve prognosis or survival or other symptom associated with tumor burden. In some embodiments, administration of the consecutive dose is timed with respect to a decrease in burden and/or relapse following the first or prior dose.

Disease burden can encompass a total number of cells of the disease in the subject or in an organ, tissue, or bodily fluid of the subject, such as the organ or tissue of the tumor or another location, e.g., which would indicate metastasis. For example, tumor cells may be detected and/or quantified in the blood or bone marrow in the context of certain hematological malignancies. Disease burden can include, in some embodiments, the mass of a tumor, the number or extent of metastases and/or the percentage of blast cells present in the bone marrow.

In some embodiments, a subject has leukemia. The extent of disease burden can be determined by assessment of residual leukemia in blood or bone marrow. In some embodiments, a subject exhibits morphologic disease if there are greater than or equal to 5% blasts in the bone marrow, for example, as detected by light microscopy. In some embodiments, a subject exhibits complete or clinical remission if there are less than 5% blasts in the bone marrow.

In some embodiments, a subject may exhibit complete remission, but a small proportion of morphologically undetectable (by light microscopy techniques) residual leukemic cells are present. A subject is said to exhibit minimum residual disease (MRD) if the subject exhibits less than 5% blasts in the bone marrow and exhibits molecularly detectable cancer. In some embodiments, molecularly detectable cancer can be assessed using any of a variety of molecular techniques that permit sensitive detection of a small number of cells. In some aspects, such techniques include PCR assays, which can determine unique Ig/T-cell receptor gene rearrangements or fusion transcripts produced by chromosome translocations. In some embodiments, flow cytometry can be used to identify cancer cell based on leukemia-specific immunophenotypes. In some embodiments, molecular detection of cancer can detect as few as 1 leukemia cell in 100,000 normal cells. In some embodiments, a subject exhibits MRD that is molecularly detectable if at least or greater than 1 leukemia cell in 100,000 cells is detected, such as by PCR or flow cytometry. In some embodiments, the disease burden of a subject is molecularly undetectable or MRD⁻, such that, in some cases, no leukemia cells are able to be detected in the subject using PCR or flow cytometry techniques.

In some embodiments, the methods and/or administration of the first dose decrease(s) disease burden as compared with disease burden at a time immediately prior to the administration of the first dose. In some aspects, administration of the first dose reduces disease burden, e.g. tumor burden. In some embodiments, the consecutive dose effects a reduction, e.g., a further reduction, in disease burden.

In some embodiments, the first dose contains the cells in an amount that is effective to reduce burden of a disease or condition in the subject, e.g., tumor burden. In some embodiments, e.g. where the disease or condition is a tumor, administration of the first dose is one that debulks the tumor. As used herein, a "debulking dose" refers to a dose that is effective to at least partially reduce burden of the disease or condition, e.g. tumor burden, in the subject. In some aspects, the debulking dose may not completely eradicate the disease or condition.

In some aspects, administration of the first dose and/or consecutive dose may prevent an increase in disease burden, and this may be evidenced by no change in disease burden.

In some aspects, the disease or condition persists following administration of the first dose and/or administration of the first dose is not sufficient to eradicate the disease or condition in the subject.

In some aspects, administration of the consecutive dose reduces disease burden as compared to disease burden at a time immediately prior to the first dose, or at a time immediately prior to the consecutive dose. In some aspects, for example in the context of relapse, administration of the consecutive dose effects a reduction in disease burden as compared to the peak level of disease burden following administration of the first dose.

In some embodiments, the method reduces the burden of the disease or condition, e.g., number of tumor cells, size of tumor, duration of patient survival or event-free survival, to a greater degree and/or for a greater period of time as compared to the reduction that would be observed with a comparable method using an alternative dosing regimen, such as one in which the subject receives a single dose, e.g., a single large dose, of cells, e.g. administration of the total number of cells administered in the first dose and the consecutive dose, collectively, in the provided methods, instead as a single dose, or administration of multiple large doses or multiple doses spaced from one another by less than about 14 or more than about 28 days. In some embodiments, disease burden is reduced to a greater extent or for a greater duration following the consecutive dose compared to the reduction that would be effected by administering the consecutive dose to a subject having not received the first dose.

In some embodiments, the burden of a disease or condition in the subject is detected, assessed, or measured. Disease burden may be detected in some aspects by detecting the total number of disease or disease-associated cells, e.g., tumor cells, in the subject, or in an organ, tissue, or bodily fluid of the subject, such as blood or serum. In some embodiments, disease burden, e.g. tumor burden, is assessed by measuring the mass of a solid tumor and/or the number or extent of metastases. In some aspects, survival of the subject, survival within a certain time period, extent of survival, presence or duration of event-free or symptom-free survival, or relapse-free survival, is assessed. In some embodiments, any symptom of the disease or condition is assessed. In some embodiments, the measure of disease or condition burden is specified.

In some aspects, disease burden is measured or detected prior to administration of the first dose, following the administration of the first dose but prior to administration of the consecutive dose, and/or following administration of the consecutive dose. In the context of multiple consecutive doses, disease burden in some embodiments may be measured prior to or following any of the consecutive doses, or at a time between administration of consecutive doses.

In some embodiments, the burden is decreased by or by at least at or about 10, 20, 30, 40, 50, 60, 70, 90, or 100 percent after administration of the first dose. In some aspects, administration of the consecutive dose effects a further reduction in disease burden, e.g. tumor burden, such as a at or about 10, 20, 30, 40, 50, 60, 70, 90, or 100 percent decrease in burden compared to immediately prior to the administration of the consecutive dose or overall compared to immediately prior to the first dose. In some embodiments, disease burden, tumor size, tumor volume, tumor mass, and/or tumor load or bulk is reduced following the consecutive dose by at least at or about 50, 60, 70, 80, 90% or more compared to that immediately prior to the administration of the first dose or of the consecutive dose.

In some embodiments, reduction of disease burden by the method comprises an induction in morphologic complete remission, for example, as assessed at 1 month, 2 months, 3 months, or more than 3 months, after administration of, e.g., initiation of, the first or consecutive dose. In some aspects, an assay for minimal residual disease, for example, as measured by multiparametric flow cytometry, is negative, or the level of minimal residual disease is less than about 0.3%, less than about 0.2%, less than about 0.1%, or less than about 0.05%.

In some embodiments, the event-free survival rate or overall survival rate of the subject is improved by the methods, as compared with other methods. For example, in some embodiments, event-free survival rate or probability for subjects treated by the methods at 6 months following the first dose is greater than about 40%, greater than about 50%, greater than about 60%, greater than about 70%, greater than about 80%, greater than about 90%, or greater than about 95%. In some aspects, overall survival rate is greater than about 40%, greater than about 50%, greater than about 60%, greater than about 70%, greater than about 80%, greater than about 90%, or greater than about 95%. In some embodiments, the subject treated with the methods exhibits event-free survival, relapse-free survival, or survival to at least 6 months, or at least 1, 2, 3, 4, 5, 6, 7, 8, 9, or 10 years. In some embodiments, the time to progression is improved, such as a time to progression of greater than at or about 6 months, or at least 1, 2, 3, 4, 5, 6, 7, 8, 9, or 10 years.

In some embodiments, following treatment by the method, the probability of relapse is reduced as compared to other methods. For example, in some embodiments, the probability of relapse at 6 months following the first dose is less than about 80%, less than about 70%, less than about 60%, less than about 50%, less than about 40%, less than about 30%, less than about 20%, or less than about 10%.

In some aspects, reduction of disease burden, e.g. debulking of the tumor, following the first dose reduces toxicity or toxic outcomes following the consecutive dose. Toxic outcomes following a reduction in tumor burden can be assessed as described herein.

In some aspects, reduction of disease burden, e.g. debulking of the tumor, resulting from the present methods improves the persistence of the cells in the subject. For example, in some aspects, administration of the first dose reduces disease burden, e.g. tumor burden, such that the cells administered in the consecutive dose persist for longer than cells administered by other dosing regimens, such as administering the consecutive dose to a subject that has not been administered the cells of the first dose.

VII. Cell Exposure and Persistence

In some embodiments, the dose amount(s) and/or timing thereof are designed to promote exposure of the subject to the cells, such as by promoting their expansion and/or persistence over time.

In some embodiments, the provided methods increase exposure of the subject to the administered cells (e.g., increased number of cells or duration over time) and/or improve efficacy and therapeutic outcomes in adoptive cell therapy. In some aspects, the methods are advantageous in that a greater and/or longer degree of exposure to the cells expressing the recombinant receptors, e.g., CAR-expressing cells, improves treatment outcomes as compared with other methods. Such outcomes may include patient survival and remission, even in individuals with severe tumor burden.

In some embodiments, the administration of the first dose, e.g., first low dose, increases maximum, total, and/or duration of exposure to the cells in the subject as compared to administration of a high initial dose of the cells. In some aspects, administration of the first dose in the context of high disease burden (and thus higher amounts of antigen) enhances efficacy as compared with administration of a larger dose in the same context, which may result in exhaustion which may prevent expansion and/or persistence of the cells. In some embodiments, administering the first dose in the context of high disease burden reduces exhaustion of the transferred cells, thereby increasing clinical efficacy as compared to other methods, such as those where a higher initial dose is administered.

In some embodiments, the presence and/or amount of cells expressing the recombinant receptor (e.g., CAR-expressing cells) in the subject following the first dose and/or following the consecutive dose is detected. In some aspects, quantitative PCR (qPCR) is used to assess the quantity of cells expressing the recombinant receptor (e.g., CAR-expressing cells) in the blood or serum or organ or tissue (e.g., disease site) of the subject. In some aspects, persistence is quantified as copies of DNA or plasmid encoding the receptor, e.g., CAR, per microgram of DNA, or as the number of receptor-expressing, e.g., CAR-expressing, cells per microliter of the sample, e.g., of blood or serum, or per total number of peripheral blood mononuclear cells (PBMCs) or white blood cells or T cells per microliter of the sample.

In some embodiments, the cells are detected in the subject at or at least at 4, 14, 15, 27, or 28 days following the administration of the first dose. In some aspects, the cells are detected at or at least at 2, 4, or 6 weeks following, or 3, 6, or 12, 18, or 24, or 30 or 36 months, or 1, 2, 3, 4, 5, or more years, following administration of the first or consecutive dose.

In some embodiments, the persistence of receptor, e.g., CAR, -expressing cells in the subject by the methods, following the consecutive dose, and/or following administration of the first dose, is greater as compared to that which would be achieved by alternative methods such as those involving the administration of a single dose, e.g., containing a larger number of cells than the first dose, administration of the cells of the collective doses as a single dose, administration of the cells of the consecutive dose without the subject having received the first dose, and/or administration of the consecutive dose at a time that is outside the specified time window such as later than the time specified or following the mounting of an immune response by the subject against the receptor, e.g., the CAR.

In some embodiments, the persistence and/or expansion and/or presence of recombinant receptor-expressing, e.g., CAR-expressing, cells in the subject following administration of the consecutive dose is greater as compared to that achieved via a method using an alternative dosing regimen, such as one involving the administration of the cells of the consecutive dose without the subject having been administered the cells of the first dose or where the subject is administered the cells collectively administered in the first and consecutive doses as a single dose.

The exposure, e.g., number of cells, indicative of expansion and/or persistence, may be stated in terms of maximum numbers of the cells to which the subject is exposed, duration of detectable cells or cells above a certain number or percentage, area under the curve for number of cells over time, and/or combinations thereof and indicators thereof. Such outcomes may be assessed using known methods, such as qPCR to detect copy number of nucleic acid encoding the recombinant receptor compared to total amount of nucleic acid or DNA in the particular sample, e.g., blood or serum, and/or flow cytometric assays detecting cells expressing the receptor generally using antibodies specific for the receptors. Cell-based assays may also be used to detect the number or percentage of functional cells, such as cells capable of binding to and/or neutralizing and/or inducing responses, e.g., cytotoxic responses, against cells of the disease or condition or expressing the antigen recognized by the receptor.

In some aspects, increased exposure of the subject to the cells includes increased expansion of the cells. In some embodiments, the receptor- (e.g., CAR-)expressing cells expand in the subject following administration of the first dose and/or following administration of the consecutive dose. In some aspects, the methods result in greater expansion of the cells compared with other methods, such as those involving the administration of the cells as a single dose, administration of larger first doses, administration of the consecutive dose without administering the first dose, and/or methods in which a consecutive dose is administered before or after the specified window of time or time point, such that, for example, an immune response develops prior to the administration of the consecutive dose.

In some aspects, the method results in high in vivo proliferation of the administered cells, for example, as measured by flow cytometry. In some aspects, high peak proportions of the cells are detected. For example, in some embodiments, at a peak or maximum level following the first or consecutive administration, in the blood or disease-site of the subject or white blood cell fraction thereof, e.g., PBMC fraction or T cell fraction, at least about 10%, at least about 20%, at least about 30%, at least about 40%, at least about 50%, at least about 60%, at least about 70%, at least about 80%, or at least about 90% of the cells express the recombinant receptor, e.g., the CAR.

In some embodiments, the method results in a maximum concentration, in the blood or serum or other bodily fluid or organ or tissue of the subject, of at least 100, 500, 1000, 1500, 2000, 5000, 10,000 or 15,000 copies of or nucleic acid encoding the receptor, e.g., the CAR per microgram of DNA, or at least 0.1, 0.2, 0.3, 0.4, 0.5, 0.6, 0.7, 0.8, or 0.9 receptor-expressing, e.g., CAR-expressing cells per total number of peripheral blood mononuclear cells (PBMCs), total number of mononuclear cells, total number of T cells, or total number of microliters. In some embodiments, the cells expressing the receptor are detected as at least 10, 20, 30, 40, 50, or 60% of total PBMCs in the blood of the subject, and/or at such a level for at least 1, 2, 3, 4, 5, 6, 7, 8, 9, 10, 11, 12, 24, 36, 48, or 52 weeks following the first or consecutive administration or for 1, 2, 3, 4, or 5, or more years following such administration.

In some aspects, the method results in at least a 2-fold, at least a 4-fold, at least a 10-fold, or at least a 20-fold increase in copies of nucleic acid encoding the recombinant receptor, e.g., CAR, per microgram of DNA, e.g., in the serum of the subject.

In some embodiments, cells expressing the receptor are detectable in the blood or serum of the subject, e.g., by a specified method, such as qPCR or flow cytometry-based detection method, at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 or more days following administration of the first dose or after administration of the consecutive dose, for at least at or about 2, 3, 4, 5, 6, 7, 8, 9, 10, 11, 12, 13, 14, 15, 16, 17, 18, 19, 20, 21, 22, 23, or 24 or more weeks following the administration of the first dose or the consecutive dose.

In some aspects, at least about $1 \times 10^2$, at least about $1 \times 10^3$, at least about $1 \times 10^4$, at least about $1 \times 10^5$, or at least about $1 \times 10^6$ or at least about $5 \times 10^6$ or at least about $1 \times 10^7$ or at least about $5 \times 10^7$ or at least about $1 \times 10^8$ recombinant receptor-expressing, e.g., CAR-expressing cells, and/or at least 10, 25, 50, 100, 200, 300, 400, or 500, or 1000 receptor-expressing cells per microliter, e.g., at least 10 per microliter, are detectable or are present in the subject or fluid, tissue, or compartment thereof, such as in the blood, e.g., peripheral blood, or disease site thereof. In some embodiments, such a number or concentration of cells is detectable in the subject for at least about 20 days, at least about 40 days, or at least about 60 days, or at least about 3, 4, 5, 6, 7, 8, 9, 10, 11, or 12 months, or at least 2 or 3 years, following administration of the first dose or following the administration of the consecutive dose(s). Such cell numbers may be as detected by flow cytometry-based or quantitative PCR-based methods and extrapolation to total cell numbers using known methods. See, e.g., Brentjens et al., *Sci Transl Med.* 2013 5(177), Park et al, Molecular Therapy 15(4):825-833 (2007), Savoldo et al., *JCI* 121(5):1822-1826 (2011), Davila et al. (2013) *PLoS ONE* 8(4):e61338, Davila et al., *Oncoimmunology* 1(9):1577-1583 (2012), Lamers, *Blood* 2011 117:72-82, Jensen et al. *Biol Blood Marrow Transplant* 2010 September; 16(9): 1245-1256, Brentjens et al., *Blood* 2011 118(18):4817-4828.

In some aspects, the copy number of nucleic acid encoding the recombinant receptor, e.g., vector copy number, per 100 cells, for example in the peripheral blood or bone marrow or other compartment, as measured by immunohistochemistry, PCR, and/or flow cytometry, is at least 0.01, at least 0.1, at least 1, or at least 10, at about 1 week, about 2 weeks, about 3 weeks, about 4 weeks, about 5 weeks, or at least about 6 weeks, or at least about 2, 3, 4, 5, 6, 7, 8, 9, 10, 11, or 12 months or at least 2 or 3 years following administration of the cells, e.g., the first or consecutive dose(s). In some embodiments, the copy number of the vector expressing the receptor, e.g. CAR, per microgram of genomic DNA is at least 100, at least 1000, at least 5000, or at least 10,000, or at least 15,000 or at least 20,000 at a time about 1 week, about 2 weeks, about 3 weeks, or at least about 4 weeks following administration of the first dose or consecutive dose(s) of receptor-expressing, e.g. CAR-expressing, cells, or at least 2, 3, 4, 5, 6, 7, 8, 9, 10, 11, or 12 months or at least 2 or 3 years following such administration.

In some aspects, the receptor, e.g. CAR, expressed by the cells, is detectable by quantitative PCR (qPCR) or by flow cytometry in the subject, blood thereof, and/or disease site thereof, at a time that is at least about 3 months, at least about 6 months, at least about 12 months, at least about 1 year, at least about 2 years, at least about 3 years, or more than 3 years, following the administration of the cells, e.g., following the initiation of the administration of the first dose or the consecutive dose or subsequent consecutive dose.

In some embodiments, the area under the curve (AUC) for concentration of receptor- (e.g., CAR-)expressing cells in a fluid, tissue, or organ, e.g., blood, of the subject over time following the administration of the first dose is greater as compared to that achieved via an alternative dosing regimen where the subject is administered the cells of the first dose and the consecutive dose as a single dose.

In some aspects, the area under the curve (AUC) for concentration of receptor- (e.g., CAR-)expressing cells in a fluid, tissue, or organ, e.g., blood, of the subject over time following the administration of the consecutive dose is greater as compared to that achieved via an alternative dosing regimen where the subject is administered the consecutive dose without having been administered the first dose or in which the cells of the first and second doses are administered in a single dose.

VIII. Recombinant Receptors Expressed by the Cells

The cells generally express recombinant receptors, including antigen receptors such as functional non-TCR antigen receptors, e.g., chimeric antigen receptors (CARs), and other antigen-binding receptors such as transgenic T cell receptors (TCRs). Also among the receptors are other chimeric receptors.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 Mar. 18(2): 160-75. In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337, U.S. Pat. Nos. 7,446,190, and 8,389,282.

Among the chimeric receptors are chimeric antigen receptors (CARs). The chimeric receptors, such as CARs, generally include an extracellular antigen binding domain, such as a portion of an antibody molecule, generally a variable heavy ($V_H$) chain region and/or variable light ($V_L$) chain region of the antibody, e.g., an scFv antibody fragment.

In some embodiments, the antibody portion of the recombinant receptor, e.g., CAR, further includes a spacer, which may be or include at least a portion of an immunoglobulin constant region or variant or modified version thereof, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. In some examples, the spacer is or is about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (2013) Clin. Cancer Res., 19:3153, international patent application publication number WO2014031687, U.S. Pat. No. 8,822,647 or published app. No. US2014/0271635.

In some embodiments, the constant region or portion is of a human IgG, such as IgG4 or IgG1. In some embodiments, the spacer has the sequence ESKYGPPCPPCP (set forth in SEQ ID NO: 1), and is encoded by the sequence set forth in SEQ ID NO: 2. In some embodiments, the spacer has the sequence set forth in SEQ ID NO: 3. In some embodiments, the spacer has the sequence set forth in SEQ ID NO: 4. In some embodiments, the constant region or portion is of IgD. In some embodiments, the spacer has the sequence set forth in SEQ ID NO: 5. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 1, 3, 4 or 5.

This antigen recognition domain generally is linked to one or more intracellular signaling components, such as signaling components that mimic activation through an antigen receptor complex, such as a TCR complex, in the case of a CAR, and/or signal via another cell surface receptor. Thus, in some embodiments, the antigen-binding component (e.g., antibody) is linked to one or more transmembrane and intracellular signaling domains. In some embodiments, the transmembrane domain is fused to the extracellular domain.

In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD 16, CD22, CD33, CD37, CD64, CD80, CD86, CD 134, CD137, CD 154 and/or transmembrane regions containing functional variants thereof such as those retaining a substantial portion of the structural, e.g., transmembrane, properties thereof. In some embodiments, the transmembrane domain is a transmembrane domain derived from CD4, CD28, or CD8, e.g., CD8alpha, or functional variant thereof. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR or other chimeric receptor includes a chimeric molecule between CD3-zeta (CD3-ζ) or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR zeta, FcR gamma, FcR beta, CD3 gamma, CD3 delta, CD3 epsilon, CD8, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., *Sci. Transl. Medicine,* 5(215) (December, 2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In some embodiments, the intracellular signaling component of the recombinant receptor, such as CAR, comprises a CD3 zeta intracellular domain and a costimulatory signaling region. In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and/or CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the CAR or other antigen receptor further includes a marker, such as a cell surface marker, which may be used to confirm transduction or engineering of the cell to express the receptor, such as a truncated version of a cell surface receptor, such as truncated EGFR (tEGFR). In some aspects, the marker includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in published patent application No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 15 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 15. An exemplary T2A linker sequence comprises the sequence of amino acids set forth in SEQ ID NO: 14 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 14.

In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv and the intracellular domain contains an ITAM. In some aspects, the intracellular signaling domain includes a signaling domain of a zeta chain of a CD3-zeta (CD3ζ) chain. In some embodiments, the chimeric antigen receptor includes a transmembrane domain linking the extracellular domain and the intracellular signaling domain. In some aspects, the transmembrane domain contains a transmembrane portion of CD28. In some embodiments, the chimeric antigen receptor contains an intracellular domain of a T cell costimulatory molecule. The extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

For example, in some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the recombinant receptor, e.g., the CAR, is or includes a transmembrane domain of human CD28 (e.g. Accession No. P01747.1) or variant thereof, such as a transmembrane domain that comprises the sequence of amino acids set forth in SEQ ID NO: 6 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6; in some embodiments, the transmembrane-domain containing portion of the recombinant receptor comprises the sequence of amino acids set forth in SEQ ID NO: 7 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the intracellular signaling component(s) of the recombinant receptor, e.g. the CAR, contains an intracellular costimulatory signaling domain of human CD28 or a functional variant or portion thereof, such as a domain with an LL to GG substitution at positions 186-187 of a native CD28 protein. For example, the intracellular signaling domain can comprise the sequence of amino acids set forth in SEQ ID NO: 8 or 9 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 8 or 9. In some embodiments, the intracellular domain comprises an intracellular costimulatory signaling domain of 4-1BB (e.g. (Accession No. Q07011.1) or functional variant or portion thereof, such as the sequence of amino acids set forth in SEQ ID NO: 10 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 10.

In some embodiments, the intracellular signaling domain of the recombinant receptor, e.g. the CAR, comprises a human CD3 zeta stimulatory signaling domain or functional variant thereof, such as an 112 AA cytoplasmic domain of isoform 3 of human CD3 (Accession No.: P20963.2) or a CD3 zeta signaling domain as described in U.S. Pat. No. 7,446,190 or 8,911,993. For example, in some embodiments, the intracellular signaling domain comprises the sequence of amino acids as set forth in SEQ ID NO: 11, 12 or 13 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 11, 12 or 13.

In some aspects, the spacer contains only a hinge region of an IgG, such as only a hinge of IgG4 or IgG1, such as the hinge only spacer set forth in SEQ ID NO: 1. In other embodiments, the spacer is or contains an Ig hinge, e.g., an IgG4-derived hinge, optionally linked to a CH2 and/or CH3 domains. In some embodiments, the spacer is an Ig hinge, e.g., an IgG4 hinge, linked to CH2 and CH3 domains, such as set forth in SEQ ID NO: 4. In some embodiments, the spacer is an Ig hinge, e.g., an IgG4 hinge, linked to a CH3 domain only, such as set forth in SEQ ID NO: 3. In some embodiments, the spacer is or comprises a glycine-serine rich sequence or other flexible linker such as known flexible linkers.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer such as any of the Ig-hinge containing spacers, a CD28-derived transmembrane domain, a 4-1BB-derived intracellular signaling domain, and a CD3 zeta-derived signaling domain.

In some embodiments, such CAR constructs further includes a T2A ribosomal skip element and/or a tEGFR sequence, e.g., downstream of the CAR, such as set forth in SEQ ID NO: 14 and/or 15, respectively, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 14 or 15.

The terms "polypeptide" and "protein" are used interchangeably to refer to a polymer of amino acid residues, and are not limited to a minimum length. Polypeptides, including the provided receptors and other polypeptides, e.g., linkers or peptides, may include amino acid residues including natural and/or non-natural amino acid residues. The terms also include post-expression modifications of the polypeptide, for example, glycosylation, sialylation, acetylation, and phosphorylation. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

In some embodiments, the receptor, e.g., the CAR, expressed by the cells in the consecutive dose contains at least one immunoreactive epitope as the receptor, e.g., the CAR, expressed by the cells of the first dose. In some aspects, the receptor, e.g., the CAR, expressed by the cells administered in the consecutive dose is identical to the receptor, e.g., the CAR, expressed by the first dose or is substantially identical to the receptor, e.g., the CAR, expressed by the cells of administered in the first dose.

The recombinant receptors, such as CARs, expressed by the cells administered to the subject in the various doses generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells in the first dose express a CAR that specifically binds to an antigen expressed by a cell or tissue of the disease or condition or associated with the disease or condition.

The receptor, e.g., the CAR, expressed by the cells in the consecutive dose(s) generally specifically binds to the same antigen as the CAR of the first dose and is often the same receptor or extremely similar to the receptor in the cells of the first dose. In some embodiments, the receptor on the cells in the consecutive dose(s) is the same as or shares a large degree of identity with the receptor in the cells of the first dose.

In some embodiments, the CAR expressed by the cells of the consecutive dose contains the same scFv, the same signaling domains, and/or the same junctions as the CAR expressed by the cells of the first dose. In some embodiments, it further contains the same costimulatory, stimulatory, transmembrane, and/or other domains as that of the first dose. In some embodiments, one or more component of the CAR of the consecutive dose is distinct from the CAR of the first dose.

IX. Engineered Cells

Among the cells expressing the receptors and administered by the provided methods are engineered cells.

The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, and re-introducing them into the same subject, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

Vectors and Methods for Genetic Engineering

Also provided are methods, compositions, and kits, for producing the genetically engineered cells expressing recombinant receptors. The genetic engineering generally involves introduction of a nucleic acid encoding the recombinant or engineered component into the cell, such as by retroviral transduction, transfection, or transformation.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the subject to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell II: 223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some aspects, the cells further are engineered to promote expression of cytokines or other factors. Various methods for the introduction of genetically engineered components, e.g., antigen receptors, e.g., CARs, are well known and may be used with the provided methods and compositions. Exemplary methods include those for transfer of nucleic acids encoding the receptors, including via viral, e.g., retroviral or lentiviral, transduction, transposons, and electroporation.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) *J. Immunother.* 35(9): 689-701; Cooper et al. (2003) *Blood.* 101: 1637-1644; Verhoeyen et al. (2009) *Methods Mol Biol.* 506: 97-114; and Cavalieri et al. (2003) Blood. 102(2): 497-505.

In some embodiments, recombinant nucleic acids are transferred into T cells via electroporation (see, e.g., Chicaybam et al, (2013) *PLoS ONE* 8(3): e60298 and Van Tedeloo et al. (2000) *Gene Therapy* 7(16): 1431-1437). In some embodiments, recombinant nucleic acids are transferred into T cells via transposition (see, e.g., Manuri et al. (2010) Hum Gene Ther 21(4): 427-437; Sharma et al. (2013) *Molec Ther Nucl Acids* 2, e74; and Huang et al. (2009) *Methods Mol Biol* 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

Preparation of Cells for Engineering

In some embodiments, preparation of the engineered cells includes one or more culture and/or preparation steps. The cells for introduction of the nucleic acid encoding the transgenic receptor such as the CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using CD3/CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed ($marker^+$) at a relatively higher level ($marker^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naïve, memory, and/or effector T cell subpopulations.

In some embodiments, $CD8^+$ cells are further enriched for or depleted of naïve, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) *J Immunother.* 35(9):689-701. In some embodiments, combining $T_{CM}$-enriched $CD8^+$ T cells and $CD4^+$ T cells further enhances efficacy.

In embodiments, memory T cells are present in both $CD62L^+$ and $CD62L^-$ subsets of $CD8^+$ peripheral blood lymphocytes. PBMC can be enriched for or depleted of $CD62L^-CD8^+$ and/or $CD62L^+CD8^+$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a $CD8^+$ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the $CD8^+$ cell population or subpopulation, also is used to generate the $CD4^+$ cell population or sub-population, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of $CD4^+$ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

$CD4^+$ T helper cells are sorted into naïve, central memory, and effector cells by identifying cell populations that have cell surface antigens. $CD4^+$ lymphocytes can be obtained by standard methods. In some embodiments, naïve $CD4^+$ T lymphocytes are $CD45RO^-$, $CD45RA^+$, $CD62L^+$, $CD4^+$ T cells. In some embodiments, central memory $CD4^+$ cells are $CD62L^+$ and $CD45RO^+$. In some embodiments, effector $CD4^+$ cells are $CD62L^-$ and $CD45RO^-$.

In one example, to enrich for $CD4^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, N.J.).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS) (Miltenyi Biotech, Auburn, Calif.). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotic), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood. 1:72-82, and Wang et al. (2012) *J Immunother.* 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

In some embodiments, the provided methods include cultivation, incubation, culture, and/or genetic engineering steps. For example, in some embodiments, provided are methods for incubating and/or engineering the depleted cell populations and culture-initiating compositions.

Thus, in some embodiments, the cell populations are incubated in a culture-initiating composition. The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to the culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naïve or antigen specific T lymphocytes with antigen. For example, antigen-specific T cell lines or clones can be generated to cytomegalovirus antigens by isolating T cells from infected subjects and stimulating the cells in vitro with the same antigen.

X. Compositions and Formulations

Also provided are compositions including the cells for administration, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine.

The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

In some embodiments, the composition includes the cells in an amount effective to reduce burden of the disease or condition, and/or in an amount that does not result in CRS or severe CRS in the subject and/or to effect any of the other outcomes of the methods as described herein.

The cells and compositions may be administered using standard administration techniques, formulations, and/or devices. Administration of the cells can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

XII. Articles of Manufacture

Also provided are articles of manufacture, such as kits and devices, for the administration of the cells to subjects in according to the provided methods for adoptive cell therapy, and for storage and administration of the cells and compositions.

The articles of manufacture include one or more containers, typically a plurality of containers, packaging material, and a label or package insert on or associated with the container or containers and/or packaging, generally including instructions for administration of the cells to a subject.

The containers generally contain the cells to be administered, e.g., one or more unit doses thereof. The article of manufacture typically includes a plurality of containers, each containing a single unit dose of the cells. The unit dose may be an amount or number of the cells to be administered to the subject in the first dose or twice the number (or more) the cells to be administered in the first or consecutive dose(s). It may be the lowest dose or lowest possible dose of the cells that would be administered to the subject in connection with the administration method. In some embodiments, the unit dose is the minimum number of cells or number of cells that would be administered in a single dose to any subject having a particular disease or condition or any subject, according to the methods herein. For example, the unit dose in some aspects may include a minimum number of cells that would be administered to a patient of a relatively lower body weight and/or with relatively low disease burden, such that one and in some cases more than one unit dose is administered to a given subject as a first dose and one or more than one unit dose is administered to a given subject in one or more consecutive dose, e.g., according to the provided methods. In some embodiments, the number of cells in the unit dose is the number of cells or number of recombinant receptor-expressing or CAR-expressing cells that it is desired to administer to a particular subject in a first dose, such as a subject from which the cells have been derived. In some embodiments, the cells have been derived from the subject to be treated by methods as provided herein or in need thereof.

In some embodiments, each of the containers individually comprises a unit dose of the cells, e.g., including the same or substantially the same number of cells. Thus in some embodiments, each of the containers comprises the same or approximately or substantially the same number of cells or number of recombinant receptor-expressing cells. In some embodiments, the unit dose includes less than about $1 \times 10^8$, less than about $5 \times 10^7$, less than about $1 \times 10^6$ or less than about $5 \times 10^5$ of the engineered cells, of total cells, of T cells, or PBMCs, per kg of the subject to be treated and/or from which the cells have been derived. In some embodiments, each unit dose contains at or about $2 \times 10^6$, $5 \times 10^6$, $1 \times 10^7$, $5 \times 10^7$, or $1 \times 10^8$ engineered cells, total cells, T cells, or PBMCs.

Suitable containers include, for example, bottles, vials, syringes, and flexible bags, such as infusion bags. In particular embodiments, the containers are bags, e.g., flexible bags, such as those suitable for infusion of cells to subjects, e.g., flexible plastic or PVC bags, and/or IV solution bags. The bags in some embodiments are sealable and/or able to be sterilized, so as to provide sterile solution and delivery of the cells and compositions. In some embodiments, the containers, e.g., bags, have a capacity of at or about or at least at or about 10, 20, 30, 40, 50, 60, 70, 80, 90, 100, 200, 300, 400, 500, or 1000 ml capacity, such as between at or about 10 and at or about 100 or between at or about 10 and at or about 500 mL capacity. In some embodiments, the containers, e.g., bags, are and/or are made from material which is stable and/or provide stable storage and/or maintenance of cells at one or more of various temperatures, such as in cold temperatures, e.g. below at or about or at or about $-20°$ C., $-80°$ C., $-120°$ C., $135°$ C. and/or temperatures suitable for cryopreservation, and/or other temperatures, such as temperatures suitable for thawing the cells and body temperature such as at or about $37°$ C., for example, to permit thawing, e.g., at the subject's location or location of treatment, e.g., at bedside, immediately prior to treatment.

The containers may be formed from a variety of materials such as glass or plastic. In some embodiments, the container has one or more port, e.g., sterile access ports, for example, for connection of tubing or cannulation to one or more tubes, e.g., for intravenous or other infusion and/or for connection for purposes of transfer to and from other containers, such as cell culture and/or storage bags or other containers. Exemplary containers include infusion bags, intravenous solution bags, vials, including those with stoppers pierceable by a needle for injection.

The article of manufacture may further include a package insert or label with one or more pieces of identifying information and/or instructions for use. In some embodiments, the information or instructions indicates that the contents can or should be used to treat a particular condition or disease, and/or providing instructions therefor. The label or package insert may indicate that the contents of the article of manufacture are to be used for treating the disease or condition. In some embodiments, the label or package insert provides instructions to treat a subject, e.g., the subject from which the cells have been derived, via a method involving the administration of a first and one or more consecutive doses of the cells, e.g., according to any of the embodiments of the provided methods. In some embodiments, the instructions specify administration, in a first dose, of one unit dose, e.g., the contents of a single individual container in the article of manufacture, followed by one or more consecutive doses at a specified time point or within a specified time window and/or after the detection of the presence or absence or amount or degree of one or more factors or outcomes in the subject.

In some embodiments, the instructions specify administering a plurality of the unit doses to the subject by carrying out a first administration and a consecutive administration. In some embodiments, the first administration comprises delivering one of said unit doses to the subject and the consecutive administration comprises administering one or a plurality of said unit doses to the subject.

In some embodiments, the instructions specify that the consecutive administration is to be carried out at a time between about 15 and about 27 days or between about 9 and about 35 days, e.g., at or about 21 days, following the first administration, e.g., following the initiation of the first administration or the prior administration. In some embodiments, the instructions specify that the consecutive dose is to be administered at a time after which it has been determined that a serum level of a factor indicative of cytokine-release syndrome (CRS) in the subject is less than about 10 times, less than about 25 times, and/or less than about 50 times the serum level of the indicator in the subject immediately prior to said first administration, and/or that an indicator of CRS has peaked and is declining, and/or that the subject does not exhibit a detectable adaptive host immune response specific for the receptor, e.g., CAR, expressed by the cells.

In some embodiments, the label or package insert or packaging comprises an identifier to indicate the specific identity of the subject from which the cells are derived and/or are to be administered. In the case of autologous transfer, the identity of the subject from which the cells are derived is the same as the identity of the subject to which the cells are to be administered. Thus, the identifying information may specify that the cells are to be administered to a particular patient, such as the one from which the cells were originally derived. Such information may be present in the packaging material and/or label in the form of a bar code or other coded identifier, or may indication the name and/or other identifying characteristics of the subject.

The article of manufacture in some embodiments includes one or more, typically a plurality, of containers containing compositions comprising the cells, e.g., individual unit dose forms thereof, and further include one or more additional containers with a composition contained therein which includes a further agent, such as a cytotoxic or otherwise therapeutic agent, for example, which is to be administered in combination, e.g., simultaneously or sequentially in any order, with the cells. Alternatively, or additionally, the article of manufacture may further include another or the same container comprising a pharmaceutically-acceptable buffer. It may further include other materials such as other buffers, diluents, filters, tubing, needles, and/or syringes.

The term "package insert" is used to refer to instructions customarily included in commercial packages of therapeutic products, that contain information about the indications, usage, dosage, administration, combination therapy, contraindications and/or warnings concerning the use of such therapeutic products.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a composition refers to any mixture of two or more products, substances, or compounds, including cells. It may be a solution, a suspension, liquid, powder, a paste, aqueous, non-aqueous or any combination thereof.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

XIII. Exemplary Embodiments

Among the embodiments provided herein are:

1. A method of treatment, comprising:
  (a) administering to a subject having a disease or condition a first dose of cells expressing a chimeric antigen receptor (CAR), said first dose comprising no more than about $1 \times 10^6$ of the cells per kilogram body weight of the subject, no more than about $1 \times 10^8$ of the cells, and/or no more than about $1 \times 10^8$ of the cells/m$^2$ of the subject; and
  (b) administering to the subject a consecutive dose of cells expressing a CAR at a time point that is at least or more than about 14 days after and less than about 28 days after initiation of said administration in (a).

2. The method of embodiment 1, wherein, at the time of the administration in (b):
  (i) the serum level in the subject of a factor indicative of cytokine release syndrome (CRS) is less than about 10 times, less than about 25 times, and/or less than about 50 times that in the subject immediately prior to said administration in (a); and/or
  (ii) the subject does not exhibit grade 3 or higher neurotoxicity; and/or
  (iii) a CRS-related outcome or symptom of neurotoxicity in the subject following said administration of said first dose has reached a peak level and begun to decline following the administration in (a); and/or
  (iv) the subject does not exhibit a detectable humoral or cell-mediated immune response against the CAR expressed by the cells of said first dose.

3. A method of treatment, comprising:
  (a) administering to a subject a first dose of cells expressing a chimeric antigen receptor (CAR), said first dose comprising the cells in an amount sufficient to reduce burden of a disease or condition in the subject; and
  (b) administering to the subject a consecutive dose of CAR-expressing cells at a time at which:
    (i) a clinical risk for neurotoxicity, cytokine-release syndrome (CRS), macrophage activation syndrome, or tumor lysis syndrome, is not present or has passed or has subsided following said administration in (a), (ii) a biochemical readout evidencing (CRS), neurotoxicity, macrophage activation syndrome, or tumor lysis syndrome, is not present or has passed or has subsided following said administration in (a), and/or (iii) a serum level of a factor indicative of cytokine-release syndrome (CRS) or neurotoxicity in the subject is less than about 10 times, less than about 25 times, and/or less than about 50 times the serum level of said indicator in the subject immediately prior to said administration in (a); and
  the subject does not exhibit a detectable adaptive host immune response specific for the CAR expressed by the cells of said first dose.

4. A method of treatment, comprising:
  (a) administering to a subject a first dose of cells expressing a chimeric antigen receptor (CAR), said first dose comprising the cells in an amount sufficient to reduce burden of a disease or condition in the subject; and
  (b) administering to the subject a consecutive dose of CAR-expressing cells, at a time after a neurotoxicity and/or CRS-related outcome in the subject has reached a peak level and begun to decline following said administration in (a) and at which the subject does not exhibit a detectable humoral or cell-mediated immune response against the CAR expressed by the cells of said first dose.

5. The method of embodiment 3 or embodiment 4, wherein:
  (i) the administration in (a) does not induce severe CRS in the subject or does not induce CRS in the subject;
  (ii) the administration in (a) does not induce grade 3 or higher neurotoxicity in the subject;
  (iii) based on clinical data, the administration of the dose of cells in (a) does not induce severe CRS in a majority of subjects so-treated; and/or
  (iv) based on clinical data, the administration of the dose of cells in (a) does not induce grade 3 or higher neurotoxicity in a majority of subjects so-treated.

6. The method of any of embodiments 3-5, wherein:
  the time between the initiation of the administration in (a) and the initiation of the administration in (b) is between about 9 and about 35 days, between about 14 and about 28 days, between 15 and 27 days or is between 17 days and about 21 days, each inclusive; and/or
  said first dose comprises no more than about $1 \times 10^6$ of the cells per kilogram body weight of the subject, no more than about $1 \times 10^8$ of the cells, or no more than about $1 \times 10^8$ of the cells/m$^2$ of the subject.

7. The method of any of embodiments 2-6, wherein the CRS-related outcome is selected from the group consisting of fever, hypotension, hypoxia, neurologic disturbances, or a serum level of an inflammatory cytokine or C reactive protein (CRP).

8. The method of any of embodiments 2-6, wherein the factor indicative of CRS is an inflammatory cytokine selected from the group consisting of interferon gamma (IFNγ), granulocyte-macrophage colony-stimulating factor (GM-CSF), tumor necrosis factor alpha (TNFα), IL-6, IL-10, IL-1β, IL-8, IL-2, MIP-1, Flt-3L, fracktalkine, and IL-5 or is CRP.

9. The method of any of embodiments 2-8, wherein, at the time of the administration in (b):
  said level of said CRS-related outcome is no more than 50% of the peak level, is no more than 20% of the peak level, or is no more than 5% of the peak level, or is at or about the level immediately prior to the administration in (a); or said serum level of said factor indicative of CRS is no more than ten times the level immediately prior to the administration in (a).

10. The method of any of embodiments 2-9, wherein symptoms associated with a clinical risk of neurotoxicity and/or grade 3 or higher neurotoxicity are selected from among confusion, delirium, expressive aphasia, obtundation, myoclonus, lethargy, altered mental status, convulsions, seizure-like activity, seizures (optionally as confirmed by electroencephalogram [EEG]), elevated levels of beta amyloid (Aβ), elevated levels of glutamate, and elevated levels of oxygen radicals.

11. The method of any of embodiments 1-10, wherein said subject has not received a dose of cells expressing the CAR expressed by the cells in the first dose prior to the administration in (a).

12. The method of any of embodiments 1-11, wherein the CAR expressed by the cells in the consecutive dose contains at least one immunoreactive epitope present in the CAR expressed by the cells in the first dose.

13. The method of embodiment 12, wherein the CAR expressed by the cells in the consecutive dose is identical to the CAR expressed by the cells in the first dose or is substantially identical to the CAR expressed by the cells in the first dose.

14. The method of any of embodiments 1-13, wherein the CAR expressed by the cells in the first dose specifically binds to an antigen expressed by a cell or tissue of the disease or condition or associated with the disease or condition.

15. The method of embodiment 14, wherein the disease or condition is a tumor or a cancer.

16. The method of embodiment 15, wherein the administration in (a) leads to a reduction in burden of the disease or condition in the subject, as indicated by a reduction in one or more factors indicative of disease burden following said administration in (a).

17. The method of embodiment 16, wherein at the time of the administration in (b), the subject has not relapsed and/or the one or more factors indicative of disease burden have not increased following said reduction.

18. The method of any of embodiments 1-17, wherein the consecutive dose of cells comprises cells in an amount sufficient for reduction in burden of a disease or condition in the subject.

19. The method of any of embodiments 16-18, wherein the administration in (b) leads to a further reduction in burden of the disease or condition in the subject.

20. The method of any of embodiments 1-19, wherein said administration of said consecutive dose leads to a reduction in burden of the disease or condition in the subject as compared with immediately prior to initiation of the administration of the consecutive dose.

21. The method of any of embodiments 1-20, wherein the method reduces burden of the disease or condition to a greater degree and/or for a greater period of time as compared to a method comprising an alternative dosing regimen wherein the subject is administered the cells in (a) and the cells in (b) in a single dose.

22. The method of any of embodiments 16-22, wherein:
said reduction in burden and/or further reduction in burden comprises a reduction in total number of cells of the disease in the subject, in an organ of the subject, in a tissue of the subject, or in a bodily fluid of the subject, a reduction in mass or volume of a tumor, and/or a reduction in number and/or extent of metastases.

23. The method of any of embodiments 1-22, wherein:
the disease is a cancer and the subject does not exhibit morphologic disease at the time of initiation of the administration in (b); and/or
the disease is a leukemia or lymphoma and the subject does not exhibit greater than 5% blast cells in the bone marrow at the time of the administration in (b).

24. The method of any of embodiments 1-23, wherein the disease or condition persists following the administration of said first dose and/or the administration of the first dose is not sufficient to eradicate the disease or condition in the subject.

25. The method of any of embodiments 1-24, wherein the subject exhibits detectable molecular disease and/or minimum residual disease at the time of the administration in (b).

26. The method of any of embodiments 1-25, wherein (i) the maximum number of CAR-expressing cells, (ii) the area under the curve (AUC) of CAR-expressing cells over time, and/or (iii) the duration of detectable CAR-expressing cells in the subject following said administration in (b) is greater, as compared to that achieved via a method comprising an alternative dosing regimen wherein the subject is administered the cells in (a) and the cells in (b) as a single dose.

27. The method of any of embodiments 1-26, wherein:
the method results in a maximum concentration or number of CAR-expressing cells in the blood of the subject of at least at or about 10 CAR-expressing cells per microliter, at least 50% of the total number of peripheral blood mononuclear cells (PBMCs), at least at least about $1 \times 10^5$ CAR-expressing cells, or at least 5,000 copies of CAR-encoding DNA per micrograms DNA; and/or
at day 90 following the initiation of the administration in (a), CAR-expressing cells are detectable in the blood or serum of the subject; and/or
at day 90 following the initiation of the administration in (a), the blood of the subject contains at least 20% CAR-expressing cells, at least 10 CAR-expressing cells per microliter or at least $1 \times 10^4$ CAR-expressing cells.

28. The method of any of embodiments 1-27, wherein the area under the curve (AUC) for blood concentration of CAR-expressing cells over time following the administration in (a) is greater as compared to that achieved via a method comprising an alternative dosing regimen wherein the subject is administered the cells in (a) and the cells in (b) as a single dose.

29. The method of any of embodiments 1-28, wherein a CRS-related outcome in the subject at day 2, 3, 4, 5, 6, 7, 8, 9, 10, 11, 12, 13, or 14 following the administration in (b) is not detectable or is reduced as compared to a method comprising an alternative dosing regimen wherein the subject is administered the cells in (b) without having been administered the first dose.

30. The method of any of embodiments 1-29, wherein the area under the curve (AUC) for a serum level of a factor indicative of CRS over time in the subject following the administration in (b) is lower as compared to that of a method comprising an alternative dosing regimen wherein the subject is administered the cells in (b) without having been administered the first dose.

31. The method of any of embodiments 15-30, wherein the subject has been treated with a therapeutic agent targeting the tumor or cancer prior to said administration in (a) and is refractory or non-responsive to said therapeutic agent at the time of the administration in (a).

32. The method of any of embodiments 1-31, further comprising, subsequent to administration in (a) and before said administration in (b), or prior to administration in (a), assessing a serum level of a factor indicative of CRS, a factor indicative of neurotoxicity, a factor indicative of disease burden, and/or an indicator of a host anti-CAR immune response in said subject.

33. The method of embodiment 32, wherein the factor indicative of disease burden is measured and comprises a total number of cells of the disease in the subject, in an organ of the subject, in a tissue of the subject, or in a bodily fluid of the subject, molecular detection by flow cytometry or quantitative PCR, mass or volume of a solid tumor, or number or extent of metastases.

34. The method of embodiment 32 or embodiment 33, comprising:

i) assessing a factor indicative of disease burden prior to administration in (b); and ii) based on the result of the assessment, determining the consecutive dose of cells to be administered to the subject, and:

iii) if the assessment determines that the subject has morphologic disease, administering to the subject a consecutive dose comprising less than or about the same number of CAR-expressing cells as the number of CAR-expressing cells in the first dose; and/or if the assessment determines that the subject has minimal residual disease, administering to the subject a consecutive dose comprising an increased number of CAR-expressing cells as compared to the first dose.

35. The method of any of embodiments 1-33, wherein the consecutive dose comprises about the same number of CAR-expressing cells as the number of CAR-expressing cells in the first dose.

36. The method of any of embodiments 1-33, wherein the consecutive dose comprises an increased number of CAR-expressing cells as compared to the first dose.

37. A method of treatment, comprising administering a consecutive dose of cells expressing a chimeric antigen receptor (CAR) to a subject previously administered a first dose of cells expressing a CAR, wherein:

the consecutive dose of cells is administered at a time point that is at least or more than about 14 days after and less than about 28 days after initiation of the first dose; and/or the number of CAR-expressing cells administered in the consecutive dose is increased as compared to the first dose.

38. The method of any of embodiments 1-37, wherein the number of cells administered in the first dose is between about $0.5 \times 10^6$ cells/kg body weight of the subject and $3 \times 10^6$ cells/kg, between about $0.75 \times 10^6$ cells/kg and $2.5 \times 10^6$ cells/kg or between about $1 \times 10^6$ cells/kg and $2 \times 10^6$ cells/kg, each inclusive.

39. The method of embodiment 34, 36 or 37, wherein the increased number is at least 2-fold, 5-fold, or 10-fold greater than the number in the first dose.

40. The method of any of embodiments 1-39, wherein the number of cells administered in the consecutive dose of CAR-expressing cells comprises between about $2 \times 10^6$ cells per kilogram (cells/kg) body weight and about $6 \times 10^6$ cells/kg, between about $2.5 \times 10^6$ cells/kg and about $5.0 \times 10^6$ cells/kg, or between about $3.0 \times 10^6$ cells/kg and about $4.0 \times 10^6$ cells/kg, each inclusive.

41. The method of any of embodiments 1-40, wherein the subject does not exhibit cytokine release syndrome (CRS), does not exhibit severe CRS, does not exhibit neurotoxicity, does not exhibit severe neurotoxicity, or does not exhibit neurotoxicity above grade 3 following administration of the first dose and/or following the administration in of the consecutive dose.

42. The method of any of embodiments 1-41, wherein the CAR-expressing cells in the first dose expand in the subject following administration of the first dose and/or following the administration of the consecutive dose.

43. The method of embodiment 42, wherein the expansion is evidenced by (i) an increase in serum CRP level following the administration of the first dose and/or consecutive dose as compared to just prior to the administration, and/or (ii) an increase in level of CAR-encoding nucleic acid in the serum, as measured by qPCR, following the administration of the first dose and/or consecutive dose as compared to just prior to the administration, wherein said increase is optionally at least 1, 2, or 3-fold.

44. The method of any of embodiments 1-43, wherein the time between the first and consecutive dose is between 15 and 27 days.

45. The method of embodiment 44, wherein the time between the first and consecutive dose is about 21 days.

46. The method of embodiment 44, wherein the time between the first and consecutive dose is about 17 days.

47. The method of any of embodiments 1-46, wherein the cells of the first dose are administered in a single pharmaceutical composition comprising the cells of the first dose and/or wherein the cells of the consecutive dose are administered in a single pharmaceutical composition comprising the cells of the consecutive dose.

48. The method of any of embodiments 1-47, wherein:

the first dose is a split dose, wherein the cells of the first dose are administered in a plurality of compositions, collectively comprising the cells of the first dose, over a period of no more than three days; and/or the consecutive dose is a split dose, wherein the cells of the consecutive dose are administered in a plurality of compositions, collectively comprising the cells of the consecutive dose, over a period of no more than three days.

49. The method of any of embodiments 1-48, wherein the method further comprises administering a chemotherapeutic agent prior to the administration in (a) and/or the administration in (b) or wherein the subject has been previously treated with a chemotherapeutic agent prior to the administration of the first dose.

50. The method of embodiment 49, wherein the chemotherapeutic agent comprises an agent selected from the group consisting of cyclophosphamide, fludarabine, and/or a combination thereof.

51. The method of embodiment 49 or 50, wherein the administration of the chemotherapeutic agent comprises administration of a chemotherapeutic agent prior to the administration in (a) and optionally not prior to the administration in (b).

52. The method of any of embodiments 49-51, wherein the chemotherapeutic agent is administered between 2 and 5 days prior to the administration in (a) and/or is administered between 2 and 5 days prior to the administration in (b).

53. The method of any of embodiments 49-52, wherein the chemotherapeutic agent is administered at a dose of between at or about 1 $g/m^2$ of the subject and at or about 100 $g/m^2$, 15 $g/m^2$ of the subject and 50 $g/m^2$ of the subject, 0.5 $g/m^2$ of the subject and 5 $g/m^2$ of the subject, or 1 $g/m^2$ of the subject and at or about 3 $g/m^2$ of the subject.

54. The method of any of embodiments 1-53, wherein the subject has received cryoreductive chemotherapy prior to the administration or the first dose or the method further comprises the administration of cryoreductive chemotherapy prior to the administration of the first dose.

55. The method of any of embodiments 49-54, wherein the chemotherapeutic agent comprises conditioning chemotherapy, which reduces burden of the disease or condition in the subject.

56. A method of providing consolidating treatment, comprising administering to a subject a consecutive dose of cells expressing a chimeric antigen receptor (CAR), wherein:

prior to said administration, the subject has received a previous dose of CAR-expressing in an amount sufficient to reduce burden of a disease or condition in the subject; and at the time of administration, a serum level of a factor indicative of cytokine-release syndrome (CRS) in the subject is less than about 10 times, less than about 25 times, and/or less than about 50 times the serum level of said indicator in the subject immediately prior to said previous dose and the subject does not exhibit a detectable adaptive host immune response specific for the CAR expressed by the cells of said previous dose; and/or the time between said previous and consecutive doses is greater than about 14 days and less than about 28 days.

57. The method of embodiment 56, wherein the number of cells in the consecutive dose of CAR-expressing cells comprises between about $2 \times 10^6$ cells per kilogram (cells/kg) body weight and about $6 \times 10^6$ cells/kg, between about $2.5 \times 10^6$ cells/kg and about $5.0 \times 10^6$ cells/kg, or between about $3.0 \times 10^6$ cells/kg and about $4.0 \times 10^6$ cells/kg, each inclusive.

58. The method of any of embodiments 1-57, wherein the disease or condition is a leukemia or lymphoma.

59. The method of any of embodiments 1-58, wherein the disease or condition is acute lymphoblastic leukemia.

60. The method of embodiment 59, wherein the number of CAR$^+$ cells per kilogram administered in the consecutive dose is greater than the number of CAR$^+$ cells per kilogram administered in the first dose.

61. The method of embodiment 60, wherein the number of CAR$^+$ cells per kilogram administered in the consecutive dose is at least at or about 2 times or at or about 3 times greater than the number of CAR$^+$ cells per kilogram administered in the first dose.

62. The method of any of embodiments 1-58, wherein the disease or condition is a non-Hodgkin lymphoma (NHL).

63. The method of any of embodiments 1-62, wherein the number of CAR$^+$ cells administered in the first dose is at or about or no more than at or about $1 \times 10^6$ per kilogram of the subject and/or the number of CAR$^+$ cells administered in the consecutive dose is at or about $3 \times 10^6$ per kilogram of the subject.

64. The method of embodiment 62, wherein the number of CAR$^+$ cells per kilogram administered in the consecutive dose is less than or about less than or is the same or about the same as the number of CAR$^+$ cells per kilogram administered in the first dose.

65. The method of any of embodiments 1-64, further comprising administering to the subject one or more additional subsequent doses, wherein the first of said one or more additional subsequent doses is administered at a time that is at least or greater than 14 days after the initiation of the administration of the consecutive dose.

66. The method of embodiment 65, wherein the administration of the first, consecutive and subsequent doses comprises administering at least three of the doses within at or about 28 days.

67. The method of embodiment 65 or 66, wherein the consecutive dose is administered at about day 14 following the initiation of administration of the first dose, one of the at least one additional subsequent doses is administered at day 28 following the initiation of administration of the first dose, and optionally wherein additional subsequent doses are administered at day 42 and/or day 56 following the initiation of administration of the first dose.

68. The method of any of embodiments 1-67, wherein the cells are T cells.

69. The method of any of embodiments 1-68, wherein the T cells are autologous to the subject.

70. Use of a composition comprising cells expressing a chimeric antigen receptor (CAR) for manufacture of a medicament for treatment of a disease or condition in a subject previously treated with CAR-expressing cells, wherein:

the composition is for use 14 to 28 days after the previous treatment; and/or the composition is formulated for administration of a consecutive dose in an amount sufficient for reduction in burden of a disease or condition in the subject having been previously treated with the CAR-expressing cells.

71. Cells expressing a chimeric antigen receptor (CAR) for use in treating a disease in a subject previously treated with CAR-expressing cells, wherein:

the cells are for use between about 14 and 28 days after the previous treatment; and the cells are formulated for administration of a consecutive dose in an amount sufficient for reduction in burden of a disease or condition in the subject having been previously treated with the CAR-expressing cells.

72. The use of embodiment 70 or cells of embodiment 71, wherein the subject does not exhibit morphologic disease and/or the subject does not exhibit greater than 5% blast cells in the bone marrow.

73. Use of cells expressing a chimeric antigen receptor (CAR) in the manufacture of a medicament for use in a method for treating a disease or condition, said method comprising:

(a) administering to a subject having the disease or condition a first dose of cells expressing the CAR, said first dose comprising no more than about $1 \times 10^6$ of the cells per kilogram body weight of the subject, no more than about $1 \times 10^8$ of the cells, and/or no more than about $1 \times 10^8$ of the cells/m$^2$ of the subject; and (b) administering to the subject a consecutive dose of cells expressing a CAR at a time point that is at least or more than about 14 days after and less than about 28 days after initiation of said administration in (a).

74. Cells expressing a chimeric antigen receptor (CAR) for use in a method for treating a disease or condition, said method comprising:

(a) administering to a subject having the disease or condition a first dose of cells expressing the CAR, said first dose comprising no more than about $1 \times 10^6$ of the cells per kilogram body weight of the subject, no more than about $1 \times 10^8$ of the cells, and/or no more than about $1 \times 10^8$ of the cells/m$^2$ of the subject; and (b) administering to the subject a consecutive dose of cells expressing a CAR at a time point that is at least or more than about 14 days after and less than about 28 days after initiation of said administration in (a).

75. The use or cells of any of embodiments embodiment 70-74, wherein the cells are formulated for administration in an amount that (i) does not induce severe CRS in the subject or does not induce CRS in the subject; (ii) does not induce grade 3 or higher neurotoxicity in the subject; (iii) based on clinical data, does not induce severe CRS in a majority of subjects so-treated; and/or (iv) based on clinical data, does not induce grade 3 or higher neurotoxicity in a majority of subjects so-treated.

76. Use of cells expressing a chimeric antigen receptor (CAR) for manufacture of a medicament for the treatment of a disease or condition in a subject, wherein the cells are formulated and/or packaged for administration to the subject in a first and a consecutive dose and/or the treatment comprises administering the cells to the subject in a first and a consecutive dose, wherein:

the first dose comprises no more than about $1 \times 10^6$ of the cells per kilogram body weight of the subject, no more than about $1 \times 10^8$ of the cells, and/or no more than about $1 \times 10^8$ of the cells/m$^2$ of the subject, and the consecutive dose is for administration at a time point (a) that is at least or more than about 14 days after and less than about 28 days after initiation of the first administration, and/or (b) at which (i) the serum level in the subject of a factor indicative of cytokine release syndrome (CRS) is less than about 10 times, less than about 25 times, and/or less than about 50 times that in the subject immediately prior to said first administration; (ii) the subject does not exhibit grade 3 or higher neurotoxicity; (iii) a CRS-related outcome or symptom of neurotoxicity in the subject following said administration of said first dose has reached a peak level and begun to decline following the first administration, and/or (iv) the subject does not exhibit a detectable humoral or cell-mediated immune response against the CAR expressed by the cells of said first dose.

77. Cells expressing a chimeric antigen receptor (CAR) for use in treatment of a disease or condition in a subject, wherein the cells are formulated and/or packaged for administration to the subject in a first and a consecutive dose and/or the treatment comprises administering the cells to the subject in a first and a consecutive dose, wherein:

the first dose comprises no more than about $1 \times 10^6$ of the cells per kilogram body weight of the subject, no more than about $1 \times 10^8$ of the cells, and/or no more than about $1 \times 10^8$ of the cells/m² of the subject, and the consecutive dose is for administration at a time point (a) that is at least or more than about 14 days after and less than about 28 days after initiation of the first administration, and/or (b) at which (i) the serum level in the subject of a factor indicative of cytokine release syndrome (CRS) is less than about 10 times, less than about 25 times, and/or less than about 50 times that in the subject immediately prior to said first administration; (ii) the subject does not exhibit grade 3 or higher neurotoxicity; (iii) a CRS-related outcome or symptom of neurotoxicity in the subject following said administration of said first dose has reached a peak level and begun to decline following the first administration, and/or (iv) the subject does not exhibit a detectable humoral or cell-mediated immune response against the CAR expressed by the cells of said first dose.

78. The use or cells of any of embodiments 73-77, wherein the first and consecutive administrations comprise administering the cells in one or more unit dose, each unit dose comprising about between $5 \times 10^7$ of the cells and about $5 \times 10^8$ cells, about between $5 \times 10^7$ of the cells and about $2.5 \times 10^8$ cells or about between $2.5 \times 10^8$ cells and $4 \times 10^8$ cells; or the cells are formulated in a unit dose comprising no more than about $5 \times 10^7$ cell, no more than about $1 \times 10^8$ cells, no more than about $2 \times 10^8$ of the cells, no more than about $2.5 \times 10^8$ of the cells, no more than about $3.0 \times 10^8$ of the cells or no more than about $4 \times 10^8$ of the cells.

79. The use or cells of embodiment 78, wherein the first administration comprises administering a single unit dose.

80. The use or cells of embodiment 78 or embodiment 79, wherein the consecutive administration comprises administration of two or more unit doses.

81. The use or cells of embodiment 78 or embodiment 79, wherein the consecutive administration comprises administration a single unit dose.

82. The use, composition or cells of any of embodiments 68-81, wherein the disease or condition is a tumor or a cancer.

83. The use, composition or cells of embodiment 82, wherein the tumor or cancer is leukemia or lymphoma.

84. The use, composition or cells of any of embodiments 68-83, wherein the consecutive dose is formulated for administration of an increased number of CAR-expressing cells as compared to the first dose or previous dose.

85. The use, composition or cells of embodiment 84, wherein the composition is for use in treating acute lymphoblastic leukemia.

86. The use, composition or cells of any of embodiments 68-83, wherein the consecutive dose is formulated for administration of less than or about the same number of CAR-expressing cells as the number of CAR-expressing cells in the previous dose.

87. The use, composition or cells of embodiment 84 or embodiment 86, wherein the composition is for use in treating non-Hodgkin lymphoma (NHL).

88. An article of manufacture, comprising:
a plurality of sealable containers, each individually comprising a unit dose of cells expressing a chimeric antigen receptor (CAR) for administration to a subject, said unit dose comprising about $1 \times 10^8$ of the cells, no more than about $1 \times 10^8$ of the cells, about $5 \times 10^7$ of the cells, no more than about $5 \times 10^7$ of the cells, about $1 \times 10^6$ cells per kg of the subject, or no more than about $1 \times 10^6$ of the cells per kg of the subject;
packaging material; and
a label or package insert comprising instructions for administering a plurality of said unit doses to the subject by carrying out a first administration and a consecutive administration, said first administration comprising delivering one of said unit doses to the subject and said consecutive administration comprising administering one or a plurality of said unit doses to the subject.

89. The article of manufacture of embodiment 88, wherein the instructions specify that said consecutive administration is to be carried out at a time between about 14 or 15 and 27 days, optionally at about day 17 or about day 21, following said first administration.

90. The article of manufacture of embodiment 88 or embodiment 89, wherein the instructions specify that said consecutive administration is to be carried out at a time after which it has been determined that a serum level of a factor indicative of cytokine-release syndrome (CRS) in the subject is less than about 10 times, less than about 25 times, and/or less than about 50 times the serum level of said indicator in the subject immediately prior to said first administration.

91. The article of manufacture of any of embodiments 88-90, wherein the instructions specify that said consecutive administration is to be carried out at a time after which it has been determined that an indicator of CRS has peaked and is declining, and/or that the subject does not exhibit a detectable adaptive host immune response specific for the CAR expressed by the cells of said first dose.

92. The article of manufacture of any of embodiments 88-91, wherein the cells have been derived from the subject.

93. The article of manufacture of any of embodiments 88-92, wherein said label and/or said packaging material further comprises an identifier specific to the subject, indicating that the cells were derived from the subject and/or should be administered to the subject specifically.

94. The article of manufacture of any of embodiments 88-93, wherein the containers are or comprise flexible cell infusion bags.

95. A method of treatment, comprising:
a) assessing a factor indicative of disease burden in a subject having or suspected of having a tumor; and
b) based on the result of the assessment, determining the dose of cells expressing a chimeric antigen receptor (CAR) to be administered to the subject, wherein:

i) if the assessment determines that the subject does not have morphologic disease or does not have substantial morphologic disease or does not have a disease burden at or above a threshold level, administering to the subject a dose of CAR-expressing cells greater than $1 \times 10^6$ cells/kg; and ii) if the assessment determines that the subject has morphologic disease or substantial morphologic disease or a disease burden at or above a threshold level, administering to the subject a dose of CAR-expressing cells that is relatively lower as compared to in ii).

96. The method of embodiment 95, wherein:
the subject does not exhibit morphologic disease or substantial morphologic disease or a disease burden at or above a threshold level and is administered a dose of cells that is greater than or about $2 \times 10^6$ cells/kg, $3 \times 10^6$ cells/kg, $4 \times 10^6$ cells/kg, $5 \times 10^6$ cells/kg, $6 \times 10^6$ cells/kg, $7 \times 10^6$ cells/kg, $8 \times 10^6$ cells/kg, $9 \times 10^6$ cells/kg, $1 \times 10^7$ cells/kg or $2 \times 10^7$ cells/kg; and/or
the subject exhibits morphologic disease or substantial morphologic disease or has a disease burden above a threshold level and is administered a dose of cells that is less than or less than about $1 \times 10^6$ cells/kg or $5 \times 10^6$ cells/kg.

97. The method of embodiment 95 or embodiment 96, wherein the subject exhibits morphologic disease and/or substantial morphologic disease and/or the disease burden is at or above a threshold level if there are greater than or equal to or about 5% blasts in the bone marrow, greater than or equal to or about 10% blasts in the bone marrow, greater than or equal to or about 15% blasts in the bone marrow or greater than or equal to or about 20% blasts in the bone marrow.

98. The method of any of embodiments 95 to 97, wherein:
if the subject exhibits less than or less than about 5% blasts the subject is administered a dose of cells of greater than or about $1 \times 10^6$ cells/kg $2 \times 10^6$ cells/kg, $3 \times 10^6$ cells/kg, $4 \times 10^6$ cells/kg, $5 \times 10^6$ cells/kg, $6 \times 10^6$ cells/kg, $7 \times 10^6$ cells/kg, $8 \times 10^6$ cells/kg, $9 \times 10^6$ cells/kg, $1 \times 10^7$ cells/kg or $2 \times 10^7$ cells/kg and/or if the subject exhibits greater than or equal to or about 5% blasts the subject is administered a dose of cells that is less than about $1 \times 10^6$ cells/kg or $5 \times 10^6$ cells/kg;
if the subject exhibits less than or less than about 10% blasts the subject is administered a dose of cells of greater than or about $1 \times 10^6$ cells/kg $2 \times 10^6$ cells/kg, $3 \times 10^6$ cells/kg, $4 \times 10^6$ cells/kg, $5 \times 10^6$ cells/kg, $6 \times 10^6$ cells/kg, $7 \times 10^6$ cells/kg, $8 \times 10^6$ cells/kg, $9 \times 10^6$ cells/kg, $1 \times 10^7$ cells/kg or $2 \times 10^7$ cells/kg and/or if the subject exhibits greater than or equal to or about 10% blasts the subject is administered a dose of cells that is less than about $1 \times 10^6$ cells/kg or $5 \times 10^6$ cells/kg;
if the subject exhibits less than or less than about 15% blasts the subject is administered a dose of cells of greater than or about $1 \times 10^6$ cells/kg $2 \times 10^6$ cells/kg, $3 \times 10^6$ cells/kg, $4 \times 10^6$ cells/kg, $5 \times 10^6$ cells/kg, $6 \times 10^6$ cells/kg, $7 \times 10^6$ cells/kg, $8 \times 10^6$ cells/kg, $9 \times 10^6$ cells/kg, $1 \times 10^7$ cells/kg or $2 \times 10^7$ cells/kg and/or if the subject exhibits greater than or equal to or about 15% blasts the subject is administered a dose of cells that is less than about $1 \times 10^6$ cells/kg or $5 \times 10^6$ cells/kg;
if the subject exhibits less than or less than about 20% blasts the subject is administered a dose of cells of greater than or about $1 \times 10^6$ cells/kg $2 \times 10^6$ cells/kg, $3 \times 10^6$ cells/kg, $4 \times 10^6$ cells/kg, $5 \times 10^6$ cells/kg, $6 \times 10^6$ cells/kg, $7 \times 10^6$ cells/kg, $8 \times 10^6$ cells/kg, $9 \times 10^6$ cells/kg, $1 \times 10^7$ cells/kg or $2 \times 10^7$ cells/kg and/or if the subject exhibits greater than or equal to or about 20% blasts the subject is administered a dose of cells that is less than about $1 \times 10^6$ cells/kg or $5 \times 10^6$ cells/kg.

99. The method of any of embodiments 95 to 98, wherein the tumor is a leukemia or lymphoma, optionally a B cell-derived leukemia or lymphoma.

100. The method of any of embodiments 95 to 99, wherein the subject does not exhibit cytokine release syndrome (CRS), does not exhibit severe CRS, does not exhibit neurotoxicity, does not exhibit severe neurotoxicity, or does not exhibit neurotoxicity above grade 3 following administration of the dose of cells.

101. The method of any of embodiments 95 to 100, wherein the administration in (a) leads to a reduction in burden of the disease or condition in the subject, as indicated by a reduction in one or more factors indicative of disease burden following said administration in (a).

102. The method of any of embodiments 95 to 101, further comprising administering one or more consecutive doses to the subject.

EXAMPLES

The following examples are included for illustrative purposes only and are not intended to limit the scope of the invention.

Example 1: Treatment of Cancer Patients with First and Consecutive Doses of CAR-Expressing Autologous T Cells T cells are isolated from peripheral blood of human subjects with cancer by immunoaffinity-based enrichment and the cells cultured and transduced with viral vectors encoding a chimeric antigen receptor (CAR) that specifically binds to an antigen expressed by the cancer in the subject, which is a tumor-associated or tumor-specific antigen. The cells are cryopreserved in infusion medium in individual flexible infusion bags, each containing a single unit dose of the cells, which is about $1 \times 10^6$ cells per kilogram body weight of the subject or about $5 \times 10^5$ cells per kilogram body weight of the subject. The cells are maintained at a temperature below $-130°$ C. prior to infusion.

Prior to initiation of cell therapy, blood is obtained from the subjects and, optionally, the levels of one or more serum factors indicative of cytokine release syndrome (CRS) such as tumor necrosis factor alpha (TNFα), interferon gamma (IFNγ), and IL-6, are assessed in the serum by ELISA. Tumor burden is optionally assessed by measurement of the size or mass of a solid tumor, such as by PET or CT scan, or by assessing the number of cells of the patient associated with the cancer, such as in the bone marrow or peripheral blood, before treatment begins.

The cells are thawed at bedside by warming to approximately 37° C. and subjects administered a first dose of the cells by single infusion. The amount of the first dose is a single unit dose. For subjects deemed to have low tumor burden, two unit doses may be administered in the first dose. The first dose is administered intravenously (IV) by continuous infusion, over a period of approximately 15 to 30 minutes.

Following administration of the first dose, the subjects receive physical examinations and are monitored for any symptoms of toxicity or toxic outcomes, such as fever, hypotension, hypoxia, neurologic disturbances, or an increased serum level of an inflammatory cytokine or C reactive protein (CRP). Optionally, following administration of the first dose, on one or more occasions, blood is obtained from the patients and the levels of serum factors indicative of CRS are assessed by ELISA. The levels of the serum factors are compared to those obtained immediately prior to administration of the first dose. If necessary, anti-IL6 or other CRS therapy is administered to reduce signs of CRS.

The presence or absence of an anti-CAR immune response in the subject is optionally detected following the administration of the first dose, for example, at 1, 2, 3, and/or 4 weeks following the initiation of the administration, for example, by ELISA, ELISPOT, cell-based antibody assay, and/or mixed-lymphocyte reaction.

The percent reduction in tumor burden achieved by the first dose is optionally measured on one or more occasions following administration of the first dose by scans, such as PET and CT scans, in patients with solid tumors, and/or by quantifying disease-positive cells in blood or tumor sites, e.g., in subjects with hematological cancers, and comparing the values to those observed immediately prior to the first dose.

A consecutive dose is administered. In some subjects, the consecutive dose is administered in 21 days following the initiation of the administration of the first dose. In some cases, the consecutive dose is only administered if the level of a tested CRS-related outcome or serum factor is below an acceptable level and if no anti-CAR immune response is detected in the subject at 21 days following the first dose administration. In other subjects, the consecutive does is administered at a time that is greater than 3 days following the administration of the first dose, and at which the subject is deemed to not have CRS or severe CRS, or at which levels of all tested serum factors indicative of CRS are below 20% of that observed at a peak following the first dose administration, and the subject is deemed not to have a detectable anti-CAR immune response.

The size of the consecutive dose is patient-specific, and is based on tumor burden, presence of an anti-CAR immune response, and level of CRS-related outcomes. Some patients are administered a consecutive dose containing 1, 2, 3, or even more unit doses of the cells. The consecutive dose is administered by continuous infusion, IV, over approximately 15 to 30 minutes.

Beginning after the first dose and continuing for up to several years, the subjects are monitored on a regular basis. Development of an anti-CAR immune response is assessed and tumor burden is measured. Optionally, during follow-up visits, the CAR-expressing cells are detected by flow cytometry and quantitative polymerase chain reaction (qPCR) to measure in vivo proliferation and persistence of the administered cells.

Example 2: Assessment of Neurotoxicity of CAR-T Cell Treatment in Subjects Having Morphological Disease Prior to Treatment Subjects with CD19+ B cell acute lymphoblastic leukemia (ALL) were administered autologous T cells expressing an anti-CD19 chimeric antigen receptor (CAR). The CAR included a truncated EGFR (EGFRt) portion as a marker. Prior to administration of the cells, patients underwent leukapheresis and were treated with chemotherapy. To generate the autologous CAR-expressing T cells, T cells were isolated by immunoaffinity-based enrichment from leukapheresis samples from individual subjects, activated and transduced with a viral vector encoding an anti-CD19 CAR. The cells were expanded, frozen, and thawed at bedside prior to administration.

Tumor burden was assessed prior to treatment by evaluating bone marrow and the percent of bone marrow blasts was determined. Subjects having at least 5% blasts in bone marrow were deemed to have morphological disease (MD). Subjects exhibiting complete remission (CR) as defined below, including having less than 5% blasts in the bone marrow, but showing molecularly detectable disease in the bone marrow (by flow cytometry) were deemed to have minimal residual disease (MRD). CAR-expressing T cells were administered to subjects by single intravenous (IV) continuous infusion, over approximately 15-30 minutes, at varying doses ranging from about or approximately $0.9 \times 10^6$ CAR+ cells/kg to about or approximately $5.6 \times 10^6$ CAR+ cells/kg (see FIG. 1A-C). Cyclophosphamide was administered to subjects as a preconditioning chemotherapeutic treatment 2 to 7 days before cell infusion.

Disease status of subjects (MRD or MD) was assessed subsequent to administration of CAR-expressing T cells to assess response to treatment. Complete remission (CR) was determined in subjects if there was a restoration of normal hematopoiesis with neutrophil count $>1,000 \times 10^6$/L, platelet count of $>100,000 \times 10^6$/L and hemoglobin $>10$ g/dL; $<5$% blasts present in a post-treatment bone marrow differential; and no clinical evidence of leukemia for a minimum of four weeks. Following treatment, subjects also were assessed and monitored for neurotoxicity (neurological complications including symptoms of confusion, aphasia, seizures, convulsions, lethargy, and/or altered mental status), graded based on severity (using a Grade 1-5 scale (see, e.g., Guido Cavaletti & Paola Marmiroli *Nature Reviews Neurology* 6, 657-666 (December 2010), with grade 3 (severe symptoms), 4 (life-threatening symptoms) or 5 (death) being deemed severe neurotoxicity. Cytokine release syndrome (CRS) also was determined and monitored, graded based on severity.

Response, presence of severe CRS, and presence of severe neurotoxicity following treatment with a single infusion of varying doses of CAR-expressing T cells, compared to dosage, were assessed in groups of subjects separated based on disease burden prior to treatment. Results are shown in FIGS. 1A-C.

Figure 1B:
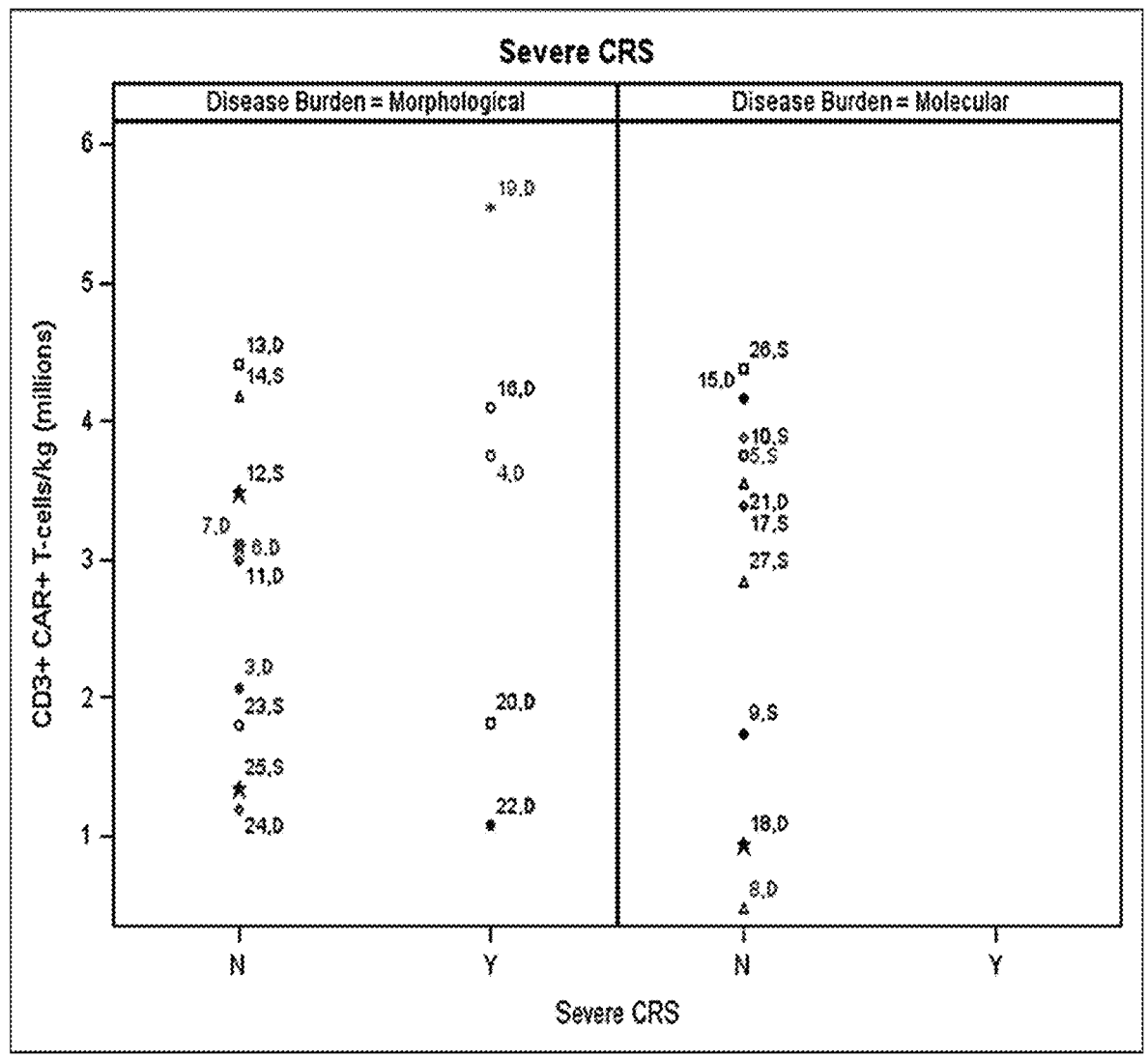
FIG. 1B shows the presence (Y) or absence (N) of severe cytokine release syndrome (CRS) in subjects with morphological or molecular disease (disease burden at time of treatment initiation) treated with a single infusion of varying doses of CAR-expressing T cells.

As shown in FIG. 1A, complete remission (CR) was observed in the majority of subjects treated with CAR-expressing T cells at all doses tested, regardless of disease burden (morphological or molecularly detectable disease) prior to treatment. CRS was observed primarily in subjects classified as having morphological disease prior to treatment. The results depicted in FIG. 1B, however, show that within this group, the presence of CRS was observed for subjects having received various dosage levels of CAR-expressing T cells.

Figure 1C:
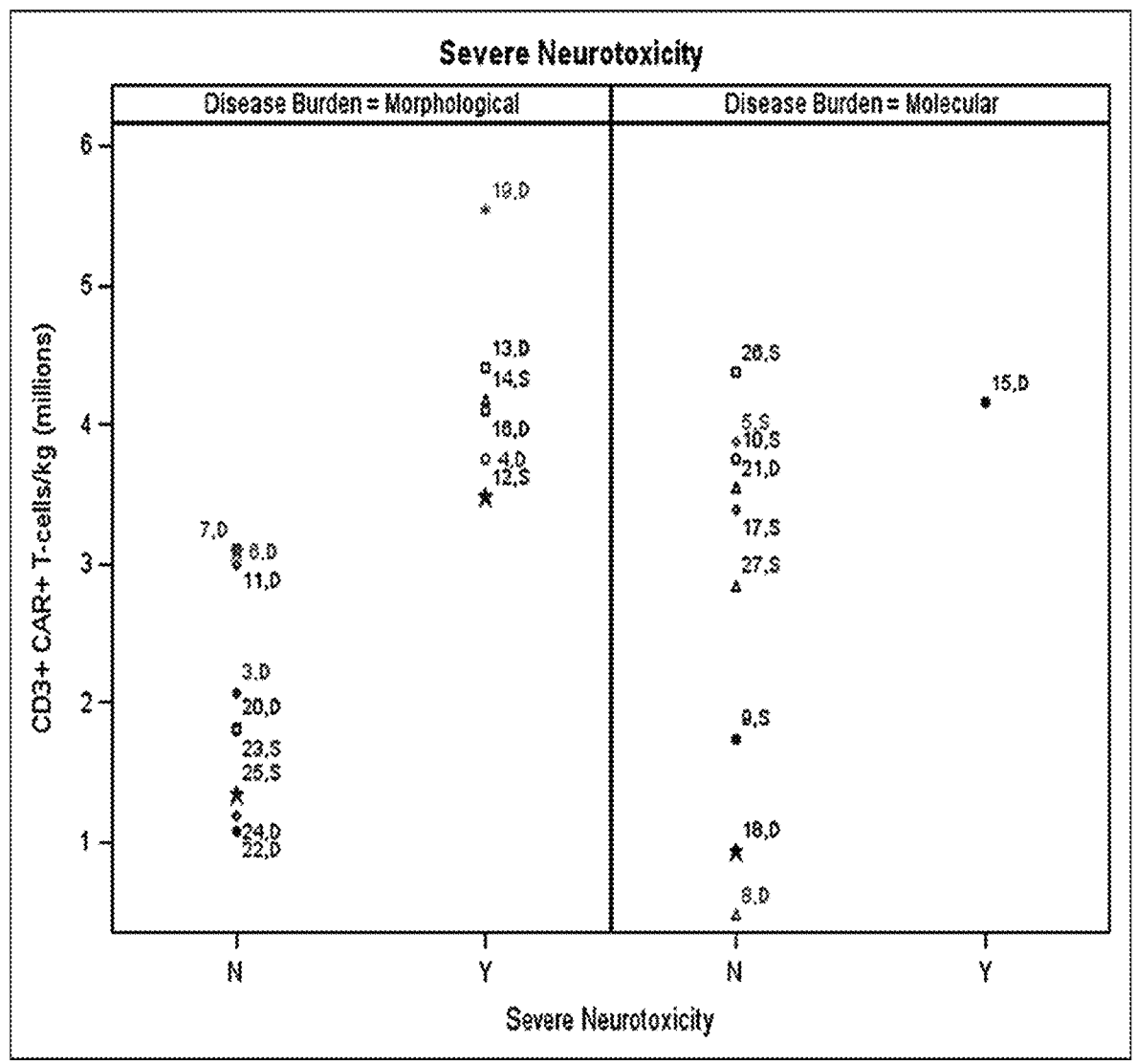
FIG. 1C shows the presence (Y) or absence (N) of severe neurotoxicity in subjects with morphological or molecular disease (disease burden at time of treatment initiation) treated with a single infusion of varying doses of CAR-expressing T cells.

As shown in FIG. 1C, severe neurotoxicity also was most frequently observed in subjects with morphological disease as composed to minimal residual disease prior to treatment in contrast to the results for CRS, however, neurotoxicity was observed only in those subjects receiving higher doses. Subjects analyzed in this study who had received a dose of CAR-expressing T cells lower than about $3.5 \times 10^6$ cells/kg, did not exhibit severe neurotoxicity after treatment. With one exception, severe neurotoxicity was generally not observed in subjects classified as having molecularly detectable disease prior to treatment. Thus, subjects receiving a lower dose of administered T cells and/or who had a lower disease burden prior to treatment did not generally exhibit severe neurotoxicity.

These results support, in order to minimize toxicity and maximize efficacy, using a dosage regime that includes administering to subjects, including those with morphologic disease, a first low dose of CAR-expressing T cells (which may not necessarily be sufficient to eradicate disease in all or most subjects) to reduce disease burden, followed by a consecutive or subsequent dose of cells after tumor burden has been reduced. The results also support a conclusion that if desired or needed in a particular disease or context (for example, to promote an increased response or efficacy), the consecutive or subsequent administration of cells (given after reduction in tumor burden, at which point all or most subjects should exhibit minimal disease), the consecutive dose can be carried out at a higher dose, without or with minimal risk of severe neurotoxicity.

Example 3: Assessment of Efficacy and Toxicity Following First and Consecutive Doses of CAR$^+$ Autologous T Cells Treatment efficacy and toxic effects were assessed in a subset of subjects in the study described in Example 2 who were administered multiple doses of the CAR$^+$ T cells. Table 3 below sets forth the particular dosages of cells administered in the various multiple doses, and in each case, the time that elapsed between the first and consecutive dose. Table 3 also sets forth each subject's tumor burden (MRD or MD with % of blast cells in bone marrow; listed under the column labeled "Disease burden") as assessed prior to administration of each dose, based on criteria as described in Example 2. Table 3 also lists results for each patient for response to each administration (under the column "Response," listing the tumor burden following administration, which as compared to the pre-administration disease burden, indicates response to treatment), presence or absence (Y/N) of severe CRS and severe neurotoxicity as described in Example 2.

The results in Table 3 show that a majority of treated subjects were responsive to the first dose of cells as evidenced by a reduction in tumor burden in the subject, for example, reduction in tumor burden from presence of >5% of blast cells to MRD$^+$ or in some cases MRD$^-$, or from MRD$^+$ to MRD$^-$. Complete remission (CR) of some subjects also was observed. As shown in Table 3, tumor reduction also was observed for subjects following administration of a consecutive dose of cells as evidenced by complete remissions or disease reduction as assessed from flow cytometric analysis for presence of MRD (see patient ID No. 1, 2, 7, 8 and 9). Thus, this result demonstrates that administration of the consecutive dose of cells also was efficacious. Most subjects did not exhibit severe CRS at any of the doses. Further, consistent with Example 2 severe neurotoxicity was observed to occur following administration only in subjects who had received higher doses of CAR-expressing cells and generally only in subjects with morphologic disease.

In some cases, Table 3 demonstrates that some subjects were not responsive (NR) to the first dose (see patient ID No. 5 and ID No. 2*) so that a reduction in disease or tumor burden levels was not achieved. Further, the results show that such failure to achieve clinical remission after infusion of the first dose did not increase the risk or frequency of neurotoxicity in the subject when administered a consecutive higher dose, since severe neurotoxicity was not detected after receiving a consecutive higher dose in either of these subjects.

In some embodiments, lack of (or relatively lower) degrees of responsiveness or toxicity in a subject indicates that the subject may not have responded well to CAR$^+$ T cell therapy, but is also not at risk for certain toxic adverse events upon another infusion, which may otherwise indicate a need

TABLE 3

Safety and Efficacy of First and Consecutive CAR$^+$ T Cell Doses

| | First Dose | | | | Days | Consecutive Dose | | | | |
|---|---|---|---|---|---|---|---|---|---|---|
| ID | Disease burden | Dose × 10$^6$/kg | Severe CRS | Severe Neurotoxicity | Response | between doses | Disease burden | Dose × 10$^6$/kg | Severe CRS | Severe Neurotoxicity | Response |
| 1 | MRD+ [2%] | 1.74 | N | N | MRD– CR | 133 | MRD+ [2%] | 1.37 | N | N | MRD– CR |
| 2 | 6% | 3.08 | N | N | MRD– CR | 86 | MRD+ [3%] | 1.50 | N | N | MRD– CR |
| 2* | 90% | 4.27 | N | N | 48% | 23 | 56% | 3.27 | N | N | NR |
| 4 | MRD+ [4%] | 0.47 | N | N | MRD+ CR | 203 | MRD+ [3%] | 3.84 | N | N | MRD+ |
| 5 | 97% | 2.99 | N | N | NR | 15 | 75% | 3.80 | N | N | NR |
| 6 | 60% | 3.48 | N | Y | MRD– CR | 414 | MRD+ [2%] | N/A | N | N | MRD– CR |
| 7 | MRD+ | 4.15 | N | Y | MRD+ | 103 | MRD+ | 4.53 | N | N | MRD– CRi |
| 8 | 85% | 4.10 | Y | Y | MRD– CR | 104 | 15% | 4.27 | N | Y | MRD– CR |
| 9 | 25% | 1.79 | N | N | MRD+ [2%] | 79 | 87% | 1.98 | N | N | CR |

*3$^{rd}$ dose; subject in CR following 1$^{st}$ and 2$^{nd}$ doses
ID: Subject Number
MRD: Minimal Residual Disease
CR: complete remission
Cri: complete remission with incomplete blood count recovery
NR: No response
N/A: not available
N: No
Y: Yes to avoid higher doses for subsequent administration. Therefore, these results support a dosage regime (e.g., if desired or necessary for maximizing or improving efficacy) in which a first low dose administration is followed (e.g., in a relatively short time) by a consecutive administration, carried out using a higher dose as compared to the first dose. The results presented here show that even if certain subjects do not respond well to the first dose (and thus do not have low tumor burden at the time of the consecutive dose) the risk of severe neurotoxicity is low upon administration of the consecutive dose, even for these non-responding subjects.

Figure 2:
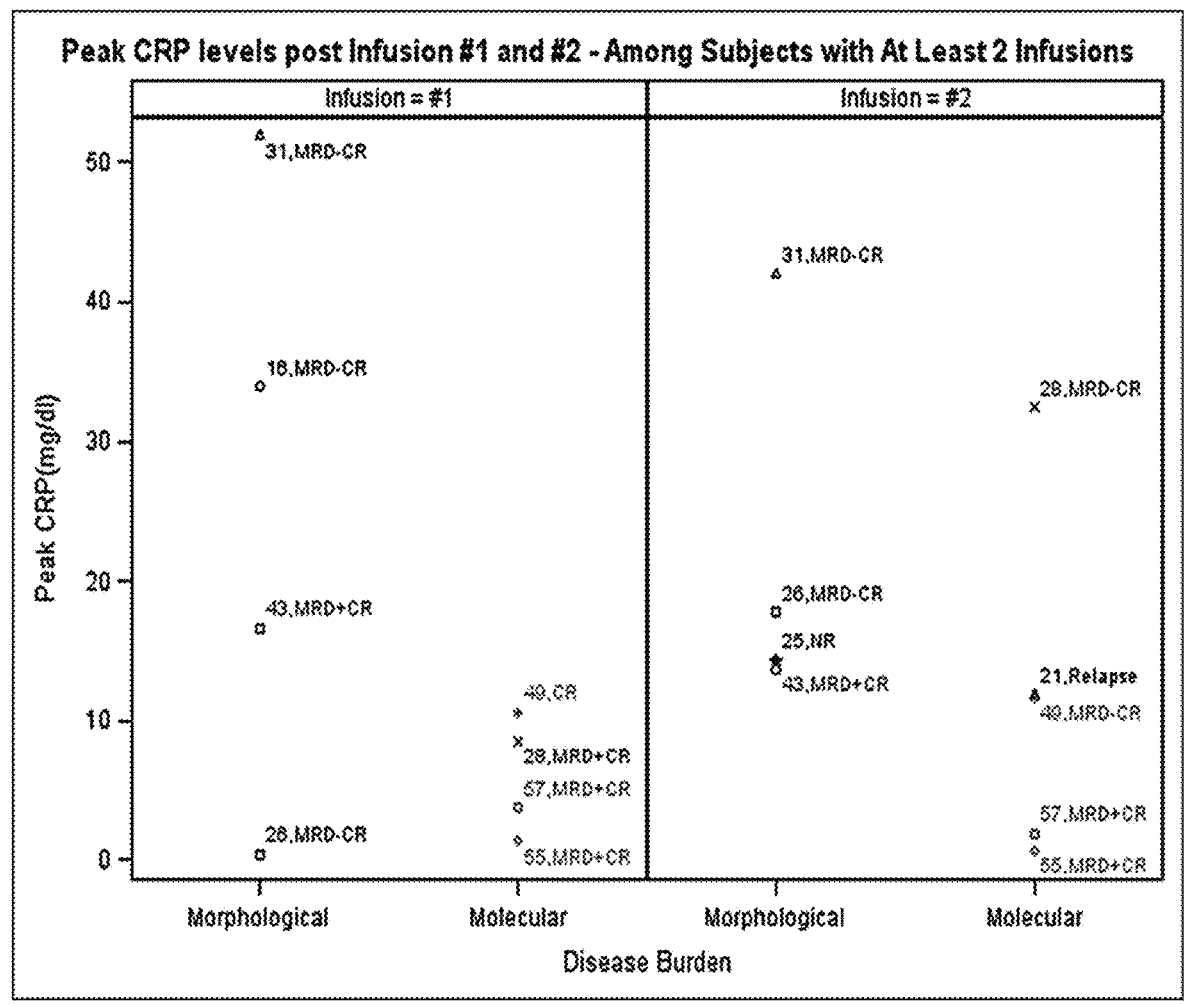
FIG. 2 shows peak C reactive protein (CRP) levels in subjects exhibiting morphological or molecular disease at the time of administration of a first dose (Infusion=#1) (left-hand panel) and in subjects exhibiting morphological or molecular disease at the time of administration of a consecutive dose (Infusion=#2) (right-hand panel) of CAR-expressing T cells. Numbers and text/abbreviations (e.g., "MRD–CR", "MRD+CR," etc.) shown next to individual data points reflect patient numbers and disease burden following the indicated infusion. MRD+=minimum residual disease; MRD–=no minimum residual disease; CR=complete remission.

To further assess efficacy of cells administered in the first and consecutive dose, biological activity of administered cells was compared based on peak levels of measurements that were taken of serum levels of C reactive protein (CRP). Elevated peak levels of CRP in serum were taken as evidence of T cell expansion following infusion. The results are set forth in FIG. 2. The results show evidence of cell expansion after infusion of both a first and consecutive dose of T cells. Thus, these results show that, while subjects exhibited reduced CRS and neurotoxicity following a consecutive as opposed to a first administration of CAR+ T cells, the biological activity of the cells administered in and their ability to expand was comparable in each administration.

Subjects in the study also received physical examinations and were monitored for symptoms of other adverse events (AE), including those set forth in Table 4. To assess differences between first and consecutive administrations of CAR+ T cells in subjects, these data were compared. A treatment emergent AE (TEAE) after infusion of the first dose was defined as any AE occurring within 30 days after receiving the first dose but prior to receiving the consecutive dose. A TEAE after infusion of the consecutive dose was defined as any AE occurring within 30 days after receiving the consecutive dose but prior to any subsequent dose. Table 4 sets forth the number of subjects that exhibited a TEAE and the percentage (in parenthesis) of subjects exhibiting such TEAE compared to the number of total subjects assessed for the same TEAE. The results show that the percentage of adverse events was comparable following infusion of the first dose and consecutive dose.

TABLE 4

Adverse Events

| Adverse Event | TEAE post-infusion dose #1 (n = 33) | TEAE post-infusion dose #2 (n = 11) |
| --- | --- | --- |
| All | 30 (90.9) | 8 (72.7) |
| Febrile neutropenia | 15 (45.5) | 2 (18.2) |
| Abdominal pain | 3 (9.1) | 1 (9.1) |
| Nausea | 8 (24.2) | 1 (9.1) |
| Chills | 10 (30.3) | 1 (9.1) |
| Pyrexia | 12 (36.4) | 3 (27.3) |
| Cytokine release syndrome (CRS) | 5 (15.2) | 1 (9.1) |
| Alanine aminotransferase increased | 3 (9.1) | 1 (9.1) |
| Aspartate aminotransferase increased | 2 (6.1) | 1 (9.1) |
| Hyperglycaemia | 5 (15.2) | 1 (9.1) |
| Hypophosphataemia | 14 (42.5) | 1 (9.1) |
| Hypophosphataemia | 14 (42.5) | 1 (9.1) |
| Muscular weakness | 3 (9.1) | 1 (9.1) |
| Convulsion | 6 (18.2) | 1 (9.1) |
| Dizziness | 2 (6.1) | 1 (9.1) |
| Encephalopathy | 9 (27.3) | 1 (9.1) |

TABLE 4-continued

Adverse Events

| Adverse Event | TEAE post-infusion dose #1 (n = 33) | TEAE post-infusion dose #2 (n = 11) |
| --- | --- | --- |
| Dermatitis acneiform | 0 (0.0) | 1 (9.1) |
| Hypotension | 12 (36.4) | 1 (9.1) |

Example 4: Impact of CAR+ T Cell Dose on Overall Survival of Different Subject Populations To further assess the impact of CAR+ T cell dose on overall treatment of subjects, overall survival of subjects in the study described in Example 2 was compared between small groups of subjects, separated based upon number of cells administered and disease state at the time of administration. Product-limit survival was determined by calculating the Kaplan-Meier estimate with censored observations, such as occurred, for example, if a patient withdrew from the study.

Comparing all subjects in a group of subjects who had been administered a dose of fewer than $2.5 \times 10^6$ CAR+ cells/kg and all subjects in another group of subjects who had been administered a dose with greater than $2.5 \times 10^6$ CAR+ T cells/kg, the results indicated an overall survival advantage for the group of subjects administered the higher dose. Looking just at subjects having morphologic disease at the time of administration, the observed effect on overall survival with a higher dose was even greater. Collectively, the results presented herein support a dosage regime in which a higher dose (as compared to a first dose) is used in a consecutive administration, when the consecutive dose is given at a time at which disease burden remains reduced in patients on average, but at which the risk of CRS and/or neurotoxicity remains low. The results in this example support a conclusion that use of a higher consecutive dose will promote increased efficacy. Moreover, as noted, the results presented in Example 2 support a conclusion that use of a higher dose upon subsequent administration (at which subjects should have low disease burden or be otherwise not at risk for toxicity) will not lead to an increased toxicity risk.

Example 5: Multiple Dose Regimen of CAR+ T Cells for Treating Acute Lymphoblastic Leukemia (ALL)

In an exemplary dose regimen, subjects with CD19+ B cell acute lymphoblastic leukemia (ALL) were treated with two doses of CAR-expressing T cells, which included administering a first low dose of cells and a consecutive higher dose of cells. Before treatment, autologous CAR-expressing T cells were generated substantially as described in Example 2. Subjects received preconditioning chemotherapy including a single intravenous lymphodepleting dose of 1.0-3.0 g/m² cyclophosphamide at 2-5 days prior to the first dose of CAR-expressing T cells. The first dose included approximately $1 \times 10^6$ cells/kg patient weight. A consecutive dose of cells expressing the CAR (approximately $3 \times 10^6$ such cells/kg patient weight) was administered 14-28 days after the first dose at a dose.

Subjects were monitored for efficacy of treatment, including by bone marrow, peripheral blood, and cerebrospinal fluid (CSF) examination, evaluation of central nervous system (CNS) symptoms, in order to assess and monitor disease burden (including levels and presence or absence of morphologic and degree of molecularly-detectable disease), evidence of adverse events, including CRS and neurotoxicity, and survival.

Example 6: Repeated Dosing Schedule of CAR+ T Cells for Treating Acute Lymphoblastic Leukemia (ALL)

In an exemplary dose regimen, subjects with relapsed or refractory B cell acute lymphoblastic leukemia (ALL) are treated with repeated doses of CAR-expressing T cells, which includes administering at least three doses of cells within the first 28 days. Before treatment, autologous CAR-expressing T cells are generated substantially as described in Example 2. Optionally, subjects receive preconditioning immunosuppressive chemotherapy of cyclophosphamide and/or fludarabine (CY/FLU), which is administered at least two days before the first dose of CAR-expressing cells and generally no more than 5 or no more than 7 days before administration of cells.

Subjects receive a first dose of CAR-expressing cells that is less than or equal to about $1 \times 10^6$ cells/kg patient weight, such as ranging from about $0.4 \times 10^6$ cells/kg to about $1 \times 10^6$ cells/kg, inclusive. Within 14-28 days after administration of the first dose, and/or prior to development of an immune response to the CAR, subjects are infused with two additional higher doses of cells. In some embodiments, a consecutive dose of CAR-expressing cells is administered about 14 days after the first dose at a dose that is higher than the first dose, such as a dose ranging from about $2.5 \times 10^6$ cells/kg to about $4.5 \times 10^6$ cells/kg, such as approximately $3 \times 10^6$ cells/kg patient weight, followed by a third dose of CAR-expressing cells that is administered about 28 days after the first dose at a dose that is higher than the first dose, such as a dose ranging from about $2.5 \times 10^6$ cells/kg to about $4.5 \times 10^6$ cells/kg, such as approximately $3 \times 10^6$ cells/kg patient weight. In some embodiments, one or more subsequent doses of cells are administered. In some embodiments, a fourth dose of CAR-expressing cells is administered within about 42 to 56 days after the first dose at a dose that is higher than the first dose, such as a dose ranging from about $2.5 \times 10^6$ cells/kg to about $4.5 \times 10^6$ cells/kg, such as approximately $3 \times 10^6$ cells/kg patient weight.

Subjects are monitored for efficacy of treatment by measuring the overall remission rate (ORR) after the final dose of cells in subjects. In some embodiments, efficacy is monitored in subjects with morphologic evidence of disease prior to treatment (greater than or equal to 5% of cells in bone marrow were blasts). ORR is determined as the proportion of subjects with CR with incomplete blood count recovery (CRi), as determined by examination of the bone marrow, peripheral blood, and cerebrospinal fluid (CSF), as well as physical examination and evaluation of central nervous system (CNS) symptoms.

Example 7: Multiple Dose Regimen of CAR+ T Cells with Lymphodepleting Chemotherapy Pre-Conditioning for Treating Non-Hodgkin Lymphoma (NHL)

In exemplary dose regimens for treating CD19+ B cell Non-Hodgkin Lymphoma (NHL), a multiple dose regimen of CAR-expressing T cells is used to treat subjects. Before treatment, autologous CAR-expressing T cells are generated substantially as described in Example 2. Subjects with NHL are treated with at least two doses of CAR-expressing T cells. Subjects receive a first dose of CAR-expressing cells that is less than or equal to about $1 \times 10^6$ cells/kg patient weight, such as ranging from about $0.4 \times 10^6$ cells/kg to about $1 \times 10^6$ cells/kg, inclusive. In exemplary dosage regimes, a consecutive dose of CAR-expressing T cells is administered 14 to 28 days after the first dose.

In one exemplary dosage regime, subjects with NHL receive a consecutive dose of CAR-expressing at a dose that is the same or lower than the first dose of CAR-expressing T cells, such as a dose that is less than or equal to about $1 \times 10^6$ cells/kg patient weight, such as ranging from about $0.4 \times 10^6$ cells/kg to about $1 \times 10^6$ cells/kg, inclusive. Optionally, further repeat doses are administered 14 to 28 days after a prior administration at a dose that is less than or equal to the dose administered in the prior administration.

In one exemplary dosage regime, prior to receiving a consecutive dose, subjects are optionally monitored for tumor burden. If molecular remission is detected, as evidenced by tumor reduction from morphological disease to MRD, subjects are administered a consecutive dose of CAR-expressing T cells at a dose that is higher than the first dose, such as a dose ranging from about $2.5 \times 10^6$ cells/kg to about $4.5 \times 10^6$ cells/kg, such as approximately $3 \times 10^6$ cells/kg patient weight. If molecular remission has not occurred, subjects are administered a consecutive dose of CAR-expressing T cells at a dose that is the same or lower than the first dose of CAR-expressing T cells, such as a dose that is less than or equal to about $1 \times 10^6$ cells/kg patient weight, such as ranging from about $0.4 \times 10^6$ cells/kg to about $1 \times 10^6$ cells/kg, inclusive. Optionally, further repeat doses are administered 14 to 28 days after a prior administration, with higher doses being administered if molecular remission has occurred and lower doses being administered if molecular remission has not occurred.

In one exemplary dosage regime, prior to receiving the first dose, subjects receive an immunodepleting preconditioning chemotherapy of cyclophosphamide and fludarabine (CY/FLU), which is administered at least two days before the first dose of CAR-expressing cells and generally no more than 7 days before administration of cells. After preconditioning treatment, subjects are administered the first dose as described above at a dose of CAR-expressing T cells that is less than or equal to about $1 \times 10^6$ cells/kg patient weight, such as ranging from about $0.4 \times 10^6$ cells/kg to about $1 \times 10^6$ cells/kg, inclusive. Subjects are administered a consecutive dose of CAR-expressing T cells at a dose that is higher than the first dose, such as a dose ranging from about $2.5 \times 10^6$ cells/kg to about $4.5 \times 10^6$ cells/kg, such as approximately $3 \times 10^6$ cells/kg patient weight. Optionally, further repeat doses are administered 14 to 28 days after a prior administration at a dose ranging from about $2.5 \times 10^6$ cells/kg to about $4.5 \times 10^6$ cells/kg, such as approximately $3 \times 10^6$ cells/kg patient weight.

Example 8: Assessment of PD1/PD-L1 Expression in T-Cells Stimulated Through a Chimeric Antigen Receptor (CAR)

T cells were isolated by immunoaffinity-based enrichment from leukapheresis samples from human subjects, and cells were activated and transduced with a viral vector encoding an anti-CD19 chimeric antigen receptor (CAR) containing a human CD28-derived intracellular signaling domain and a human CD3 zeta-derived signaling domain. Surface expression on the resulting isolated compositions (of the CAR and of certain T cell markers) was assessed by flow cytometry, to determine, in the composition, the percentage of CAR+ cells among all T cells in the and among T cell subsets, as well as ratio of CD4+ to CD8+ T cells (see Table 5).

TABLE 5

Anti-CD19 CAR Expression on Transduced T cells

|  | CD3+CAR+ | CD4+CAR+ | CD8+CAR+ | CD3+CD4+ | CD3+CD8+ |
|---|---|---|---|---|---|
| percent (average) | 49.91 | 23.60 | 28.73 | 40.03 | 53.66 |
| Standard Deviation | 2.97 | 1.18 | 2.38 | 1.10 | 1.22 |

The composition then was subdivided into different samples by incubation with: 1) K562 cells expressing the antigen for which the CAR was specific (K562-tCD19 cells) (antigen-specific coculture); 2) K562 cells expressing an unrelated antigen (K562-ROR1 cells) (non-specific coculture control); or 3) plate-bound anti-CD3 antibody and soluble anti-CD28 antibody (for stimulation via the TCR complex), initially using plate-bound anti-CD3 and soluble anti-CD28, and at day 3, where applicable, incubation. For (1) and (2), K562 (immortalized myelogenous leukemia line) cells, were engineered to express CD19 and ROR1, respectively, and incubated with the CAR-expressing T cells at a 1:1 ratio. For each of the conditions, CAR-expressing T cells were stimulated for 24 hours. An unstimulated sample ("media," no K562 cells or stimulating antibodies) was used as an additional negative control.

After 24 hours in culture, flow cytometry was performed to assess surface expression of PD1, PD-L1, PD-L2, T cell markers, and CAR (based on goat-anti-mouse ("GAM") staining to detect the murine variable region portion of the CAR) on the cells in each sample. Live, single cells with forward scatter and side scatter profiles matching lymphocytes were gated for analysis. Expression of PD1, PD-L1 and PD-L2 was assessed on various gated populations of T cells (CD4$^+$/CAR$^+$, CD4$^+$/CAR$^-$, CD8$^+$/CAR$^+$, and CD8$^+$/CAR$^-$), with gates set based on the surface expression of various markers, and using values for the negative control ("media") sample to determine appropriate gating.

Figure 3A:
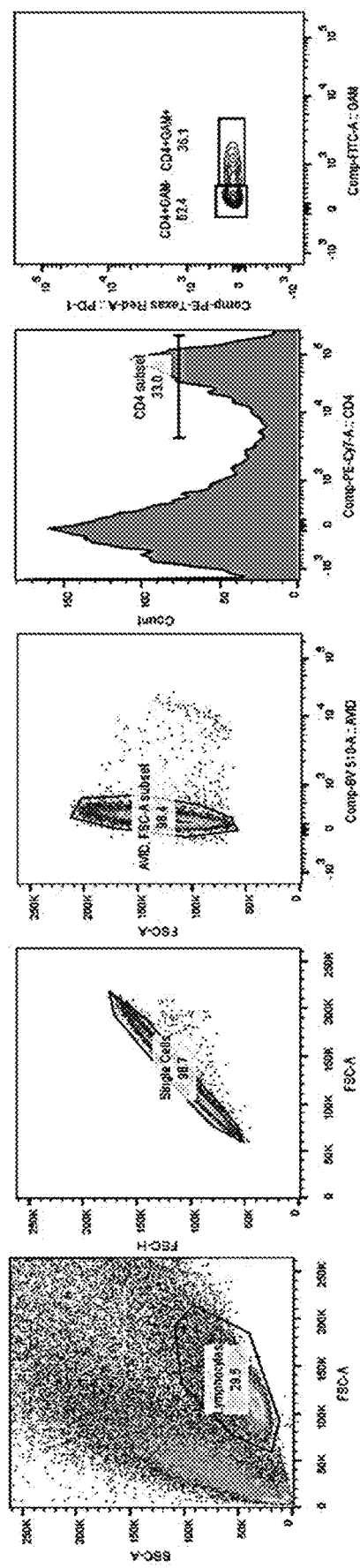
FIG. 3A depicts surface expression, as detected by flow cytometry, of PD-1, PD-L1, and PD-L2 on a population of T cells gated for positive surface expression of CD4 and an anti-CD19 chimeric antigen receptor (CAR) (gating strategy shown in top panel), following incubation for 24 hours under various conditions (media, K562-tCD19, K562-tROR1, aCD3/aCD28), as described in Example 8.
Figure 3A:
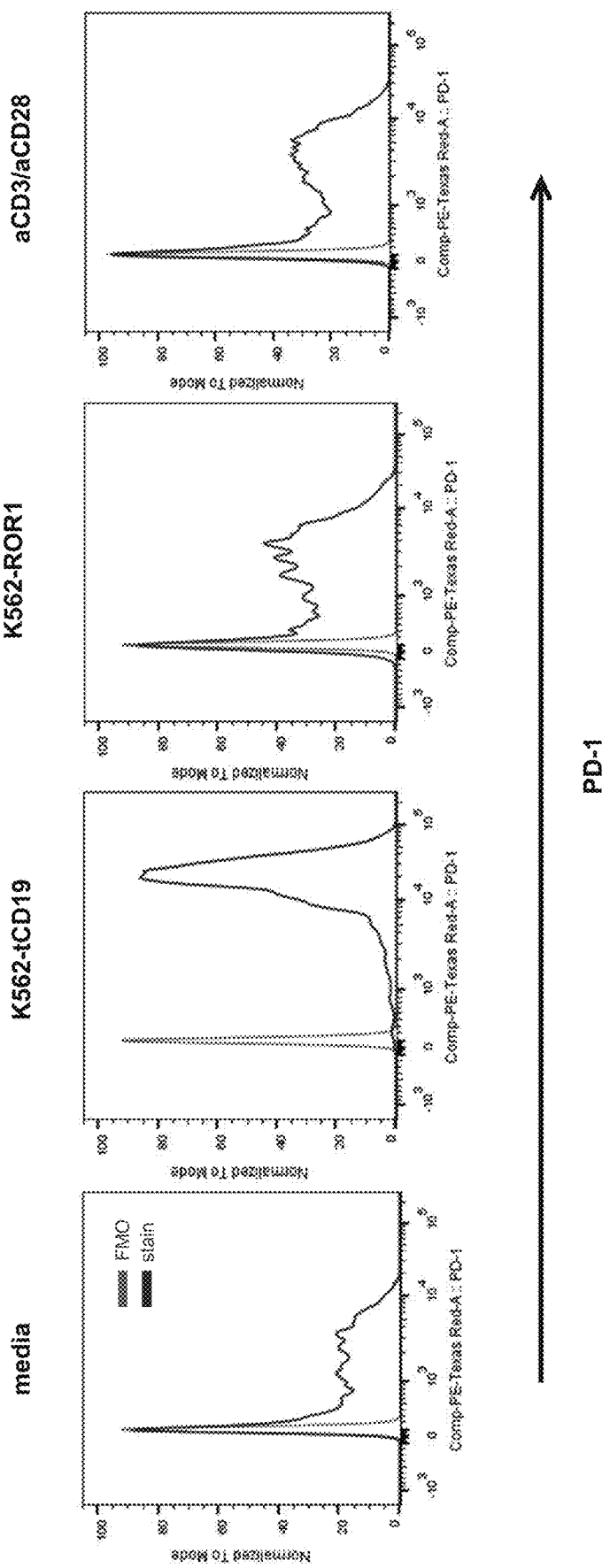
Figure 3A:
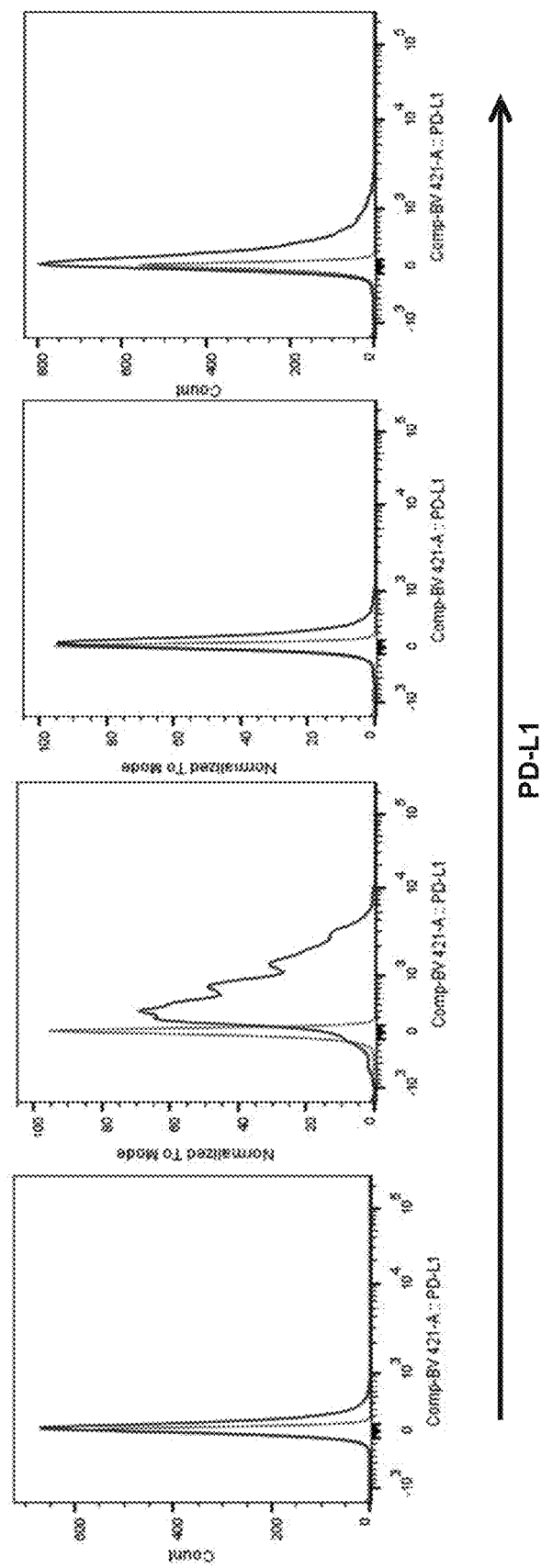
Figure 3A:
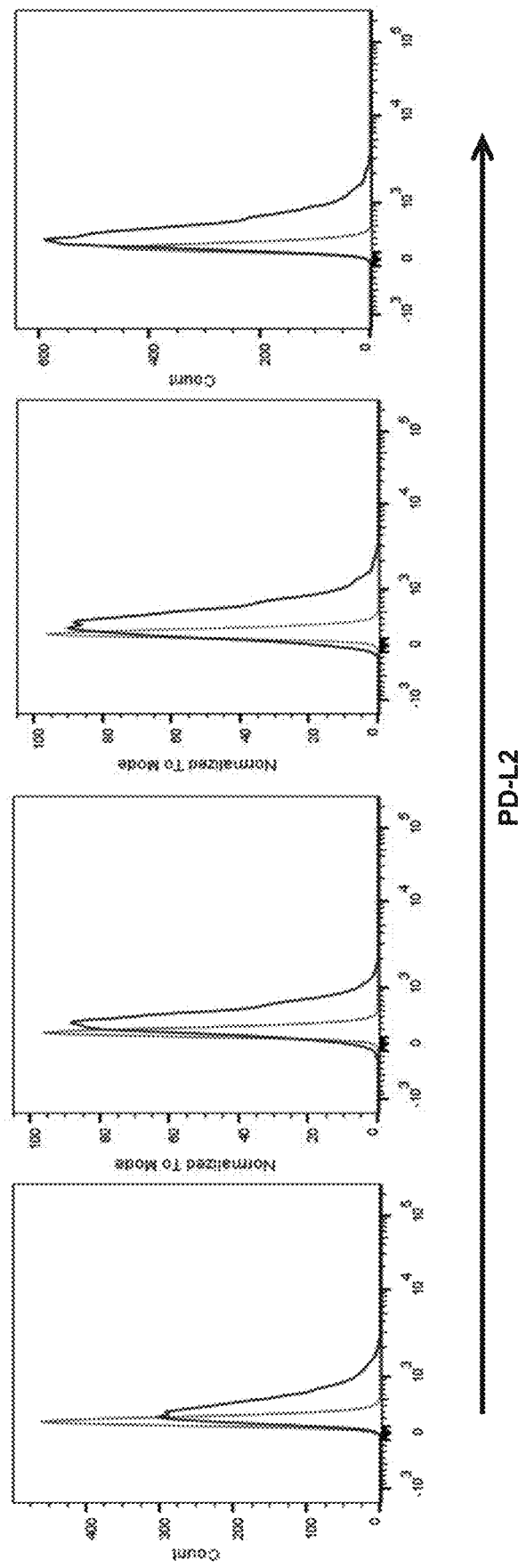
Figure 4A:
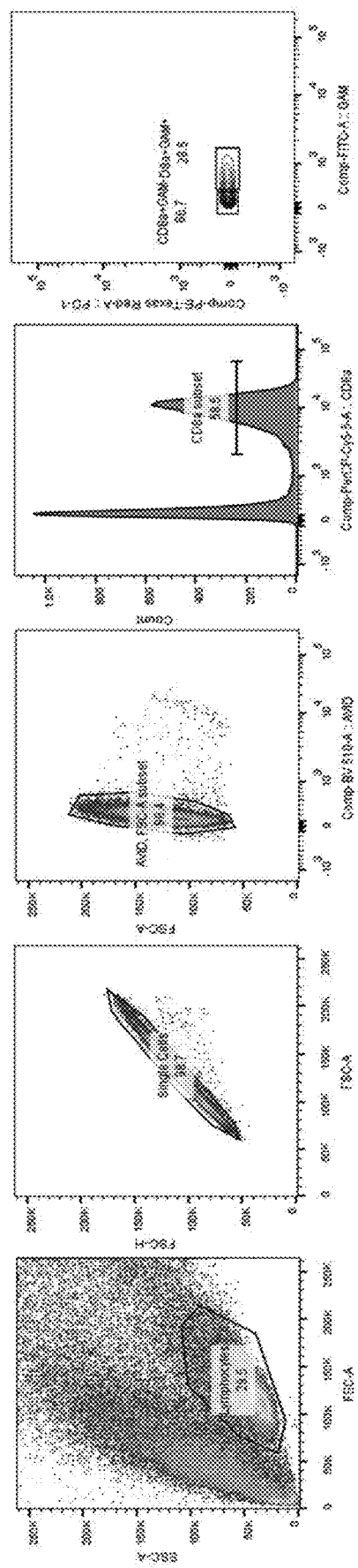
FIG. 4A depicts surface expression, as detected by flow cytometry, of PD-1, PD-L1, and PD-L2 on a population of T cells gated for positive surface expression of CD8 and an anti-CD19 chimeric antigen receptor (CAR) (gating strategy shown in top panel), following incubation for 24 hours under various conditions (media, K562-tCD19, K562-tROR1, aCD3/aCD28), as described in Example 8.
Figure 4A:
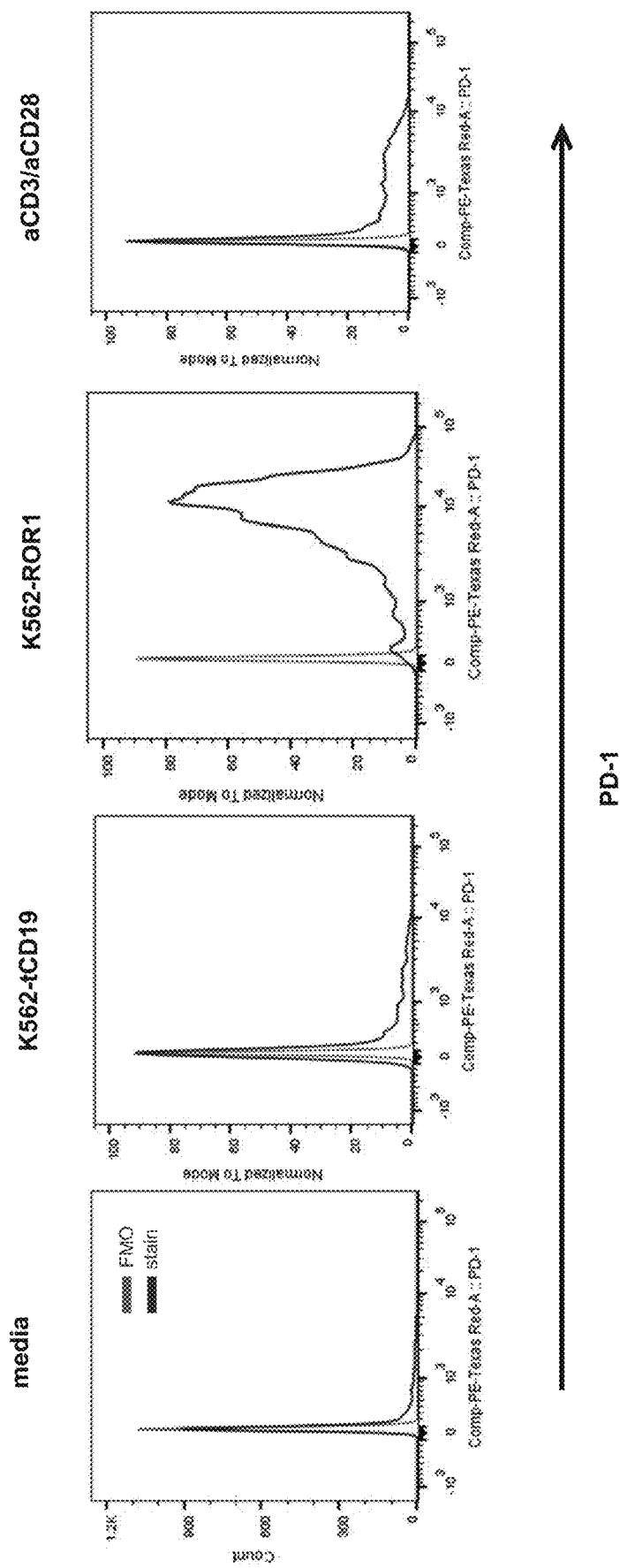
Figure 4A:
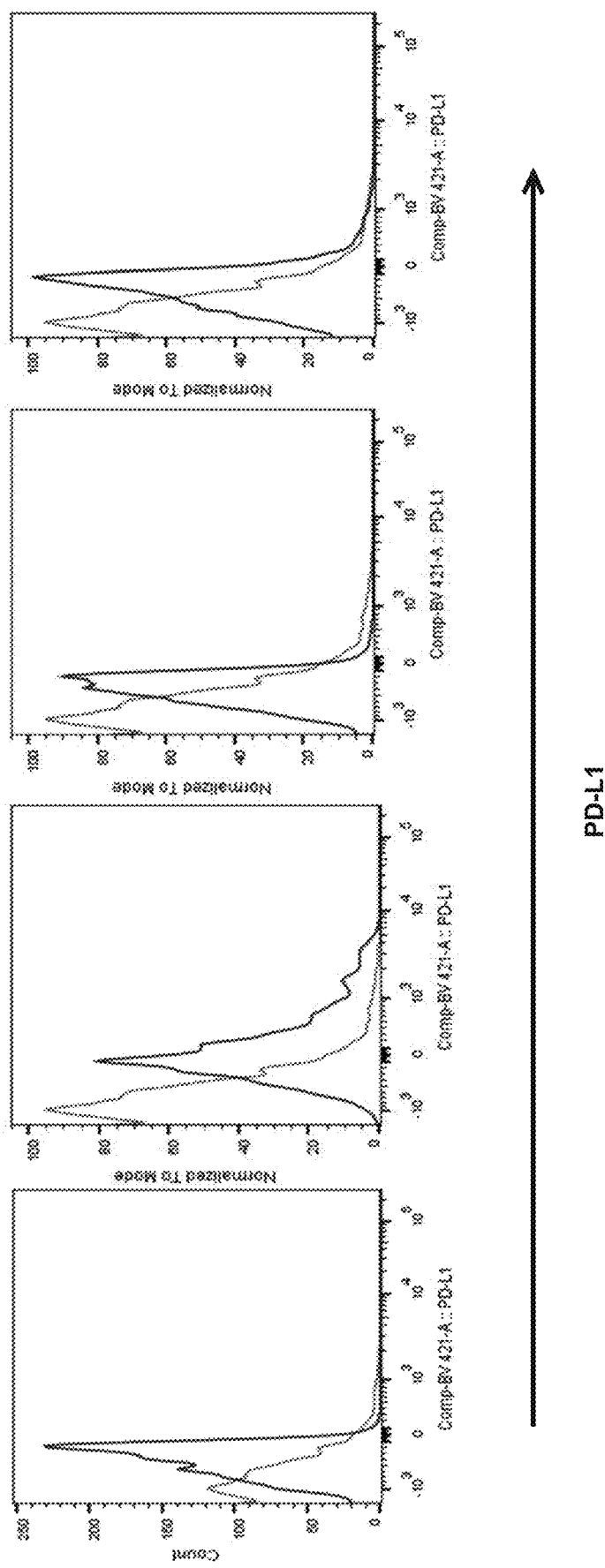
Figure 4A:
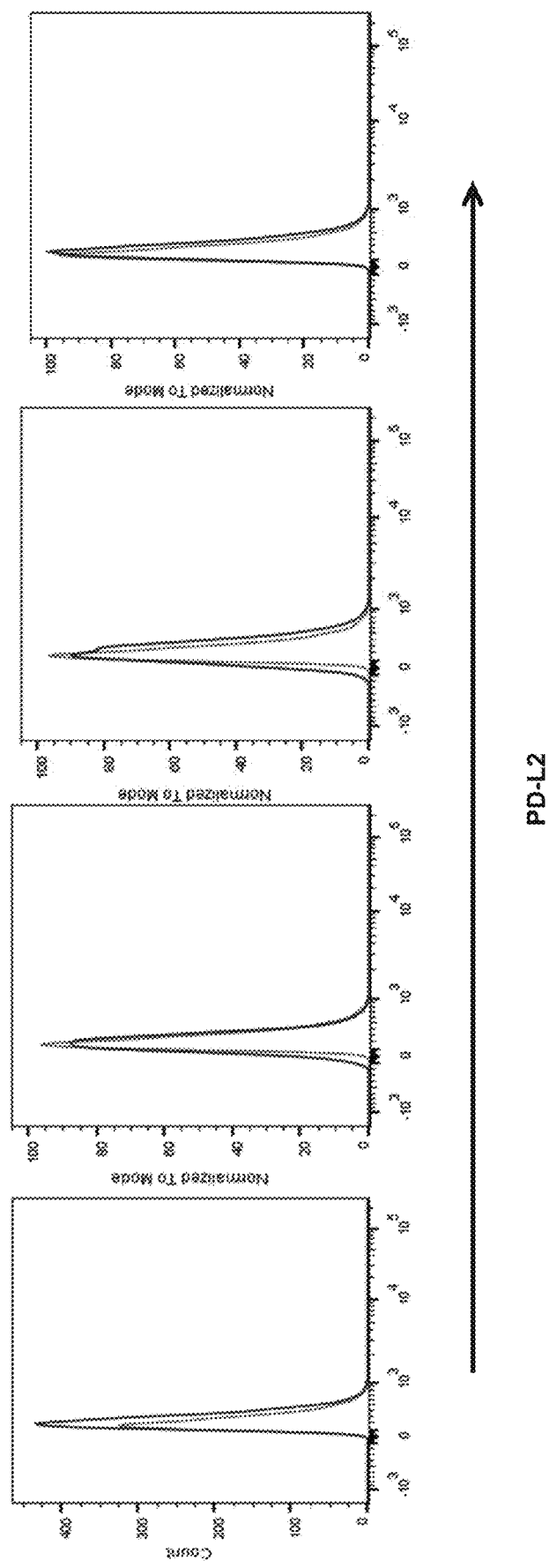

As shown in FIGS. 3A and 4A, PD1 and PD-L1 expression increased within twenty-four (24) hours in both CD4$^+$/CAR$^+$ and CD8$^+$/CAR$^+$ T cells when cultured with cells expressing the antigen to which the CAR was specific (K562-tCD19). This increase in expression of PD1 and PD-L1 was not observed within this timeframe in CAR+ cells incubated with cells of the same type expressing an irrelevant antigen cells (K562-ROR1) or in any of the CD4$^+$ or CD8$^+$ cell populations incubated under conditions designed to effect stimulation through the TCR complex (anti-CD3 and anti-CD28 antibodies). Expression of PD-L2 was not upregulated within this timeframe under any of the stimulated conditions tested.

Figure 3B:
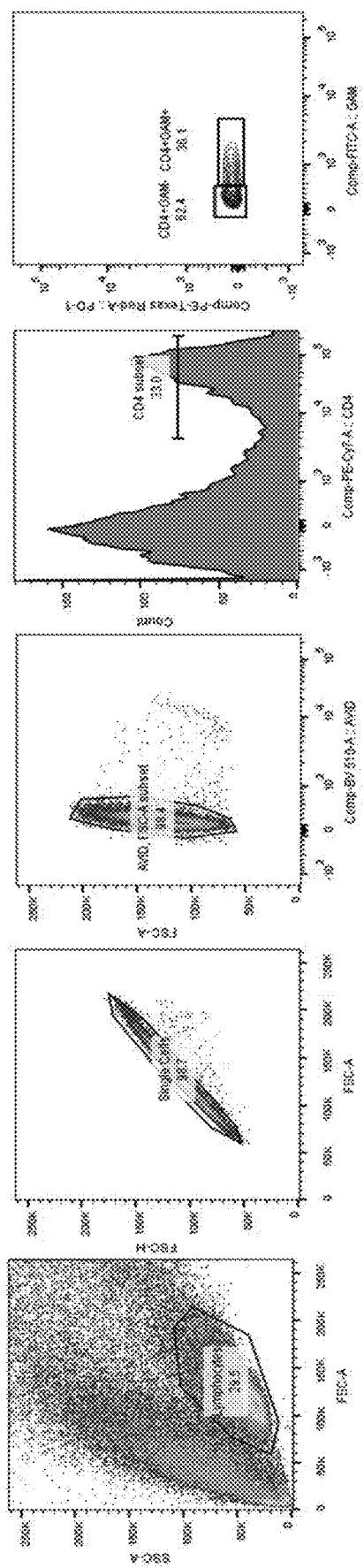
FIG. 3B depicts surface expression, as detected by flow cytometry, of PD-1, PD-L1, and PD-L2 on a population of T cells gated for positive surface expression of CD4 and negative surface expression of an anti-CD19 chimeric antigen receptor (CAR) (gating strategy shown in top panel), following incubation for 24 hours under various conditions (media, K562-tCD19, K562-tROR1, aCD3/aCD28), as described in Example 8.
Figure 3B:
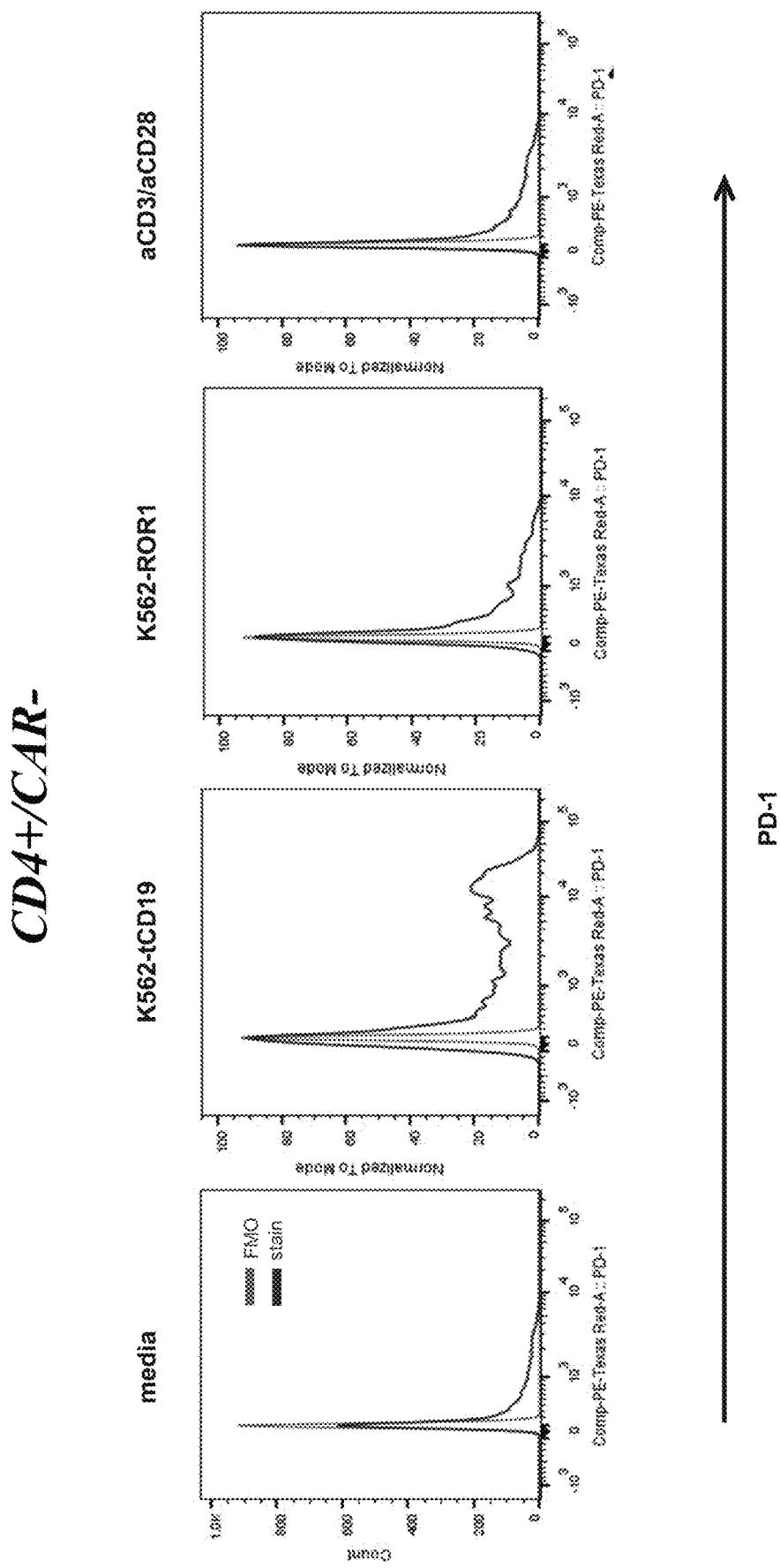
Figure 3B:
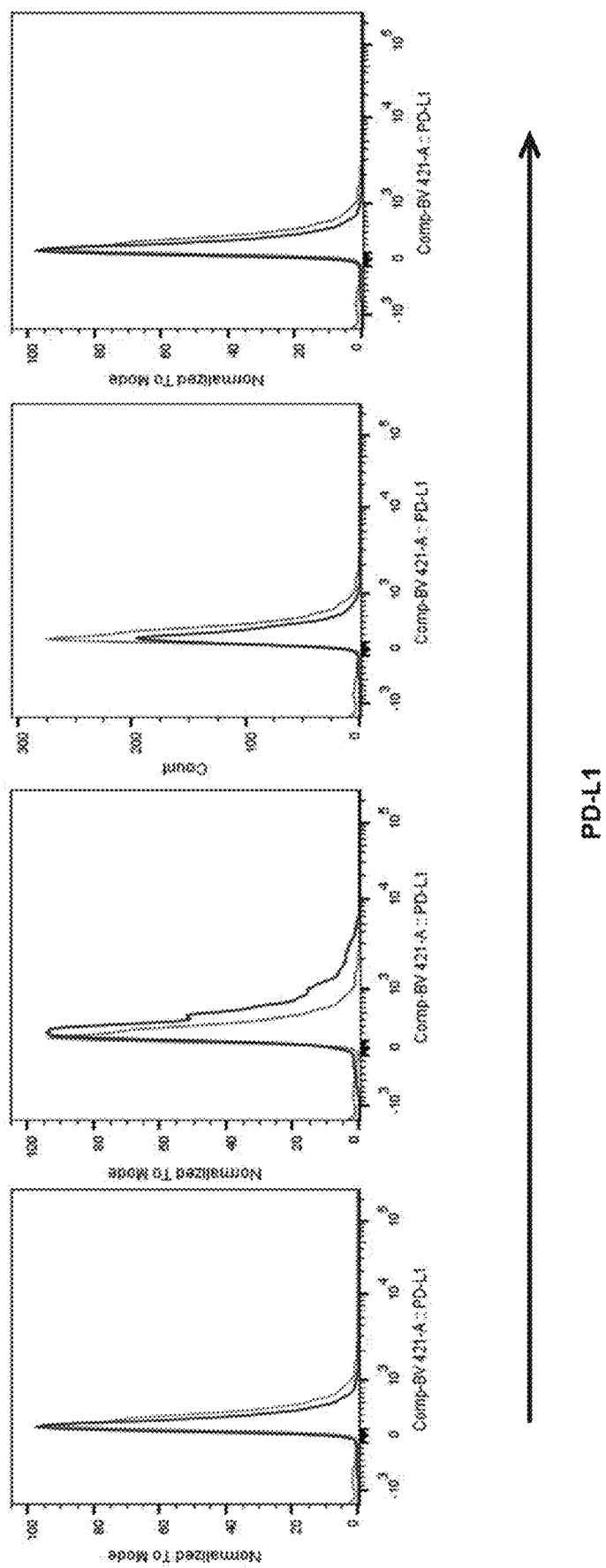
Figure 3B:
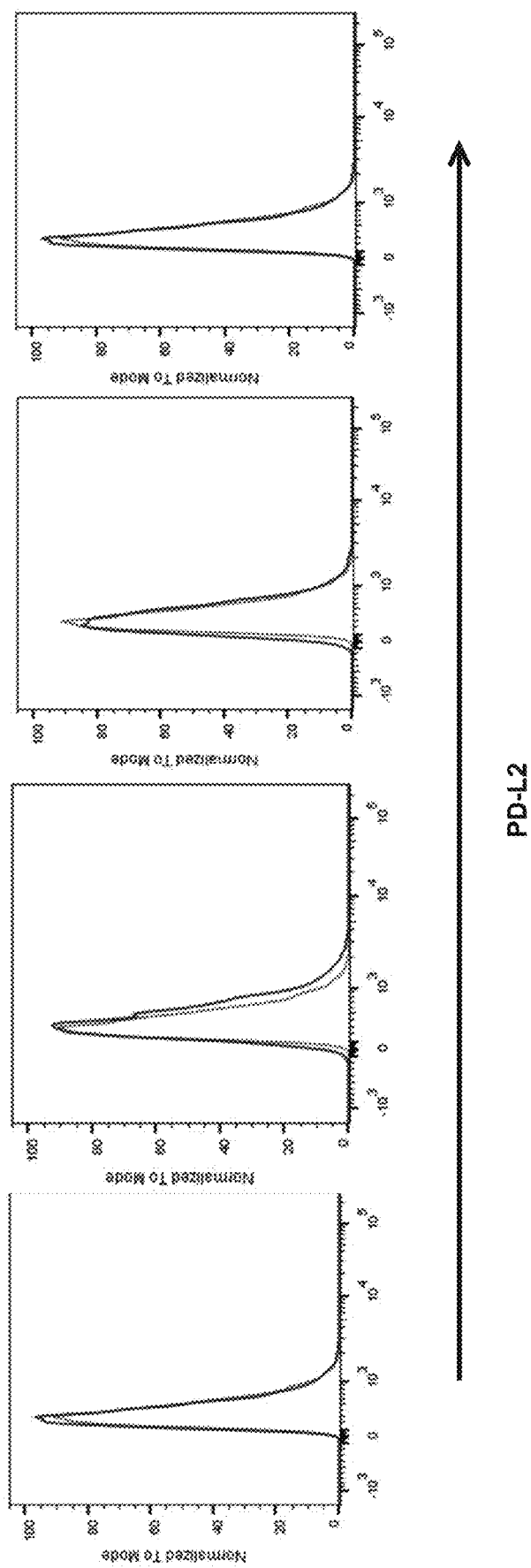
Figure 4B:
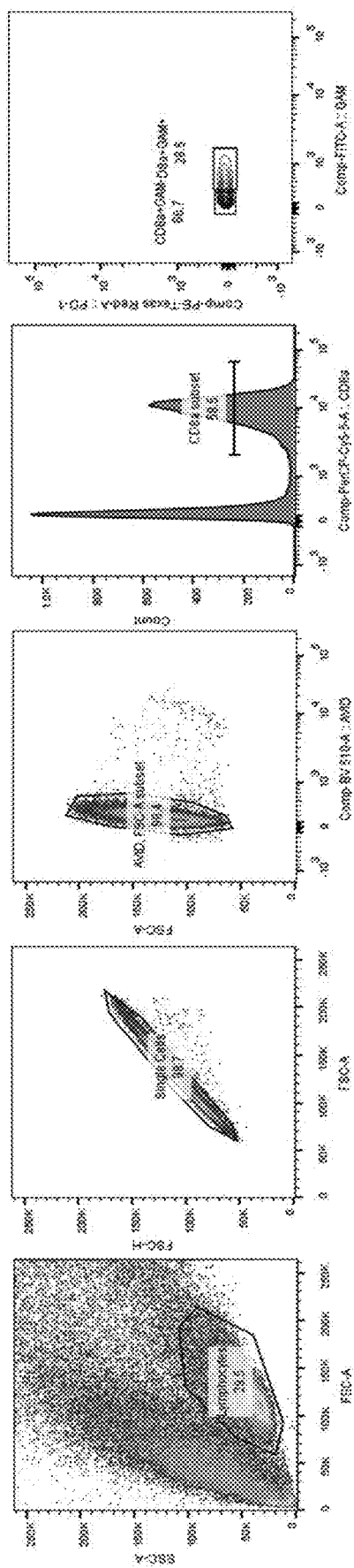
FIG. 4B depicts surface expression, as detected by flow cytometry, of PD-1, PD-L1, and PD-L2 on a population of T cells gated for positive surface expression of CD8 and negative surface expression for an anti-CD19 chimeric antigen receptor (CAR) (gating strategy shown in top panel), following incubation for 24 hours under various conditions (media, K562-tCD19, K562-tROR1, aCD3/aCD28), as described in Example 8.
Figure 4B:
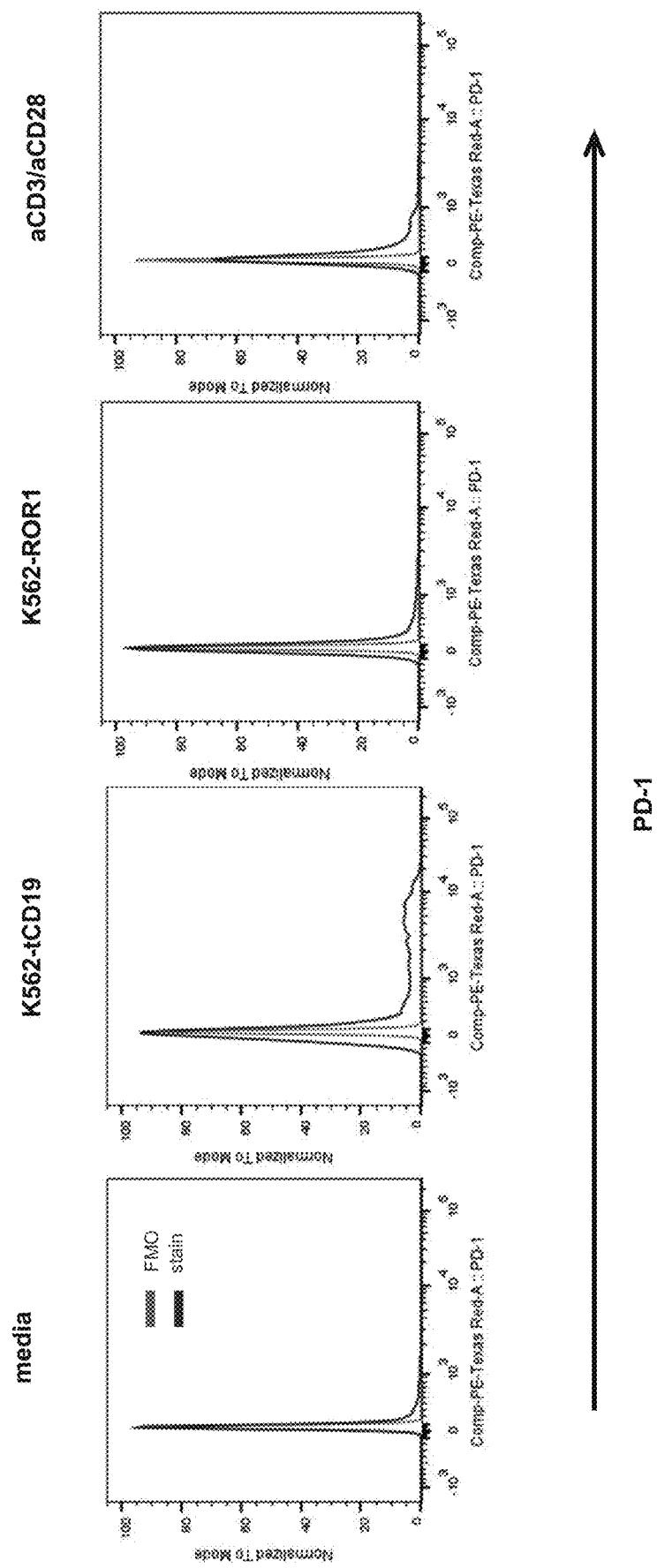
Figure 4B:
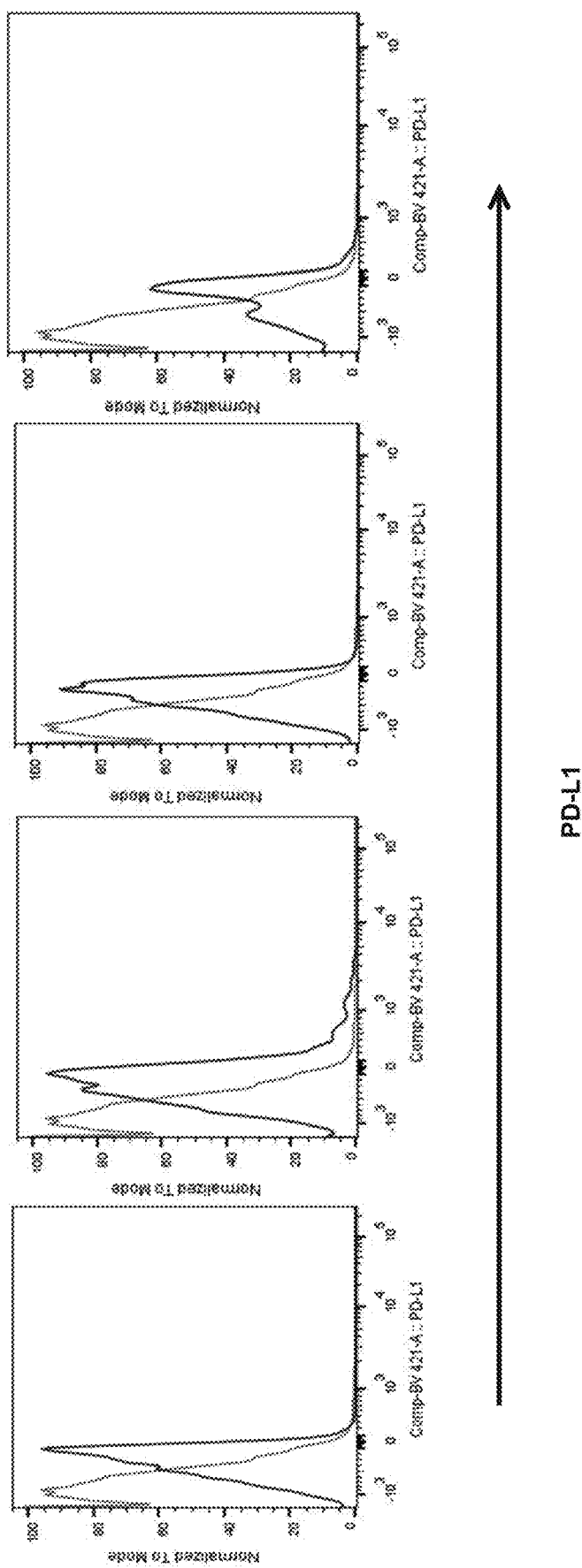
Figure 4B:
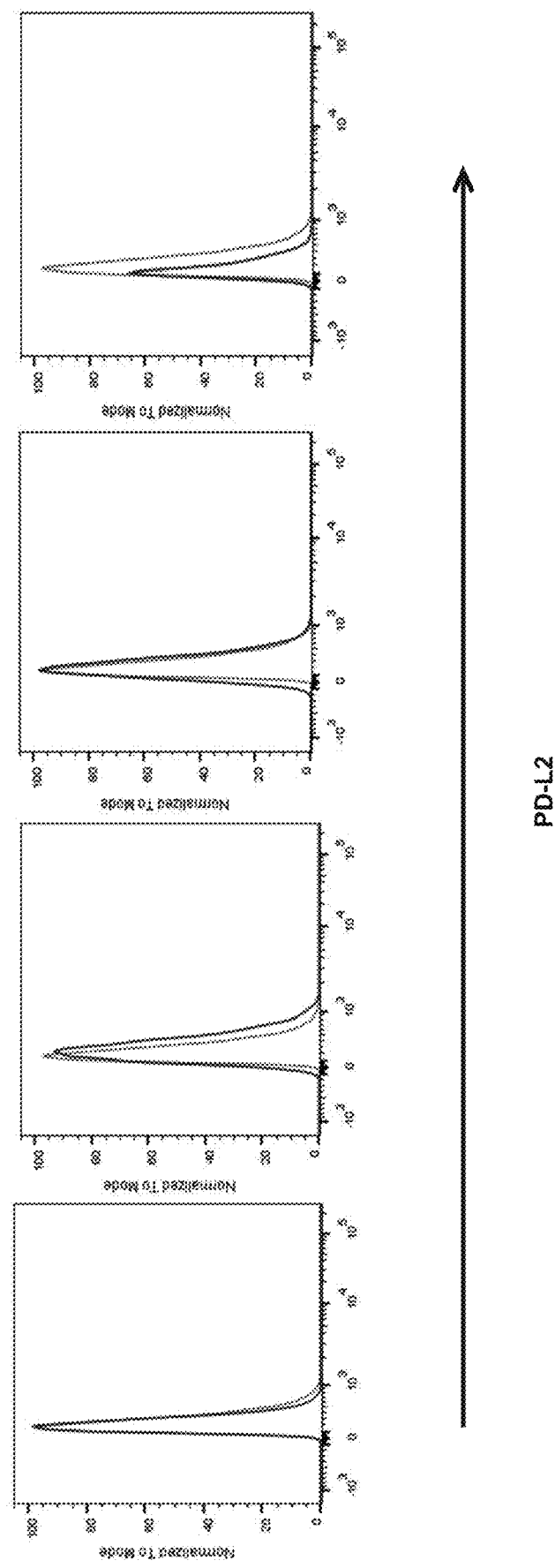

As shown in FIGS. 3B and 4B, the increase in expression of PD-1 and PD-L1 in cells incubated with CD19-expressing cells was observed to be primarily due to expression of the anti-CD19 CAR. Neither the CD4+-gated nor the CD8+-gated T cells that did not express the CAR ("CAR-") exhibited substantial increases in PD-1 or PD-L1 surface expression following incubation with the CD19-expressing cells.

Similar results were obtained in the presence of T cells genetically engineered with an anti-CD19 chimeric antigen receptor (CAR) containing a human 4-1BB-derived intracellular signaling domain and a human CD3 zeta-derived signaling domain. Thus, the results showed that the upregulation of PD-1 and PD-L1 occurred on T cells transduced with CAR constructs containing either a CD28 or 4-1BB costimulatory signaling domain. These data demonstrate upregulation of surface expression of PD1 and PD-L1 within twenty-four hours following stimulation through the chimeric antigen receptor, but not following stimulation under conditions designed to mimic signal through the canonical T cell antigen receptor complex (CD3/CD28 antibodies).

These data further support a conclusion that exposure, in vivo, upon administration to subjects, to antigen to which the CAR was specific may in some contexts result in upregulation of PD-L1 and/or PD-1, which may occur to a greater degree and/or more rapidly than (or in distinction from) what would occur following interaction with cognate antigen through an endogenous TCR.

Upregulation of such molecules and other inhibitory markers may contribute to loss of function and/or exhaustion of the T cells and for example may impair long-term exposure to the cells. A repeat or consecutive dose(s) of cells may be used to deliver cells not yet expressing the inhibitory molecules, such as PD-1 and/or PD-L1, or expressing them at lower levels compared to the cells present in the subject. Thus, these data provide further support for a multiple dosing schedule, in which a consecutive dose of T cells is administered to a subject following an initial dose, such as at a time at which PD-L1 or PD-1 has been or is upregulated on cells of the initial dose, following exposure to the target antigen.

In some embodiments, in the consecutive dose, the inhibitory molecule(s) are not expressed or substantially expressed (or expressed to the same degree as a reference cell population) on the cells therein (or on greater than 50, 40, 30, 20, 10, or 5% of the cells therein). In some embodiments, repeated doses of cells that do not express or do not substantially express inhibitory molecules, such as PD-1 and PD-L1, can extend the time during which functional CAR-expressing T cells or CAR-expressing T cells having robust function are present in the subject. In some embodiments, replenishing the army of genetically engineered T cells by administering one or more consecutive doses can lead to a greater and/or longer degree of exposure to the antigen receptor (e.g. CAR)-expressing cells and improve treatment outcomes. In some embodiments, the consecutive dose is administered at a time at which PD-L1 or PD-1 is upregulated compared to a reference level or population, such as compared to the cells in the composition of the first dose immediately prior to administration to the subject, for example, to a degree that is at least 10, 20, 30, 40, 50, 60, 70, or 80% higher surface expression as compared to the reference population.

Example 9: Assessment of Neurotoxicity in Subjects Based on Tumor Burden

Subjects with CD19$^+$ B cell acute lymphoblastic leukemia (ALL) were administered autologous T cells expressing an anti-CD19 chimeric antigen receptor (CAR). Before treatment, autologous CAR-expressing T cells were generated substantially as described in Example 2

Figure 5A:
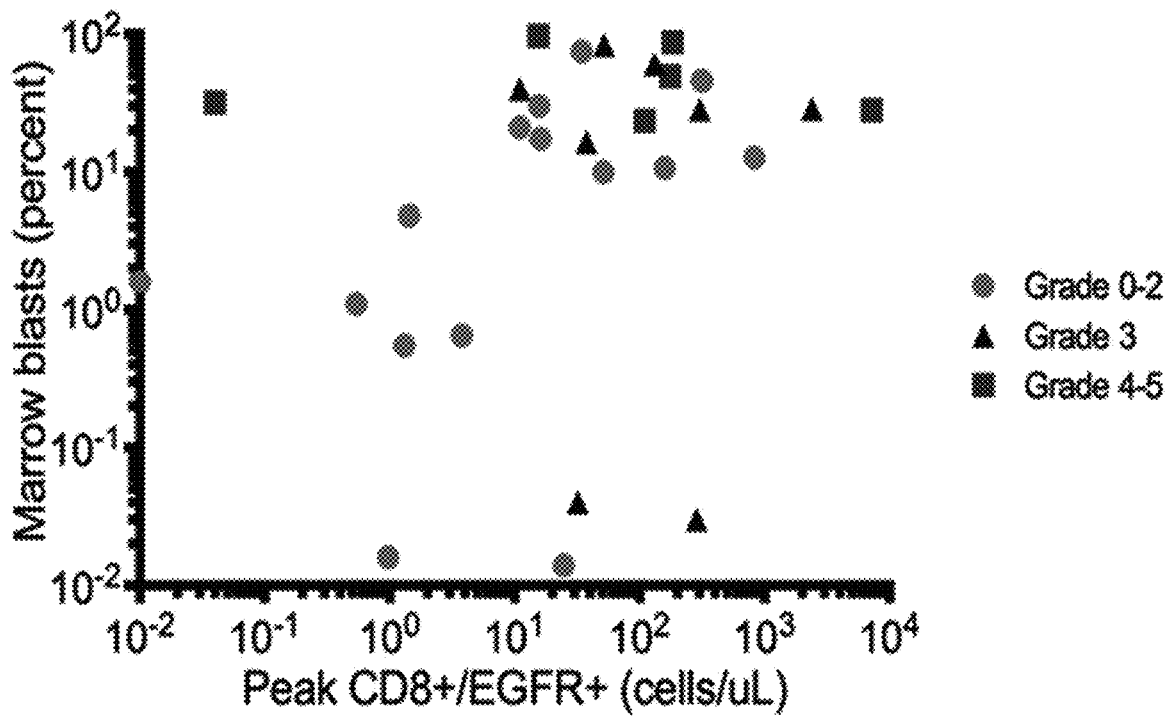
FIG. 5A shows the degree of neurotoxicity (Grade 0-2, Grade 3, Grade 4-5) observed in subjects treated with a single infusion of CAR-expressing T cells. Data are plotted as tumor burden (percent marrow blasts) vs. number of CAR-expressing T cells (CD8$^+$/EGFR$^+$, top panel; or CD4$^+$/EGFR$^+$, bottom panel) per µL of peripheral blood.
Figure 5A:
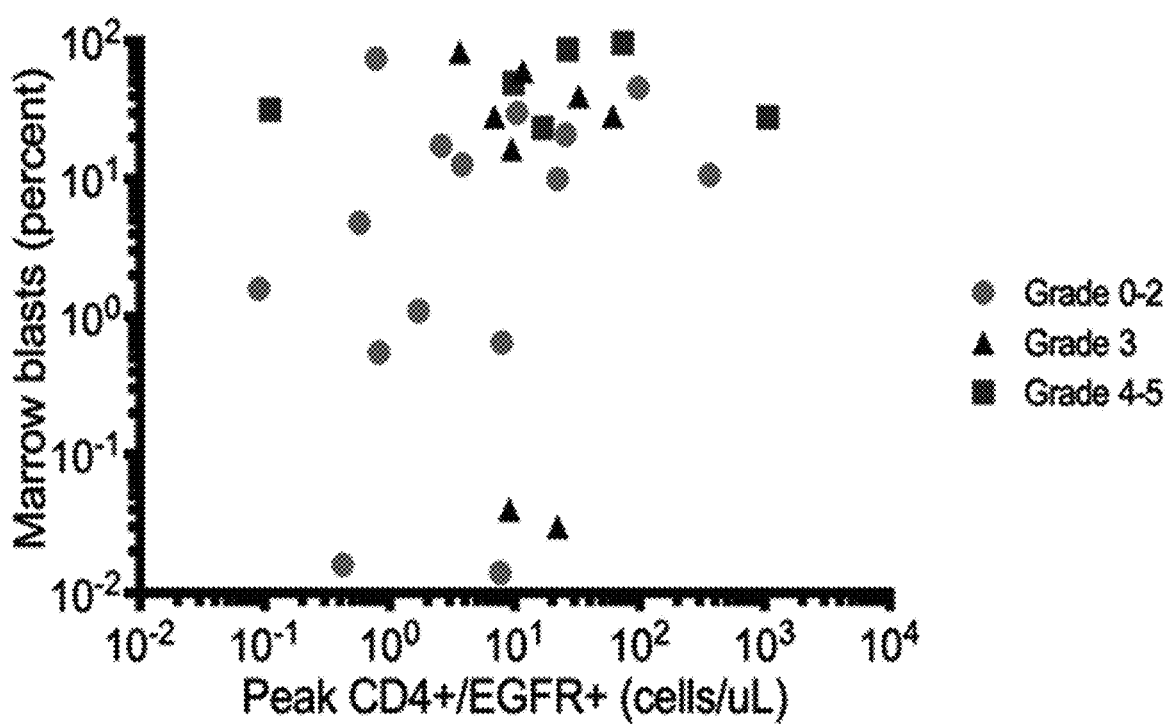
Figure 5B:
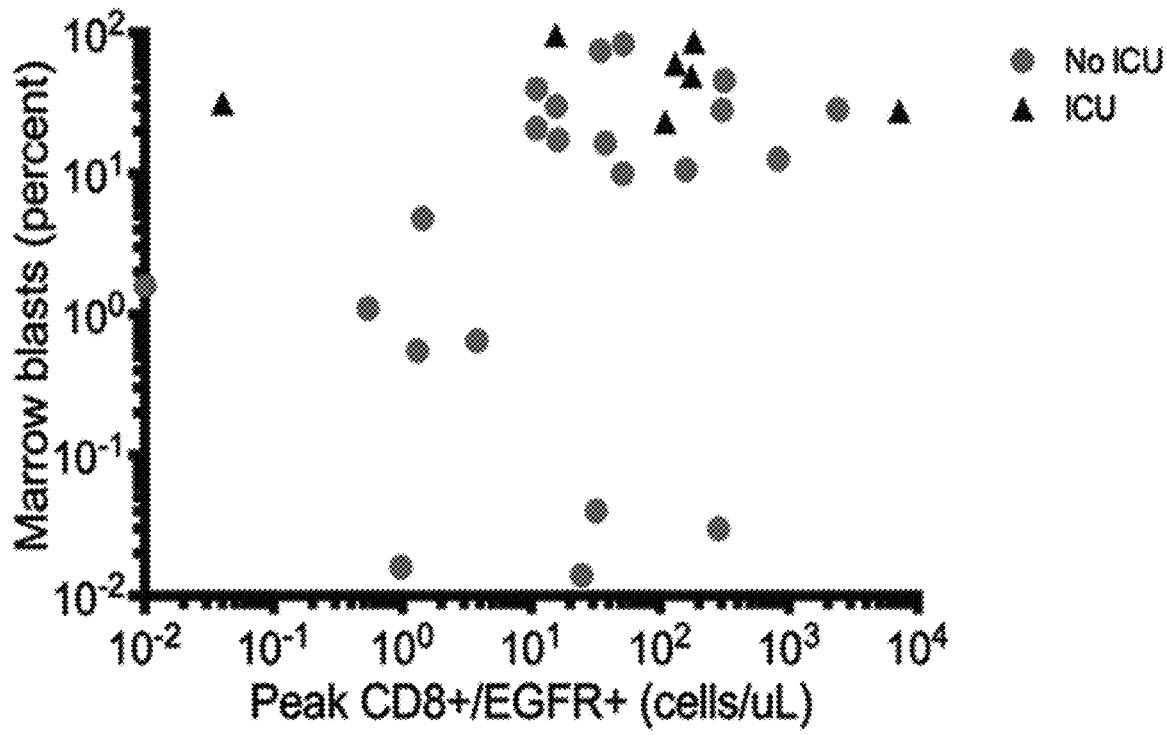
FIG. 5B shows the requirement for care in the intensive care unit (ICU) in subjects treated with a single infusion of CAR-expressing T cells. Data are plotted as tumor burden (percent marrow blasts) vs. number of CD8$^+$/EGFR$^+$ (top panel) or CD4$^+$/EGFR$^+$ (bottom panel) cells per µL of peripheral blood.
Figure 5B:
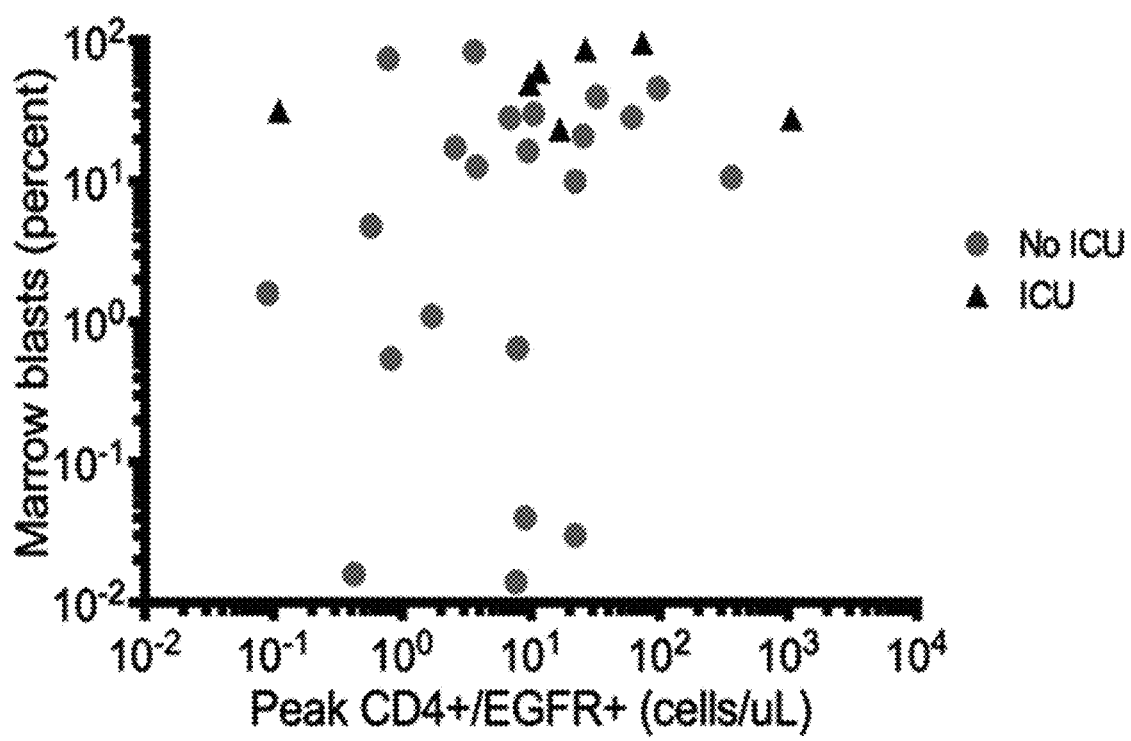

Neurotoxicity was observed in a cohort of patients after receiving a single IV continuous infusion of CAR-expressing T cells, at a dose of either $2\times10^5$ cells/kg (N=13), $2\times10^6$ cells/kg (N=15) or $2\times10^7$ cells/kg (N=2) (see FIGS. 5A and 5B). In some cases, a preconditioning chemotherapeutic treatment of cyclophosphamide (about 2 g/m$^2$), cyclophosphamide (2 g/m$^2$) and etoposide (100 mg/m$^2$, administered three times daily) or cyclophosphamide (60 mg/kg) and fludarabine (25 mg/m$^2$, administered three to five times daily) was administered to subjects prior to infusion.

The number of CAR-T cells present in peripheral blood of treated subjects was determined post-treatment by performing flow cytometry for surface expression of EGFRt (CAR-specific marker) and CD4 or CD8. Neurotoxicity also was determined and monitored, and graded based on severity as described above.

As shown in FIG. 5A, the degree of neurotoxicity observed in this study in treated subjects correlated to the presence of relatively higher tumor burden prior to treatment. As shown in FIG. 5A, subjects exhibiting severe symptoms of neurotoxicity with a grade of 3 or higher also exhibited a greater number of CD8+ or CD4+ CAR-T cells in peripheral blood following treatment at the time assessed, indicating a correlation between tumor burden, the degree of expansion of CAR+ T cells and neurotoxicity. FIG. 5B shows that subjects determined to require intensive care unit (ICU) care following treatment were among those having relatively higher percentages of bone marrow blasts prior to treatment.

Example 10: Risk-Adapted Dosing of CAR+ T Cells

Five subjects, among those treated as described in Example 9, were administered the anti-CD19 CAR-T cells in doses adapted based on tumor burden.

Prior to treatment, tumor burden was assessed by evaluating the percent of marrow blasts present in the bone marrow. Subjects having greater than 20% blasts (>20%) in bone marrow were selected for administration of a dose of CAR-T cells ($2\times10^5$ T cells/kg) that was relatively lower as compared to the dose administered to subjects having less than or equal to 20% blasts. Subjects having less than or equal to 20% blasts (<20%) were selected for administration of a relatively higher dose ($2\times10^6$ CAR-T cells/kg). CAR-expressing T cells were administered to subjects by single intravenous (IV) continuous infusion.

At days 0, 1, 3, 7, 10, 14, 21 and 28 post-treatment, the number of CAR-T cells present in peripheral blood of treated subjects was determined by performing flow cytometry of a cell sample for surface expression of EGFRt (CAR-specific marker) and CD4 or CD8. Subjects also were monitored for toxicity, including severe toxic outcomes requiring intensive care unit (ICU) care.

CAR-T cells were observed to expand in all subjects. As compared to a group of subjects receiving similar treatment, but for which the administered dosage was not based on tumor burden, the risk-adapted dosing resulted in a reduced incidence of serious toxicity. For example, in subjects for which the administered dosage was not based on tumor burden, seven of eleven subjects were required to have ICU care. In contrast, none (0%) of the five subjects for which risk-adapted dosing was used required ICU care.

Example 11: Pre-Conditioning with Fludarabine Prior to CAR-T Cell Administration in Subjects with B Cell Acute Lymphoblastic Leukemia (ALL)

Subjects with CD19+ B cell acute lymphoblastic leukemia (ALL) were administered $2\times10^6$ cells/kg of autologous T cells expressing an anti-CD19 chimeric antigen receptor (CAR). Before treatment, autologous CAR-expressing T cells were generated substantially as described in Example 2.

Prior to administration of the CAR-expressing T cells, subjects were treated either with 1) 2 g/m$^2$ cyclophosphamide (with or without administration of 100 mg/m$^2$ etoposide three times daily) (N-=5, no Flu treated group), or were treated with 60 mg/kg (~2 g/m$^2$) cyclophosphamide and 3 to 5 doses of 25 mg/m$^2$ fludarabine (N=10, designated Flu treated group).

At days 0, 1, 3, 7, 10, 14, 21 and 28 post-treatment, the number of CAR-T cells present in peripheral blood of treated subjects was determined by performing flow cytometry of a cell sample for surface expression of EGFRt (CAR-specific marker) and CD4 or CD8.

Figure 6A:
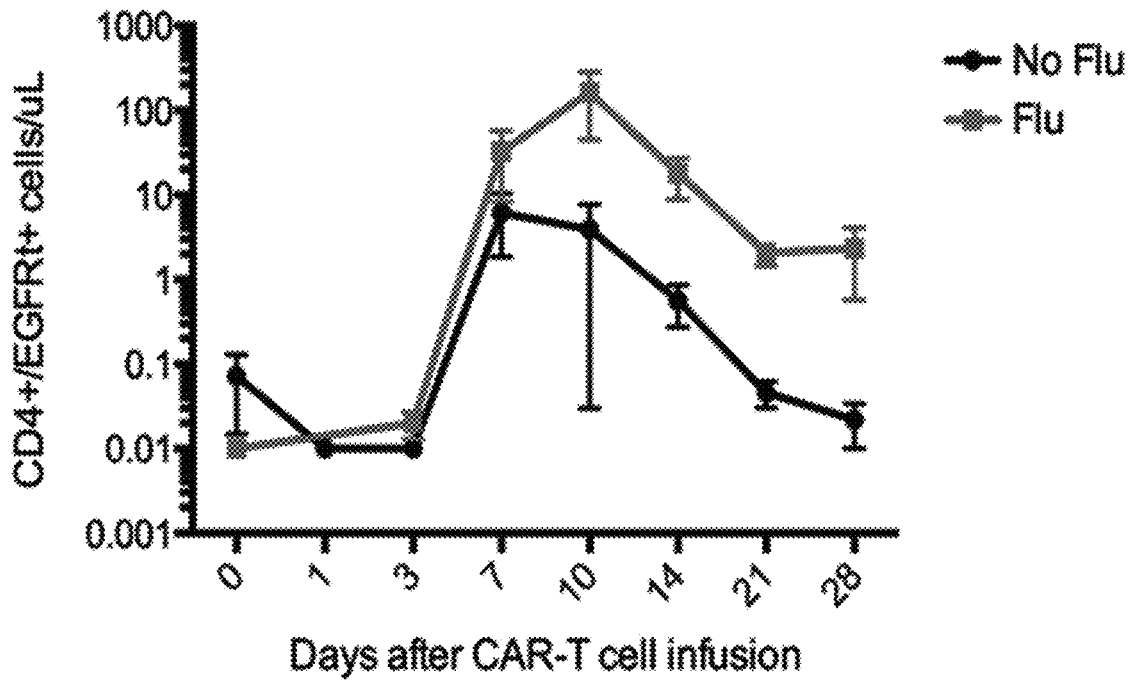
FIG. 6A shows the number of CD8+ CAR-expressing T cells (CD8$^+$/EGFR$^+$) per µL of peripheral blood of subjects treated with a single infusion of $2\times10^5$ or $2\times10^6$ CAR-expressing T cells over a 28 day period following the infusion, as measured by flow cytometry. Prior to the infusion, subjects were pre-conditioned with 2 g/m$^2$ cyclophosphamide with or without 3 doses of 100 mg/m$^2$ etoposide (No Flu), or were treated with 60 mg/kg (~2 g/m$^2$) cyclophosphamide and 3 to 5 doses of 25 mg/m$^2$ fludarabine (Flu).
Figure 6B:
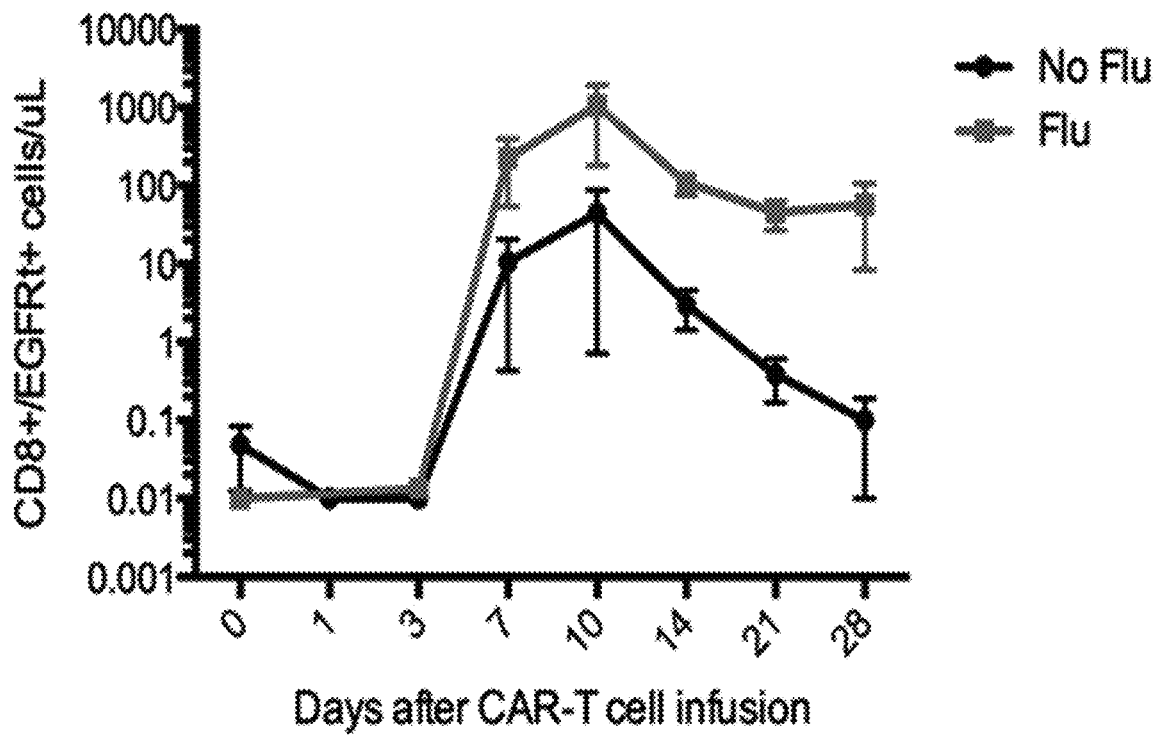
FIG. 6B shows the number of CD4+ CAR-expressing T cells (CD4$^+$/EGFR$^+$) per µL of peripheral blood of subjects treated with a single infusion of $2\times10^5$ or $2\times10^6$ CAR-expressing T cells over a 28 day period following the infusion, as measured by flow cytometry. Prior to the infusion, subjects were pre-conditioned with 2 g/m$^2$ cyclophosphamide with or without 3 doses of 100 mg/m$^2$ etoposide (No Flu), or were treated with 60 mg/kg (~2 g/m$^2$) cyclophosphamide and 3 to 5 doses of 25 mg/m$^2$ fludarabine (Flu).

As shown in FIGS. 6A and 6B, a greater degree of CAR-T cell expansion and/or persistence, as measured by the presence of CD8+ (FIG. 6A) or CD4+ (FIG. 6B) CAR-T cells in peripheral blood, was observed from days 7 to 28 post-treatment in subjects who were pre-conditioned with cyclophosphamide/fludarabine as compared with those who did not receive fludarabine prior to the administration of CAR-T cells. This result demonstrates that pre-conditioning with cyclophosphamide/fludarabine can impact in vivo CAR-T cell expansion.

Figure 6C:
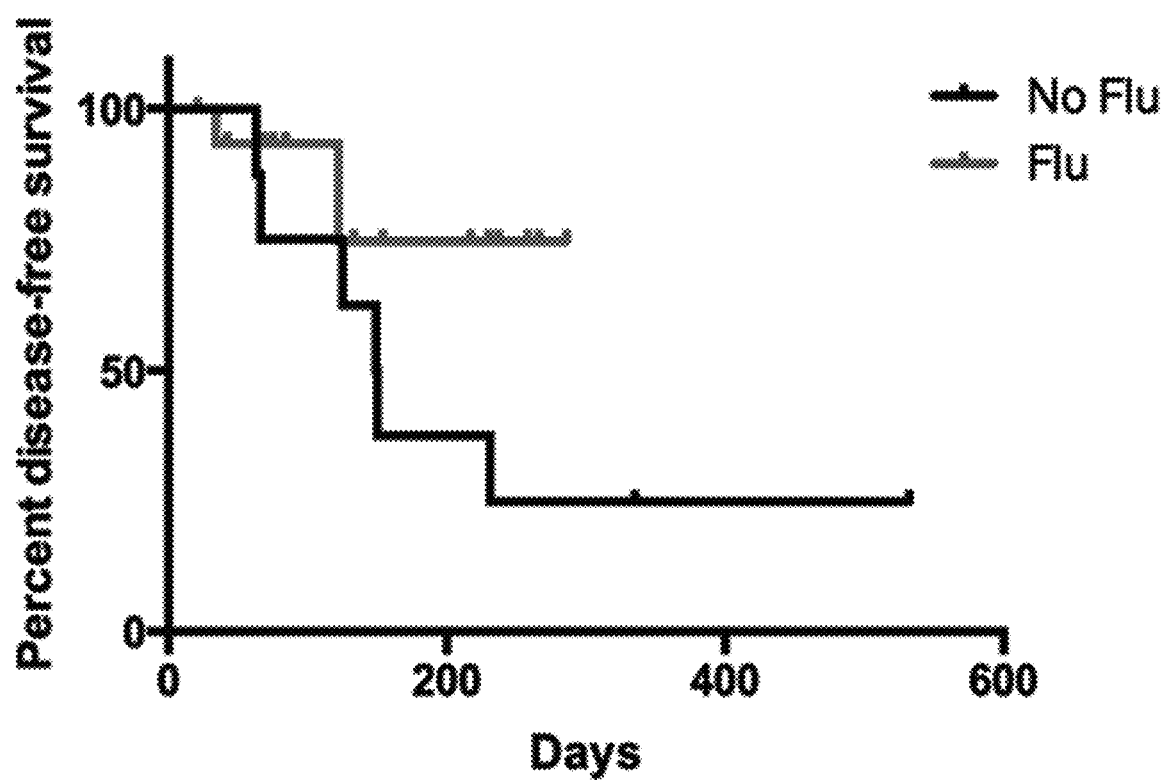
FIG. 6C shows percent disease-free survival curves for subjects treated with a single infusion of $2\times10^5$ or $2\times10^6$ CAR-expressing T cells. Prior to the infusion, subjects were pre-conditioned with 2 g/m$^2$ cyclophosphamide with or without 3 doses of 100 mg/m$^2$ etoposide (No Flu), or were treated with 60 mg/kg (~2 g/m$^2$) cyclophosphamide and 3 to 5 doses of 25 mg/m$^2$ fludarabine (Flu).

As shown in FIG. 6C, a greater percentage of patients exhibiting disease-free survival over the time period shown was observed among subjects having been pre-treated with both cyclophosphamide and fludarabine.

Example 12: Pre-Conditioning with Fludarabine Prior to CAR-T Cell Administration in Subjects with Non-Hodgkin Lymphoma (NHL)

Subjects with Non-Hodgkin Lymphoma (NHL) were administered $2\times10^7$ cells/kg of autologous T cells expressing an anti-CD19 chimeric antigen receptor (CAR). Before treatment, autologous CAR-expressing T cells were generated substantially as described in Example 2.

Prior to administration of the CAR-expressing T cells, subjects were treated either with 1) 2-4 g/m$^2$ cyclophosphamide (with or without administration of 100-200 mg/m$^2$ etoposide three times daily) (N=3, designated no Flu treated group), or 2) with 30-60 mg/kg (~1-2 g/m$^2$) cyclophosphamide and 3 to 5 doses of 25 mg/m$^2$ fludarabine (N=6, designated Cy/Flu treated group).

At days 0, 1, 3, 7, 10, 14, 21 and 28 post-treatment, the number of CAR-T cells present in peripheral blood of treated subjects was determined by performing flow cytometry of a cell sample for surface expression of EGFRt (CAR-specific marker) and CD4 or CD8.

Figure 7A:
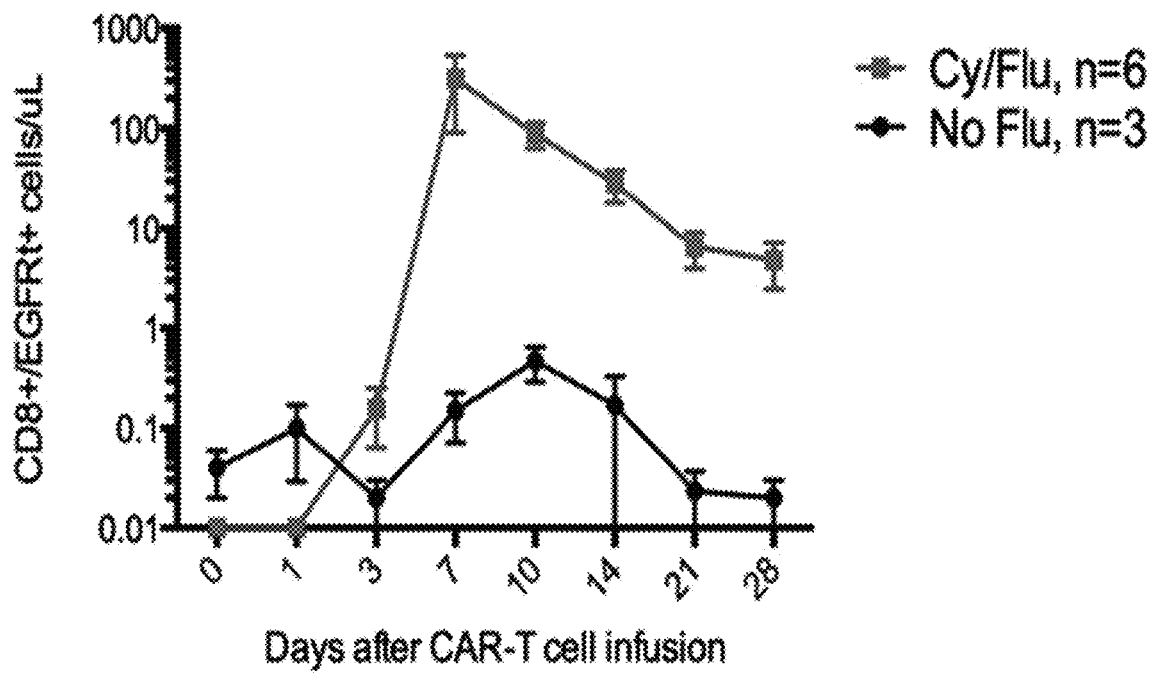
FIG. 7A shows the number (top panel) and percent (bottom panel) of CD8+ CAR-expressing T cells (CD8$^+$/EGFR$^+$) per µL of peripheral blood of subjects treated with a single infusion of $2\times10^7$ CAR-expressing T cells over a 28 day period following the infusion, as measured by flow cytometry. Prior to the infusion, subjects were pre-conditioned with 2-4 g/m$^2$ cyclophosphamide with or without 3 doses of 100-200 mg/m$^2$ etoposide (No Flu), or were treated with 30-60 mg/kg (~1-2 g/m$^2$) cyclophosphamide and 3 to 5 doses of 25 mg/m$^2$ fludarabine (Cy/Flu).
Figure 7A:
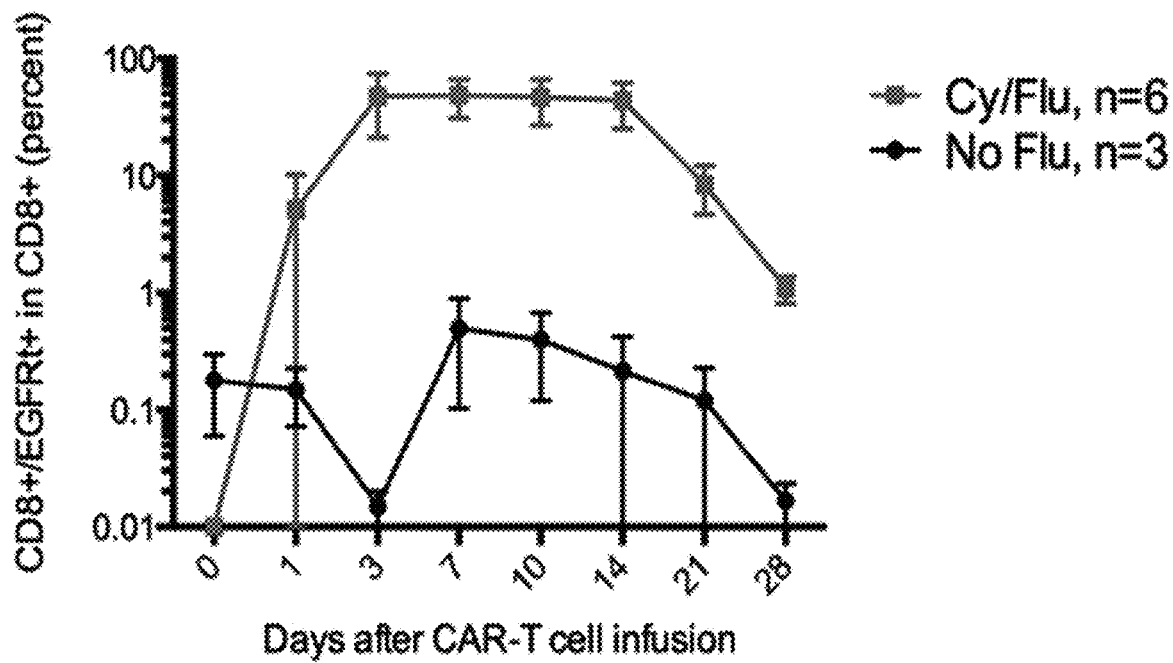
Figure 7B:
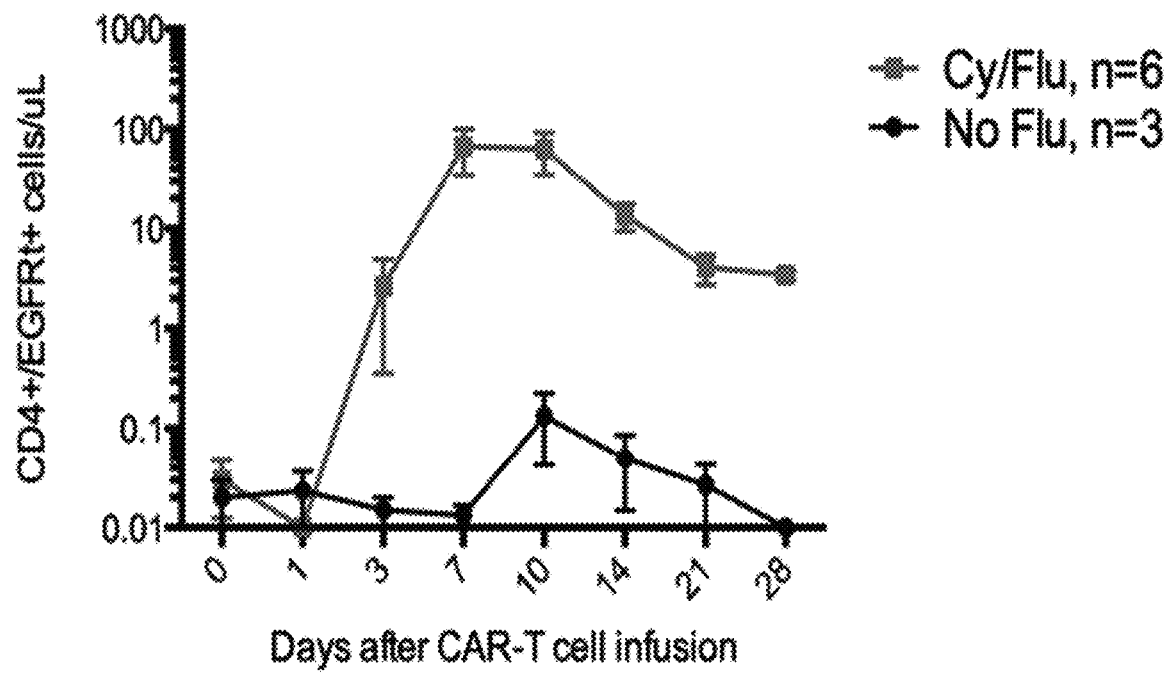
FIG. 7B shows the number (top panel) and percent (bottom panel) of CD4+ CAR-expressing T cells (CD4$^+$/EGFR$^+$) per µL of peripheral blood of subjects treated with a single infusion of $2\times10^7$ CAR-expressing T cells over a 28 day period following the infusion, as measured by flow cytometry. Prior to the infusion, subjects were pre-conditioned with 2-4 g/m$^2$ cyclophosphamide with or without 3 doses of 100-200 mg/m$^2$ etoposide (No Flu), or were treated with 30-60 mg/kg (~1-2 g/m$^2$) cyclophosphamide and 3 to 5 doses of 25 mg/m$^2$ fludarabine (Cy/Flu).
Figure 7B:
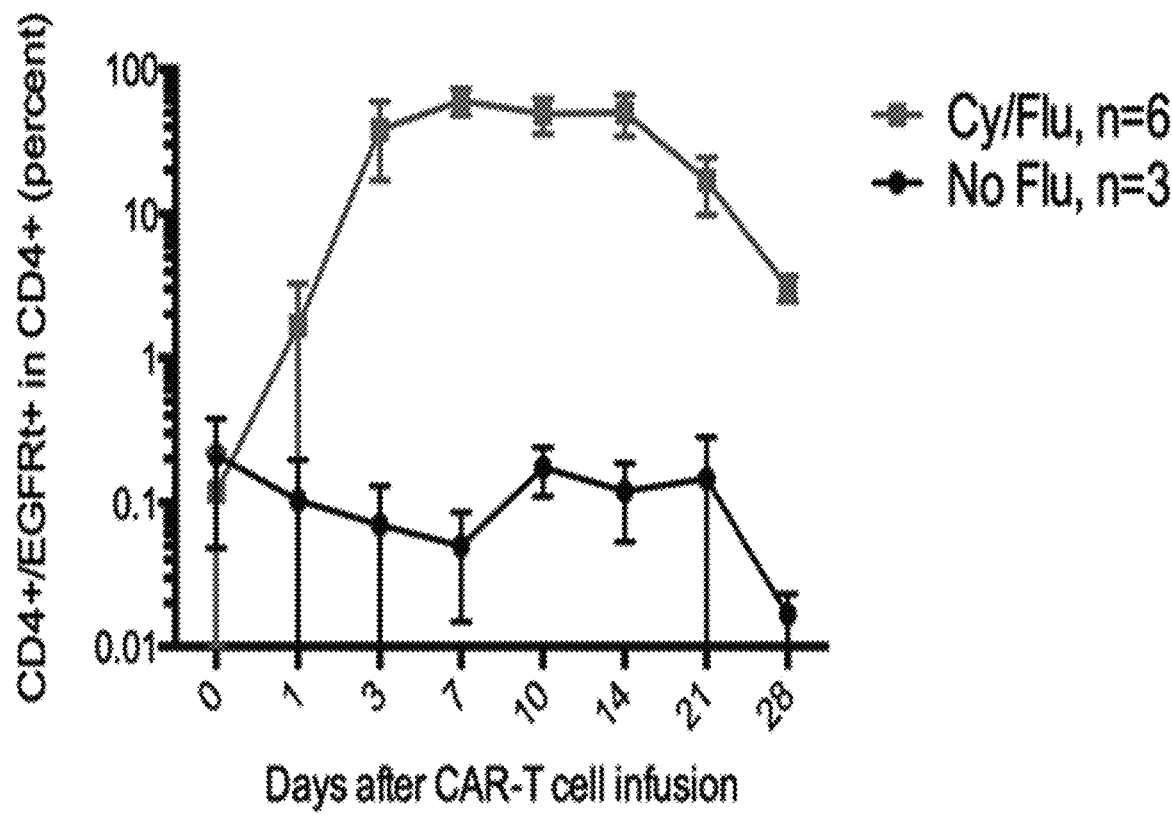

The results are depicted in FIGS. 7A and 7B, which set forth the CAR-expressing CD8+ or CD4+ T cells, respectively, as total cells per µL or as the total percentage of CD4+ or CD8+ cells, respectively, in the sample. As shown in FIGS. 7A and 7B, a greater degree of CAR-T cell expansion and/or persistence, as measured by the presence of CD8+

(FIG. 7A) or CD4⁺ (FIG. 7B) CAR-T cells in peripheral blood following treatment, was observed from days 3 to 28 post-treatment in subjects who were pre-conditioned with cyclophosphamide/fludarabine as compared to those who did not receive fludarabine prior to the administration of CAR-T cells. This result demonstrated that pre-conditioning with cyclophosphamide/fludarabine can impact in vivo CAR-T cell expansion in subjects with NHL.

Subjects were monitored for efficacy of treatment by measuring the overall remission rate (ORR). ORR was determined as the proportion of subjects with complete remission (CR) or partial remission (PR), as determined by examination of the bone marrow, peripheral blood, and cerebrospinal fluid (CSF), as well as physical examination and evaluation of central nervous system (CNS) symptoms.

The overall remission rate for subjects pre-conditioned with cyclophosphamide/fludarabine was 62% (8/13), including a 38% CR rate and 23% PR rate (CR=5/13, PR=3/13), while subjects who did not receive fludarabine pre-conditioning had an overall remission rate of 50% (6/12), including an 8% CR rate and a 42% PR rate (CR=1/12, PR=5/12).

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method of treatment, comprising administering a consecutive dose of T cells expressing a chimeric antigen receptor (CAR) that binds to CD19 to a subject having a hematologic malignancy and having been previously administered a first dose of T cells expressing a CAR that binds to CD19, wherein:
(i) the first dose comprises no more than about $1\times10^6$ of the cells per kilogram body weight of the subject (cells/kg), no more than about $1\times10^8$ of the cells, or no more than about $1\times10^8$ of the cells/m$^2$ of the subject; and
(ii) the consecutive dose of cells is administered between about 14 days after and about 28 days after initiation of the administration of the first dose of cells.

2. The method of treatment of claim 1, further comprising administering to the subject the first dose of cells.

3. The method of claim 1, wherein, at the time of the administration of the consecutive dose:
(i) the serum level in the subject of a factor indicative of cytokine release syndrome (CRS) is no more than about 50 times that in the subject immediately prior to the administration of the first dose; and/or
(ii) the subject does not exhibit grade 3 or higher neurotoxicity;
(iii) a CRS-related outcome or symptom of neurotoxicity in the subject has reached a peak level and begun to decline following the administration of the first dose; or
(iv) the subject does not exhibit a detectable humoral or cell-mediated immune response against the CAR expressed by the cells in the first dose.

4. The method of claim 1, wherein prior to the administration of the first dose of cells, the subject has not received a dose of cells expressing the CAR expressed by the cells in the first dose.

5. The method of claim 1, wherein the CAR expressed by the cells in the first dose and the CAR expressed by the cells in the consecutive dose contain the same antigen-binding domain.

6. The method of claim 1, wherein the CAR expressed by the cells in the consecutive dose is identical to the CAR expressed by the cells in the first dose.

7. The method of claim 1, wherein:
the first dose comprises cells in an amount sufficient for reduction in burden of the hematologic malignancy in the subject.

8. The method of claim 1, further comprising:
(i) assessing a factor indicative of disease burden after administration of the first dose of cells and prior to administration of the consecutive dose of cells;
(ii) based on the result of the assessment, determining the consecutive dose of cells to be administered to the subject; and
(iii) (1) if the assessment determines that the subject has morphologic disease, administering to the subject a consecutive dose comprising less than or about the same number of CAR-expressing cells as the number of CAR-expressing cells in the first dose; or
(2) if the assessment determines that the subject has minimal residual disease, administering to the subject a consecutive dose comprising an increased number of CAR-expressing cells as compared to the first dose.

9. The method of claim 1, wherein:
if at a time just prior to initiation of administration of the consecutive dose of cells, the subject exhibits morphologic disease, the consecutive dose comprises less than or about the same number of CAR-expressing cells as the number of CAR-expressing cells in the first dose.

10. The method of claim 1, wherein the number of CAR-expressing cells administered in the consecutive dose comprises between about $2\times10^6$ cells/kg- and about $6\times10^6$ cells/kg each inclusive.

11. The method of claim 1, wherein the time between the first dose and the consecutive dose is from about 15 to about 27 days, inclusive.

12. The method of claim 1, further comprising administering a chemotherapeutic agent prior to the administration of the consecutive dose of cells.

13. The method of claim 1, wherein the subject has been previously treated with a chemotherapeutic agent prior to administration of the first dose or prior to the administration of the consecutive dose.

14. The method of claim 12, wherein the chemotherapeutic agent comprises cyclophosphamide or fludarabine.

15. The method of claim 12, wherein the chemotherapeutic agent comprises cyclophosphamide and fludarabine.

16. The method of claim 13, wherein the chemotherapeutic agent comprises cyclophosphamide or fludarabine.

17. The method of claim 13, wherein the chemotherapeutic agent comprises cyclophosphamide and fludarabine.

18. The method of claim 1, wherein the subject was treated with a chemotherapeutic agent at a time that was subsequent to the initiation of the administration of the first dose and prior to the initiation of the administration of the consecutive dose.

19. The method of claim 1, wherein:
the first dose is a split dose, wherein the cells of the first dose are administered in a plurality of compositions, collectively comprising the cells of the first dose, over a period of no more than three days; or
the consecutive dose is a split dose, wherein the cells of the consecutive dose are administered in a plurality of compositions, collectively comprising the cells of the consecutive dose, over a period of no more than three days.

20. The method of claim 2, further comprising administering a chemotherapeutic agent prior to the administration of the first dose of cells.

21. The method of claim 1, wherein the hematologic malignancy is a leukemia or lymphoma.

22. The method of claim 1, wherein the hematologic malignancy is non-Hodgkin lymphoma (NHL).

23. The method of claim 1, wherein the number of CAR$^+$ cells administered in the first dose is at or about or no more than at or about $1\times10^6$ cells/kg the number of CAR$^+$ cells administered in the consecutive dose is at or about $3\times10^6$ cells/kg.

24. The method of claim 1, further comprising administering to the subject one or more additional subsequent doses, wherein the first additional subsequent dose is administered at a time that is at least 14 days after the initiation of the administration of the consecutive dose.

25. The method of claim 1, wherein
the consecutive dose is administered at a point in time at which:
(i) a clinical risk for neurotoxicity, cytokine-release syndrome (CRS), macrophage activation syndrome, or tumor lysis syndrome, is not present or has passed or has subsided following the administration of the first dose; (ii) a biochemical readout evidencing cytokine release syndrome (CRS), neurotoxicity, macrophage activation syndrome, or tumor lysis syndrome, is not present or has passed or has subsided following the administration of the first dose; (iii) a CRS-related outcome in the subject has reached a peak level and begun to decline following administration of the first dose; or (iv) a serum level of a factor indicative of CRS or neurotoxicity in the subject is no more than about 50 times the serum level of the factor in the subject immediately prior to the administration of the first dose; and
the subject does not exhibit a detectable adaptive host immune response specific for the CAR expressed by the cells of the first dose.

26. A method of treatment, comprising administering a consecutive dose of T cells expressing a chimeric antigen receptor (CAR) that binds to CD19 to a subject having a hematologic malignancy and having been previously administered a first dose of T cells expressing a CAR that binds to CD19, wherein:
(i) the first dose comprises no more than about $1\times10^6$ of the cells per kilogram body weight of the subject (cells/kg), no more than about $1\times10^8$ of the cells, or no more than about $1\times10^8$ of the cells/m$^2$ of the subject;
(ii) prior to administration of the consecutive dose, the subject does not exhibit morphologic disease; and
(iii) the number of CAR-expressing cells in the consecutive dose is increased as compared to the number of CAR-expressing cells in the first dose.

27. The method of claim 26, wherein the number of CAR$^+$ cells administered in the consecutive dose is at least about 2 times greater than the number of CAR$^+$ cells administered in the first dose.

28. The method of claim 26, further comprising administering to the subject the first dose of cells.

29. The method of claim 26, wherein prior to administration of the first dose of cells, the subject has not received a dose of cells expressing the CAR expressed by the cells in the first dose.

30. The method of claim 26, wherein the CAR expressed by the cells in the first dose and the CAR expressed by the cells in the consecutive dose contain the same antigen-binding domain.

31. The method of claim 26, wherein the CAR expressed by the cells in the consecutive dose is identical to the CAR expressed by the cells in the first dose.

32. The method of claim 26, wherein the first dose comprises cells in an amount sufficient for a reduction in burden of the hematologic malignancy in the subject.

33. The method of claim 26, wherein the number of CAR-expressing cells administered in the consecutive dose comprises between about $2\times10^6$ cells/kg and about $6\times10^6$ cells/kg.

34. The method of claim 26, further comprising administering a chemotherapeutic agent prior to the administration of the consecutive dose of cells.

35. The method of claim 26, wherein the subject has been previously treated with a chemotherapeutic agent prior to administration of the first dose or prior to the administration of the consecutive dose.

36. The method of claim 26, wherein the chemotherapeutic agent comprises cyclophosphamide or fludarabine.

37. The method of claim 26, wherein the chemotherapeutic agent comprises cyclophosphamide and fludarabine.

38. The method of claim 26, wherein the subject was treated with a chemotherapeutic agent at a time that was subsequent to the initiation of the administration of the first dose and prior to the initiation of the administration of the consecutive dose.

39. The method of claim 26, wherein:
the first dose is a split dose, wherein the cells of the first dose are administered in a plurality of compositions, collectively comprising the cells of the first dose, over a period of no more than three days; or
the consecutive dose is a split dose, wherein the cells of the consecutive dose are administered in a plurality of compositions, collectively comprising the cells of the consecutive dose, over a period of no more than three days.

40. The method of claim 26, wherein the hematologic malignancy is a leukemia or a lymphoma.

41. The method of claim 26, wherein the hematologic malignancy is a non-Hodgkin lymphoma (NHL).

42. The method of claim 23, wherein the first dose comprises no more than about $1\times10^8$ of the cells.

43. The method of claim 26, wherein the first dose comprises no more than about $1\times10^8$ of the cells.

* * * * *

UNITED STATES PATENT AND TRADEMARK OFFICE
CERTIFICATE OF CORRECTION

| | |
|---|---|
| PATENT NO. | : 11,633,426 B2 |
| APPLICATION NO. | : 16/667564 |
| DATED | : April 25, 2023 |
| INVENTOR(S) | : Mark J. Gilbert |

It is certified that error appears in the above-identified patent and that said Letters Patent is hereby corrected as shown below:

On the Title Page

At Column 2, under "Other Publications," please replace "expansion of of CAR" with -- expansion of CAR --.

In the Claims

At Column 110, Claim number 10, Line 56, please replace "cells/kg-and" with -- cells/kg and --.

At Column 111, Claim number 23, Line 34, please replace "cells/kg the" with -- cells/kg or the --.

Signed and Sealed this
Thirtieth Day of January, 2024

Katherine Kelly Vidal
*Director of the United States Patent and Trademark Office*

```
                       SEQUENCE LISTING

<160> NUMBER OF SEQ ID NOS: 15

<210> SEQ ID NO 1
<211> LENGTH: 12
<212> TYPE: PRT
<213> ORGANISM: Homo sapiens
<220> FEATURE:
<223> OTHER INFORMATION: spacer (IgG4hinge) (aa)

<400> SEQUENCE: 1

Glu Ser Lys Tyr Gly Pro Pro Cys Pro Pro Cys Pro
1               5                   10

<210> SEQ ID NO 2
<211> LENGTH: 36
<212> TYPE: PRT
<213> ORGANISM: Homo sapiens
<220> FEATURE:
<223> OTHER INFORMATION: spacer (IgG4hinge) (nt)

<400> SEQUENCE: 2

Gly Ala Ala Thr Cys Thr Ala Ala Gly Thr Ala Cys Gly Gly Ala Cys
1               5                   10                  15

Cys Gly Cys Cys Cys Thr Gly Cys Cys Cys Cys Cys Thr Thr Gly
            20                  25                  30

Cys Cys Cys Thr
        35

<210> SEQ ID NO 3
<211> LENGTH: 119
<212> TYPE: PRT
<213> ORGANISM: Homo sapiens
<220> FEATURE:
<223> OTHER INFORMATION: Hinge-CH3 spacer

<400> SEQUENCE: 3

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80
```

Arg Leu Thr Val Asp Lys Ser Arg Trp Gln Glu Gly Asn Val Phe Ser
            85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 4
<211> LENGTH: 229
<212> TYPE: PRT
<213> ORGANISM: Homo sapiens
<220> FEATURE:
<223> OTHER INFORMATION: Hinge-CH2-CH3 spacer

<400> SEQUENCE: 4

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 5
<211> LENGTH: 282
<212> TYPE: PRT
<213> ORGANISM: Homo sapiens
<220> FEATURE:
<223> OTHER INFORMATION: IgD-hinge-Fc

<400> SEQUENCE: 5

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

```
Thr Thr Arg Asn Thr Gly Arg Gly Gly Glu Lys Lys Lys Glu Lys
        35                  40                  45

Glu Lys Glu Glu Gln Glu Glu Arg Glu Thr Lys Thr Pro Glu Cys Pro
 50                  55                  60

Ser His Thr Gln Pro Leu Gly Val Tyr Leu Leu Thr Pro Ala Val Gln
 65                  70                  75                  80

Asp Leu Trp Leu Arg Asp Lys Ala Thr Phe Thr Cys Phe Val Val Gly
                 85                  90                  95

Ser Asp Leu Lys Asp Ala His Leu Thr Trp Glu Val Ala Gly Lys Val
                100                 105                 110

Pro Thr Gly Gly Val Glu Glu Gly Leu Leu Glu Arg His Ser Asn Gly
                115                 120                 125

Ser Gln Ser Gln His Ser Arg Leu Thr Leu Pro Arg Ser Leu Trp Asn
130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
                180                 185                 190

Trp Leu Leu Cys Glu Val Ser Gly Phe Ser Pro Pro Asn Ile Leu Leu
                195                 200                 205

Met Trp Leu Glu Asp Gln Arg Glu Val Asn Thr Ser Gly Phe Ala Pro
                210                 215                 220

Ala Arg Pro Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
                260                 265                 270

Ser Leu Glu Val Ser Tyr Val Thr Asp His
                275                 280

<210> SEQ ID NO 6
<211> LENGTH: 27
<212> TYPE: PRT
<213> ORGANISM: Homo sapiens
<220> FEATURE:
<223> OTHER INFORMATION: CD28  (amino acids 153-179 of Accession No.
      P10747)

<400> SEQUENCE: 6

Phe Trp Val Leu Val Val Val Gly Gly Val Leu Ala Cys Tyr Ser Leu
1               5                   10                  15

Leu Val Thr Val Ala Phe Ile Ile Phe Trp Val
                20                  25

<210> SEQ ID NO 7
<211> LENGTH: 66
<212> TYPE: PRT
<213> ORGANISM: Homo sapiens
<220> FEATURE:
<223> OTHER INFORMATION: CD28 (amino acids 114-179 of Accession No.
      P10747)

<400> SEQUENCE: 7

Ile Glu Val Met Tyr Pro Pro Pro Tyr Leu Asp Asn Glu Lys Ser Asn
1               5                   10                  15
```

-continued

Gly Thr Ile Ile His Val Lys Gly Lys His Leu Cys Pro Ser Pro Leu
                20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65

<210> SEQ ID NO 8
<211> LENGTH: 41
<212> TYPE: PRT
<213> ORGANISM: Homo sapiens
<220> FEATURE:
<223> OTHER INFORMATION: CD28 (amino acids 180-220 of P10747)

<400> SEQUENCE: 8

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 9
<211> LENGTH: 41
<212> TYPE: PRT
<213> ORGANISM: Homo sapiens
<220> FEATURE:
<223> OTHER INFORMATION: CD28 (LL to GG)

<400> SEQUENCE: 9

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 10
<211> LENGTH: 42
<212> TYPE: PRT
<213> ORGANISM: Homo sapiens
<220> FEATURE:
<223> OTHER INFORMATION: 4-1BB (amino acids 214-255 of Q07011.1)

<400> SEQUENCE: 10

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 11
<211> LENGTH: 112
<212> TYPE: PRT
<213> ORGANISM: Homo sapiens
<220> FEATURE:
<223> OTHER INFORMATION: CD3 zeta

<400> SEQUENCE: 11

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 12
<211> LENGTH: 112
<212> TYPE: PRT
<213> ORGANISM: Homo sapiens
<220> FEATURE:
<223> OTHER INFORMATION: CD3 zeta

<400> SEQUENCE: 12

Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 13
<211> LENGTH: 112
<212> TYPE: PRT
<213> ORGANISM: Homo sapiens
<220> FEATURE:
<223> OTHER INFORMATION: CD3 zeta

<400> SEQUENCE: 13

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 14
<211> LENGTH: 24
<212> TYPE: PRT
<213> ORGANISM: Artificial Sequence
<220> FEATURE:
<223> OTHER INFORMATION: Synthetic
<220> FEATURE:
<223> OTHER INFORMATION: T2A

<400> SEQUENCE: 14

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 15
<211> LENGTH: 357
<212> TYPE: PRT
<213> ORGANISM: Artificial Sequence
<220> FEATURE:
<223> OTHER INFORMATION: Synthetic
<220> FEATURE:
<223> OTHER INFORMATION: tEGFR

<400> SEQUENCE: 15

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

-continued

```
Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Val Val Ala Leu Gly
            340                 345                 350

Ile Gly Leu Phe Met
        355
```